(12) United States Patent
Brown et al.

(10) Patent No.: US 10,537,452 B2
(45) Date of Patent: *Jan. 21, 2020

(54) LUMINAL STENTING

(71) Applicant: Covidien LP, Mansfield, MA (US)

(72) Inventors: Kenneth Brown, Oceanside, CA (US); Ghislain Sema, West Covina, CA (US); Michael Losordo, San Juan Capistrano, CA (US); Evan Epstein, Costa Mesa, CA (US); Gabriel Newell, San Francisco, CA (US); Andy Huynh, Westminster, CA (US); Lawrence Farhat, Santa Rosa, CA (US)

(73) Assignee: COVIDIEN LP, Mansfield, MA (US)

(*) Notice: Subject to any disclaimer, the term of this patent is extended or adjusted under 35 U.S.C. 154(b) by 379 days.

This patent is subject to a terminal disclaimer.

(21) Appl. No.: 15/652,329

(22) Filed: Jul. 18, 2017

(65) Prior Publication Data

US 2017/0325980 A1   Nov. 16, 2017

Related U.S. Application Data

(63) Continuation of application No. 14/754,766, filed on Jun. 30, 2015, now Pat. No. 9,724,221, which is a
(Continued)

(51) Int. Cl.
*A61F 2/962* (2013.01)
*A61F 2/95* (2013.01)
(Continued)

(52) U.S. Cl.
CPC ............. *A61F 2/962* (2013.01); *A61B 90/39* (2016.02); *A61F 2/95* (2013.01); *A61F 2/966* (2013.01);
(Continued)

(58) Field of Classification Search
CPC ...... A61F 2002/9528; A61F 2002/9534; A61F 2/962; A61F 2/966; A61F 2002/9665
See application file for complete search history.

(56) References Cited

U.S. PATENT DOCUMENTS

| 3,416,531 A | 12/1968 | Edwards |
| 4,364,391 A | 12/1982 | Toye |

(Continued)

FOREIGN PATENT DOCUMENTS

| CN | 102159157 | 8/2011 |
| CN | 102958474 | 3/2013 |

(Continued)

OTHER PUBLICATIONS

Covidien's Pipeline Embolization Device and Delivery System Product Description and Instructions for Use Jun. 2010.

*Primary Examiner* — Wade Miles
(74) *Attorney, Agent, or Firm* — Fortem IP LLP; Matthew Lincicum

(57) ABSTRACT

A stent delivery system can include a core member, first and second restraints, and a stent engagement component. The core member can have a distal segment. The first and second restraints can be coupled to the core member distal segment and axially spaced apart from each other to provide an axial gap. The first and second restraints can each have an outer profile that tapers radially inwardly in directions away from the gap. The stent engagement component can be at least partially disposed in the axial gap between the first and second restraints such that the component is slidably and rotatably coupled to the core member distal segment.

17 Claims, 21 Drawing Sheets

Related U.S. Application Data continuation of application No. 14/040,501, filed on Sep. 27, 2013, now Pat. No. 9,072,624, which is a continuation-in-part of application No. 13/692,021, filed on Dec. 3, 2012, now Pat. No. 8,591,566.

(60) Provisional application No. 61/870,755, filed on Aug. 27, 2013, provisional application No. 61/679,106, filed on Aug. 3, 2012, provisional application No. 61/602,567, filed on Feb. 23, 2012.

(51) Int. Cl.
  *A61F 2/966*   (2013.01)
  *A61F 2/97*   (2013.01)
  *A61M 25/00*   (2006.01)
  *A61B 90/00*   (2016.01)
  *A61M 25/06*   (2006.01)

(52) U.S. Cl.
  CPC ........... *A61F 2/97* (2013.01); *A61M 25/0068* (2013.01); *A61B 2090/3966* (2016.02); *A61F 2002/9522* (2013.01); *A61F 2002/9665* (2013.01); *A61M 2025/0042* (2013.01); *A61M 2025/0681* (2013.01)

(56) References Cited

U.S. PATENT DOCUMENTS

| | | |
|---|---|---|
| 4,425,919 A | 1/1984 | Alston, Jr. et al. |
| 4,516,972 A | 5/1985 | Samson |
| 4,655,771 A | 4/1987 | Wallsten |
| 4,723,936 A | 2/1988 | Buchbinder et al. |
| 4,790,831 A | 12/1988 | Skribiski |
| 4,830,003 A * | 5/1989 | Wolff ................. A61F 2/86 606/191 |
| 4,990,151 A | 2/1991 | Wallsten |
| 5,011,478 A | 4/1991 | Cope |
| 5,026,377 A | 6/1991 | Burton et al. |
| 5,037,404 A | 8/1991 | Gold et al. |
| 5,098,393 A | 3/1992 | Amplatz et al. |
| 5,108,411 A | 4/1992 | McKenzie |
| 5,147,370 A | 9/1992 | McNamara et al. |
| 5,178,158 A | 1/1993 | de Toledo |
| 5,201,316 A | 4/1993 | Pomeranz et al. |
| 5,209,734 A | 5/1993 | Hurley et al. |
| 5,279,562 A | 1/1994 | Sirhan et al. |
| 5,279,596 A | 1/1994 | Castaneda et al. |
| 5,292,311 A | 3/1994 | Cope |
| 5,318,032 A | 6/1994 | Lonsbury et al. |
| 5,318,529 A | 6/1994 | Kontos |
| 5,358,493 A | 10/1994 | Schweich, Jr. et al. |
| 5,382,259 A | 1/1995 | Phelps et al. |
| 5,389,087 A | 2/1995 | Miraki |
| 5,403,292 A | 4/1995 | Ju |
| 5,437,288 A | 8/1995 | Schwartz et al. |
| 5,445,646 A | 8/1995 | Euteneuer et al. |
| 5,454,795 A | 10/1995 | Samson |
| 5,458,605 A | 10/1995 | Klemm |
| 5,474,563 A | 12/1995 | Myler et al. |
| 5,478,349 A | 12/1995 | Nicholas |
| 5,484,444 A | 1/1996 | Braunschweiler et al. |
| 5,496,294 A | 3/1996 | Hergenrother et al. |
| 5,499,975 A | 3/1996 | Cope et al. |
| 5,522,822 A | 6/1996 | Phelps et al. |
| 5,531,721 A | 7/1996 | Pepin et al. |
| 5,534,007 A | 7/1996 | St. Germain et al. |
| 5,545,209 A | 8/1996 | Roberts et al. |
| 5,554,139 A | 9/1996 | Okajima |
| 5,569,220 A | 10/1996 | Webster, Jr. |
| 5,571,135 A * | 11/1996 | Fraser ................. A61F 2/95 606/198 |
| 5,573,520 A | 11/1996 | Schwartz et al. |
| 5,584,821 A | 12/1996 | Hobbs et al. |
| 5,599,325 A | 2/1997 | Ju et al. |
| 5,599,326 A | 2/1997 | Carter |
| 5,601,539 A | 2/1997 | Corso, Jr. |
| 5,636,641 A | 6/1997 | Fariabi |
| 5,645,559 A | 7/1997 | Hachtman et al. |
| 5,658,264 A | 8/1997 | Samson |
| 5,662,622 A | 9/1997 | Gore et al. |
| 5,676,659 A | 10/1997 | McGurk |
| 5,695,483 A | 12/1997 | Samson |
| 5,695,499 A | 12/1997 | Helgerson et al. |
| 5,702,373 A | 12/1997 | Samson |
| 5,702,418 A * | 12/1997 | Ravenscroft ............. A61F 2/95 606/108 |
| 5,704,926 A | 1/1998 | Sutton |
| 5,709,703 A | 1/1998 | Lukic et al. |
| 5,711,909 A | 1/1998 | Gore et al. |
| 5,725,513 A | 3/1998 | Ju et al. |
| 5,725,571 A | 3/1998 | Imbert et al. |
| 5,728,063 A | 3/1998 | Preissman et al. |
| 5,741,429 A | 4/1998 | Donadio, III et al. |
| 5,743,876 A | 4/1998 | Swanson |
| 5,759,173 A | 6/1998 | Preissman et al. |
| 5,772,641 A | 6/1998 | Wilson |
| 5,782,811 A | 7/1998 | Samson et al. |
| 5,791,036 A | 8/1998 | Goodin et al. |
| 5,795,341 A | 8/1998 | Samson |
| 5,833,632 A | 11/1998 | Jacobsen et al. |
| 5,836,925 A | 11/1998 | Soltesz |
| 5,836,926 A | 11/1998 | Peterson et al. |
| 5,851,203 A | 12/1998 | van Muiden |
| 5,853,400 A | 12/1998 | Samson |
| 5,873,866 A | 2/1999 | Kondo et al. |
| 5,876,386 A | 3/1999 | Samson |
| 5,891,112 A | 4/1999 | Samson |
| 5,897,529 A | 4/1999 | Ponzi |
| 5,897,537 A | 4/1999 | Berg et al. |
| 5,902,290 A | 5/1999 | Peacock, III et al. |
| 5,906,605 A | 5/1999 | Coxum |
| 5,935,161 A | 8/1999 | Robinson et al. |
| 5,938,653 A | 8/1999 | Pepin |
| 5,951,494 A | 9/1999 | Wang et al. |
| 5,951,539 A | 9/1999 | Nita et al. |
| 5,961,510 A | 10/1999 | Fugoso et al. |
| 5,968,053 A | 10/1999 | Revelas |
| 5,971,975 A | 10/1999 | Mills et al. |
| 5,984,963 A | 11/1999 | Ryan et al. |
| 6,017,323 A | 1/2000 | Chee |
| 6,030,371 A | 2/2000 | Pursley |
| 6,045,547 A | 4/2000 | Ren et al. |
| 6,053,903 A | 4/2000 | Samson |
| 6,053,904 A | 4/2000 | Scribner et al. |
| 6,077,258 A | 6/2000 | Lange et al. |
| 6,077,295 A | 6/2000 | Limon et al. |
| 6,077,297 A | 6/2000 | Robinson et al. |
| 6,083,152 A | 7/2000 | Strong |
| 6,093,177 A | 7/2000 | Javier, Jr. et al. |
| 6,105,651 A | 8/2000 | Leanna |
| 6,106,510 A | 8/2000 | Lunn et al. |
| 6,106,540 A | 8/2000 | White et al. |
| 6,123,723 A | 9/2000 | Konya et al. |
| 6,126,685 A | 10/2000 | Lenker et al. |
| 6,135,992 A | 10/2000 | Wang |
| 6,149,680 A | 11/2000 | Shelso et al. |
| 6,152,912 A | 11/2000 | Jansen et al. |
| 6,152,944 A | 11/2000 | Holman et al. |
| 6,159,219 A | 12/2000 | Ren |
| 6,165,163 A | 12/2000 | Chien et al. |
| 6,165,166 A | 12/2000 | Samuelson et al. |
| 6,171,295 B1 | 1/2001 | Garabedian et al. |
| 6,171,296 B1 | 1/2001 | Chow |
| 6,171,297 B1 | 1/2001 | Pedersen et al. |
| 6,186,986 B1 | 2/2001 | Berg et al. |
| 6,193,739 B1 | 2/2001 | Chevillon et al. |
| 6,197,015 B1 | 3/2001 | Wilson |
| 6,217,565 B1 | 4/2001 | Cohen |
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |

(56) References Cited

U.S. PATENT DOCUMENTS

| | | |
|---|---|---|
| 6,325,807 B1 | 12/2001 | Que |
| 6,350,278 B1 | 2/2002 | Lenker et al. |
| 6,355,027 B1 | 3/2002 | Le et al. |
| 6,358,238 B1 | 3/2002 | Sherry |
| 6,358,460 B1 | 3/2002 | Hunt, Jr. et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |
| 6,428,552 B1 | 8/2002 | Sparks |
| 6,443,971 B1 | 9/2002 | Boylan et al. |
| 6,458,075 B1 | 10/2002 | Sugiyama et al. |
| 6,464,684 B1 | 10/2002 | Galdonik |
| 6,468,298 B1 | 10/2002 | Pelton |
| 6,475,184 B1 | 11/2002 | Wang et al. |
| 6,494,907 B1 | 12/2002 | Bulver |
| 6,508,804 B2 | 1/2003 | Sarge et al. |
| 6,508,805 B1 | 1/2003 | Garabedian et al. |
| 6,508,806 B1 | 1/2003 | Hoste |
| 6,517,547 B1 | 2/2003 | Feeser et al. |
| 6,554,820 B1 | 4/2003 | Wendlandt et al. |
| 6,562,021 B1 | 5/2003 | Derbin et al. |
| 6,562,063 B1 | 5/2003 | Euteneuer et al. |
| 6,576,006 B2 | 6/2003 | Limon et al. |
| 6,582,460 B1 | 6/2003 | Cryer |
| 6,589,227 B2 | 7/2003 | Klint |
| 6,602,271 B2 | 8/2003 | Adams et al. |
| 6,607,551 B1 | 8/2003 | Sullivan et al. |
| 6,622,367 B1 | 9/2003 | Bolduc et al. |
| 6,635,047 B2 | 10/2003 | Forsberg |
| 6,638,245 B2 | 10/2003 | Miller et al. |
| 6,641,564 B1 | 11/2003 | Kraus |
| 6,648,654 B1 | 11/2003 | Akram et al. |
| 6,648,874 B2 | 11/2003 | Parisi et al. |
| 6,652,508 B2 | 11/2003 | Griffin et al. |
| 6,663,614 B1 | 12/2003 | Carter |
| 6,669,719 B2 * | 12/2003 | Wallace .......... A61B 17/12118 606/108 |
| 6,689,120 B1 | 2/2004 | Gerdts |
| 6,699,274 B2 | 3/2004 | Stinson |
| 6,702,782 B2 | 3/2004 | Miller et al. |
| 6,706,055 B2 | 3/2004 | Douk et al. |
| 6,716,207 B2 | 4/2004 | Farnholtz |
| 6,726,659 B1 | 4/2004 | Stocking et al. |
| 6,764,504 B2 * | 7/2004 | Wang .................. A61F 2/958 606/194 |
| 6,808,529 B2 | 10/2004 | Fulkerson |
| 6,815,325 B2 | 11/2004 | Ishii |
| 6,817,995 B1 | 11/2004 | Halpern |
| 6,830,575 B2 * | 12/2004 | Stenzel .................. A61F 2/95 606/108 |
| 6,837,890 B1 | 1/2005 | Chludzinski et al. |
| 6,843,802 B1 | 1/2005 | Villalobos et al. |
| 6,858,024 B1 | 2/2005 | Berg et al. |
| 6,866,660 B2 | 3/2005 | Garabedian et al. |
| 6,866,679 B2 | 3/2005 | Kusleika |
| 6,932,837 B2 | 8/2005 | Amplatz et al. |
| 6,939,353 B2 | 9/2005 | Que et al. |
| 6,945,970 B2 | 9/2005 | Pepin |
| 6,960,227 B2 | 11/2005 | Jones et al. |
| 6,989,024 B2 | 1/2006 | Hebert et al. |
| 7,001,369 B2 | 2/2006 | Griffin et al. |
| 7,011,675 B2 | 3/2006 | Hemerick et al. |
| 7,025,758 B2 | 4/2006 | Klint |
| 7,074,236 B2 | 7/2006 | Rabkin et al. |
| 7,104,979 B2 | 9/2006 | Jansen et al. |
| 7,147,656 B2 | 12/2006 | Andreas et al. |
| 7,163,523 B2 | 1/2007 | Devens, Jr. et al. |
| 7,166,088 B2 | 1/2007 | Heuser |
| 7,166,099 B2 | 1/2007 | Devens, Jr. |
| 7,166,100 B2 | 1/2007 | Jordan et al. |
| 7,172,575 B2 | 2/2007 | El-Nounou et al. |
| 7,228,878 B2 | 6/2007 | Chen et al. |
| 7,306,624 B2 | 12/2007 | Yodfat et al. |
| 7,323,000 B2 | 1/2008 | Monstdt et al. |
| 7,331,948 B2 | 2/2008 | Skarda |
| 7,357,812 B2 | 4/2008 | Andreas et al. |
| 7,371,248 B2 | 5/2008 | Dapolito et al. |
| 7,402,151 B2 | 7/2008 | Rosenman et al. |
| 7,427,288 B2 | 9/2008 | Sater |
| 7,438,712 B2 | 10/2008 | Chouinard |
| 7,445,684 B2 | 11/2008 | Pursley |
| 7,473,271 B2 | 1/2009 | Gunderson |
| 7,473,272 B2 | 1/2009 | Pryor |
| 7,481,804 B2 | 1/2009 | Devens, Jr. |
| 7,507,229 B2 | 3/2009 | Hewitt et al. |
| 7,524,322 B2 | 4/2009 | Monstdt et al. |
| 7,556,634 B2 | 7/2009 | Lee et al. |
| 7,556,710 B2 | 7/2009 | Leeflang et al. |
| 7,569,046 B2 | 8/2009 | Zhou |
| 7,572,290 B2 | 8/2009 | Yodfat et al. |
| 7,582,079 B2 | 9/2009 | Wendlandt et al. |
| 7,597,830 B2 | 10/2009 | Zhou |
| 7,621,904 B2 | 11/2009 | McFerran et al. |
| 7,641,646 B2 | 1/2010 | Kennedy, II |
| 7,651,520 B2 | 1/2010 | Fischell et al. |
| 7,655,031 B2 | 2/2010 | Tenne et al. |
| 7,674,411 B2 | 3/2010 | Berg et al. |
| 7,691,138 B2 | 4/2010 | Stenzel et al. |
| 7,708,704 B2 | 5/2010 | Mitelberg et al. |
| 7,717,953 B2 | 5/2010 | Kaplan et al. |
| 7,758,624 B2 | 7/2010 | Dorn et al. |
| 7,766,820 B2 | 8/2010 | Core |
| 7,766,896 B2 | 8/2010 | Kornkven Volk et al. |
| 7,780,646 B2 | 8/2010 | Farnholtz |
| 7,815,600 B2 | 10/2010 | Al-Marashi et al. |
| 7,815,608 B2 | 10/2010 | Schafersman et al. |
| 7,815,628 B2 | 10/2010 | Devens, Jr. |
| 7,828,790 B2 | 11/2010 | Griffin |
| 7,867,267 B2 | 1/2011 | Sullivan et al. |
| 7,879,022 B2 | 2/2011 | Bonnette et al. |
| 7,942,925 B2 | 5/2011 | Yodfat et al. |
| 7,955,370 B2 | 6/2011 | Gunderson |
| 7,981,148 B2 | 7/2011 | Aguilar et al. |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,048,104 B2 | 11/2011 | Monstadt et al. |
| 8,066,754 B2 | 11/2011 | Malewicz |
| 8,083,791 B2 * | 12/2011 | Kaplan ............ A61F 2/91 623/1.35 |
| 8,088,140 B2 | 1/2012 | Ferrera et al. |
| 8,092,508 B2 | 1/2012 | Leynov et al. |
| 8,109,987 B2 * | 2/2012 | Kaplan ............ A61F 2/06 623/1.15 |
| 8,133,266 B2 | 3/2012 | Thomas et al. |
| 8,147,534 B2 | 4/2012 | Berez et al. |
| 8,159,219 B2 | 4/2012 | Estrada et al. |
| 8,187,314 B2 | 5/2012 | Davis et al. |
| 8,257,432 B2 * | 9/2012 | Kaplan ............ A61F 2/856 623/1.35 |
| 8,298,276 B2 | 10/2012 | Ozawa et al. |
| 8,317,850 B2 | 11/2012 | Kusleika |
| 8,366,763 B2 * | 2/2013 | Davis ............ A61F 2/856 623/1.16 |
| 8,382,818 B2 | 2/2013 | Davis et al. |
| 8,480,701 B2 | 7/2013 | Monstadt |
| 8,579,958 B2 | 11/2013 | Kusleika |
| 8,591,566 B2 * | 11/2013 | Newell ............ A61F 2/82 623/1.11 |
| 8,597,321 B2 | 12/2013 | Monstadt et al. |
| 8,603,014 B2 | 12/2013 | Alleman et al. |
| 8,790,387 B2 | 7/2014 | Nguyen et al. |
| 8,837,800 B1 | 9/2014 | Bammer et al. |
| 8,968,383 B1 | 3/2015 | Johnson et al. |
| 9,072,624 B2 | 7/2015 | Brown et al. |
| 9,119,656 B2 | 9/2015 | Bose et al. |
| 9,126,018 B1 | 9/2015 | Garrison |

(56) References Cited

U.S. PATENT DOCUMENTS

| | | |
|---|---|---|
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,724,221 B2 * | 8/2017 | Brown .................. A61F 2/966 |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0020173 A1 | 9/2001 | Klumb et al. |
| 2001/0027310 A1 | 10/2001 | Parisi et al. |
| 2001/0029362 A1 | 10/2001 | Sirhan et al. |
| 2001/0044591 A1 | 11/2001 | Stevens et al. |
| 2001/0049547 A1 | 12/2001 | Moore |
| 2002/0029046 A1 | 3/2002 | Lorentzen Cornelius et al. |
| 2002/0049412 A1 * | 4/2002 | Madrid .................. A61F 2/90 604/164.05 |
| 2002/0072789 A1 | 6/2002 | Hackett et al. |
| 2002/0107526 A1 | 8/2002 | Greenberg et al. |
| 2002/0111666 A1 | 8/2002 | Hart et al. |
| 2002/0138128 A1 | 9/2002 | Stiger et al. |
| 2002/0156459 A1 | 10/2002 | Ye et al. |
| 2002/0156460 A1 | 10/2002 | Ye et al. |
| 2002/0165523 A1 | 11/2002 | Chin et al. |
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1 | 7/2004 | Latini |
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |
| 2004/0220585 A1 | 11/2004 | Nikolchev |
| 2004/0230285 A1 | 11/2004 | Gifford et al. |
| 2004/0260271 A1 | 12/2004 | Huyser et al. |
| 2004/0260384 A1 | 12/2004 | Allen |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | McFerran |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 * | 10/2005 | Austin .................. A61F 2/95 623/1.11 |
| 2005/0273149 A1 | 12/2005 | Tran et al. |
| 2005/0277949 A1 | 12/2005 | Que et al. |
| 2006/0030835 A1 | 2/2006 | Sherman et al. |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | McFerran et al. |
| 2006/0095050 A1 | 5/2006 | Hartley et al. |
| 2006/0100687 A1 | 5/2006 | Fahey et al. |
| 2006/0116750 A1 | 6/2006 | Hebert et al. |
| 2006/0129166 A1 | 6/2006 | Lavelle |
| 2006/0178698 A1 | 8/2006 | McIntyre et al. |
| 2006/0184226 A1 | 8/2006 | Austin |
| 2006/0212042 A1 | 9/2006 | Lamport et al. |
| 2006/0217682 A1 | 9/2006 | Stivland et al. |
| 2006/0235502 A1 | 10/2006 | Belluche et al. |
| 2007/0027520 A1 | 2/2007 | Sherburne |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0161956 A1 | 7/2007 | Heuser |
| 2007/0185446 A1 | 8/2007 | Accisano |
| 2007/0203563 A1 * | 8/2007 | Hebert .................. A61F 2/962 623/1.12 |
| 2007/0233224 A1 | 10/2007 | Leynov et al. |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0009934 A1 | 1/2008 | Schneider et al. |
| 2008/0015558 A1 | 1/2008 | Harlan |
| 2008/0015678 A1 * | 1/2008 | Kaplan .................. A61F 2/91 623/1.11 |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von Oepen et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee Roth |
| 2008/0132933 A1 | 6/2008 | Gerber |
| 2008/0140180 A1 | 6/2008 | Dolan et al. |
| 2008/0147001 A1 | 6/2008 | Al-Marashi et al. |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahieh et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1 | 10/2008 | Hoffman et al. |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0262592 A1 | 10/2008 | Jordan et al. |
| 2008/0275426 A1 | 11/2008 | Holman et al. |
| 2008/0300667 A1 * | 12/2008 | Hebert .................. A61F 2/95 623/1.11 |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |

(56) References Cited

U.S. PATENT DOCUMENTS

| | | |
|---|---|---|
| 2009/0138066 A1* | 5/2009 | Leopold .............. A61F 2/07 623/1.12 |
| 2009/0143849 A1* | 6/2009 | Ozawa ............... A61F 2/94 623/1.11 |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1* | 3/2010 | Randolph ............. A61F 2/962 623/1.12 |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1 | 4/2010 | Beach et al. |
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |
| 2010/0217235 A1 | 8/2010 | Thorstenson et al. |
| 2010/0256602 A1 | 10/2010 | Lipped et al. |
| 2010/0256603 A1 | 10/2010 | Lipped et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0152760 A1* | 6/2011 | Parker ............... A61F 2/95 604/96.01 |
| 2011/0160763 A1 | 6/2011 | Ferrera et al. |
| 2011/0178588 A1 | 7/2011 | Haselby |
| 2011/0190862 A1* | 8/2011 | Bashiri .............. A61F 2/95 623/1.11 |
| 2011/0190865 A1 | 8/2011 | McHugo et al. |
| 2011/0208292 A1* | 8/2011 | Von Oepen .......... A61F 2/97 623/1.23 |
| 2011/0224650 A1 | 9/2011 | Itou et al. |
| 2011/0288626 A1 | 11/2011 | Straubinger et al. |
| 2011/0319904 A1 | 12/2011 | Hollett et al. |
| 2012/0029607 A1 | 2/2012 | McHugo et al. |
| 2012/0035700 A1 | 2/2012 | Leanne et al. |
| 2012/0053681 A1 | 3/2012 | Alkhatib et al. |
| 2012/0059449 A1* | 3/2012 | Dorn ................. A61F 2/95 623/1.12 |
| 2012/0065660 A1 | 3/2012 | Ferrera et al. |
| 2012/0116494 A1 | 5/2012 | Leynov et al. |
| 2012/0123511 A1 | 5/2012 | Brown |
| 2012/0253447 A1 | 10/2012 | Hayasaka et al. |
| 2012/0316638 A1 | 12/2012 | Grad et al. |
| 2013/0030461 A1 | 1/2013 | Marks et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274859 A1 | 10/2013 | Argentine |
| 2013/0281788 A1 | 10/2013 | Garrison |
| 2013/0282099 A1 | 10/2013 | Huynh |
| 2013/0304185 A1 | 11/2013 | Newell et al. |
| 2014/0025150 A1 | 1/2014 | Lim |
| 2014/0031918 A1 | 1/2014 | Newell et al. |
| 2014/0148893 A1 | 5/2014 | Kusleika |
| 2014/0171826 A1 | 6/2014 | Lampropoulos et al. |
| 2014/0194919 A1 | 7/2014 | Losordo et al. |
| 2014/0200648 A1* | 7/2014 | Newell ............... A61F 2/844 623/1.11 |
| 2014/0276074 A1 | 9/2014 | Warner |
| 2014/0343595 A1 | 11/2014 | Monstadt et al. |
| 2015/0032198 A1 | 1/2015 | Folk |
| 2015/0066128 A1 | 3/2015 | Losordo et al. |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0035592 A1 | 2/2017 | Haggstrom et al. |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| EP | 775470 | 5/1997 |
| EP | 1637176 | 3/2006 |
| EP | 1656963 | 5/2006 |
| EP | 2078512 | 7/2009 |
| EP | 2319575 B1 | 11/2013 |
| GB | 2179258 | 3/1987 |
| JP | 2014004219 A | 1/2014 |
| JP | 2018118132 A | 8/2018 |
| KR | 20180102877 A | 9/2018 |
| WO | WO96/01591 | 1/1996 |
| WO | WO01/49212 | 7/2001 |
| WO | WO01/89619 | 2/2002 |
| WO | WO2007/095031 | 8/2007 |
| WO | WO2007/117645 | 10/2007 |
| WO | WO2010/027485 | 3/2010 |
| WO | WO2010/086320 | 8/2010 |

(56) References Cited

FOREIGN PATENT DOCUMENTS

| | | |
|---|---|---|
| WO | WO2010/123831 | 10/2010 |
| WO | WO2010/127838 | 11/2010 |
| WO | WO2011/014814 | 2/2011 |
| WO | WO2011/076408 | 6/2011 |
| WO | WO2011/095966 | 8/2011 |
| WO | WO2011/144351 | 11/2011 |
| WO | WO2012/040240 | 3/2012 |
| WO | WO2012/158152 | 11/2012 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

\* cited by examiner

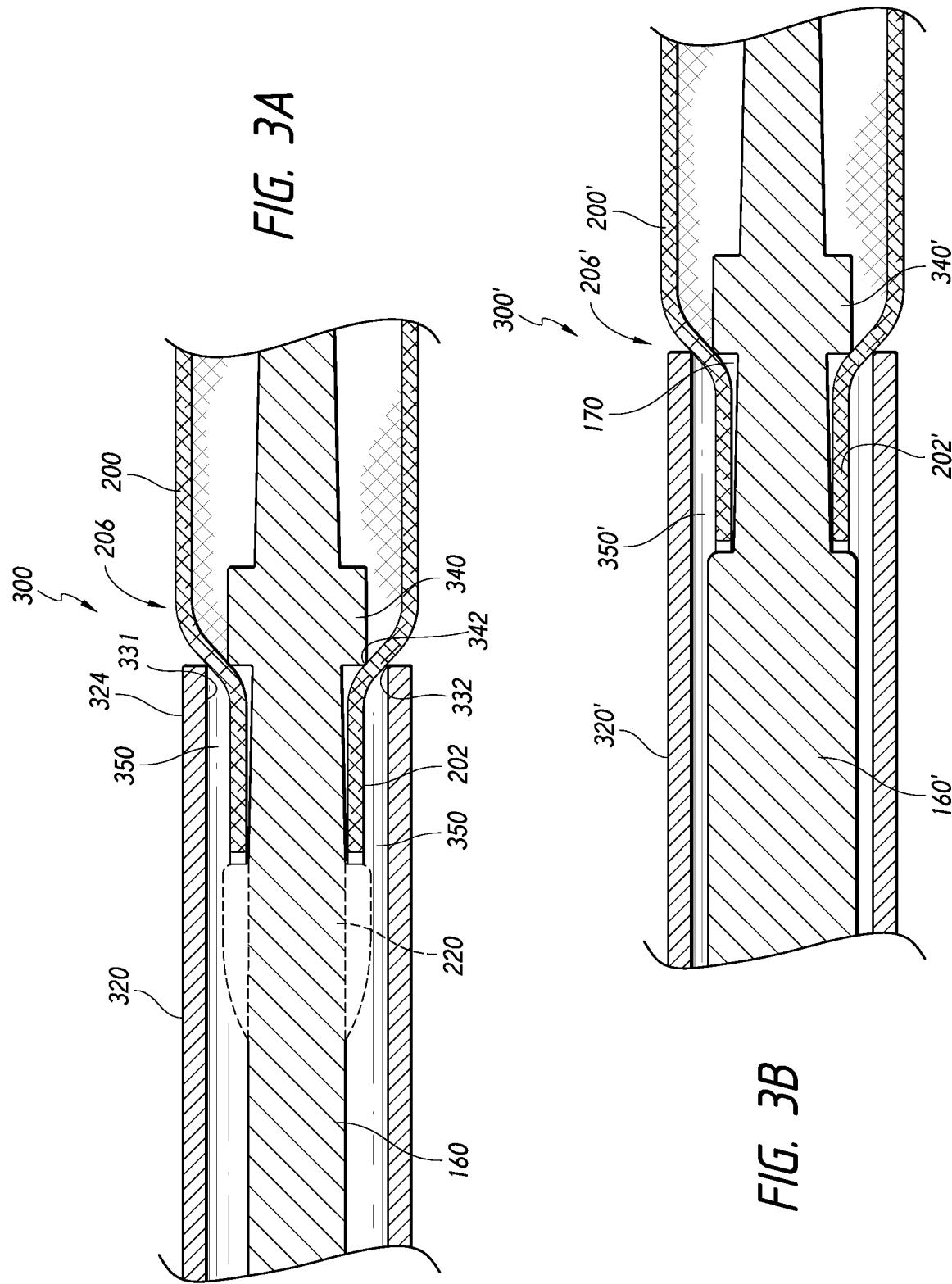

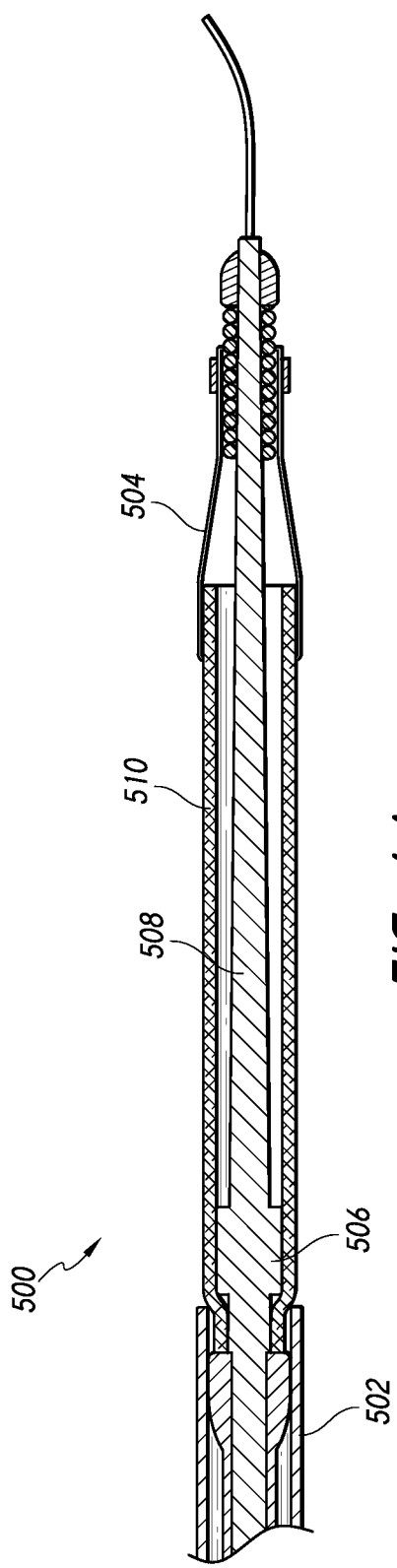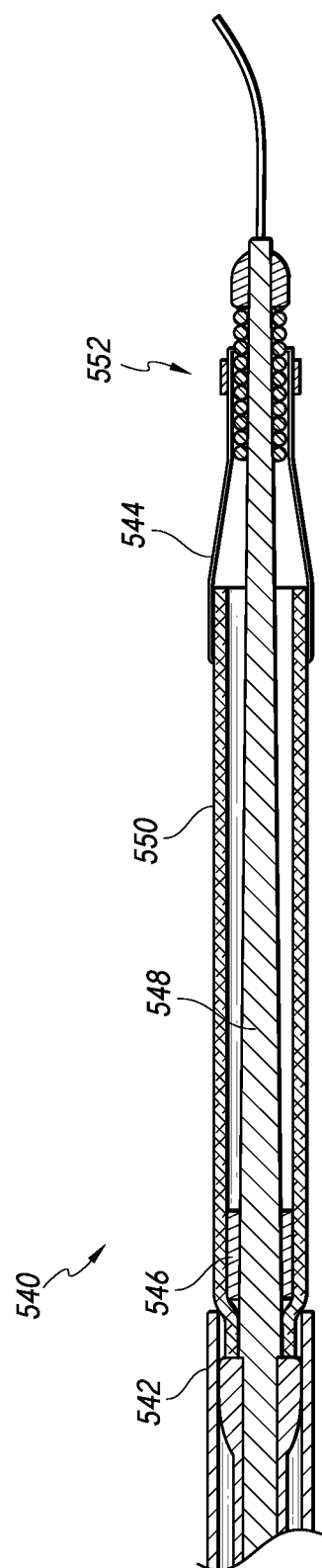
FIG. 4A
FIG. 4B

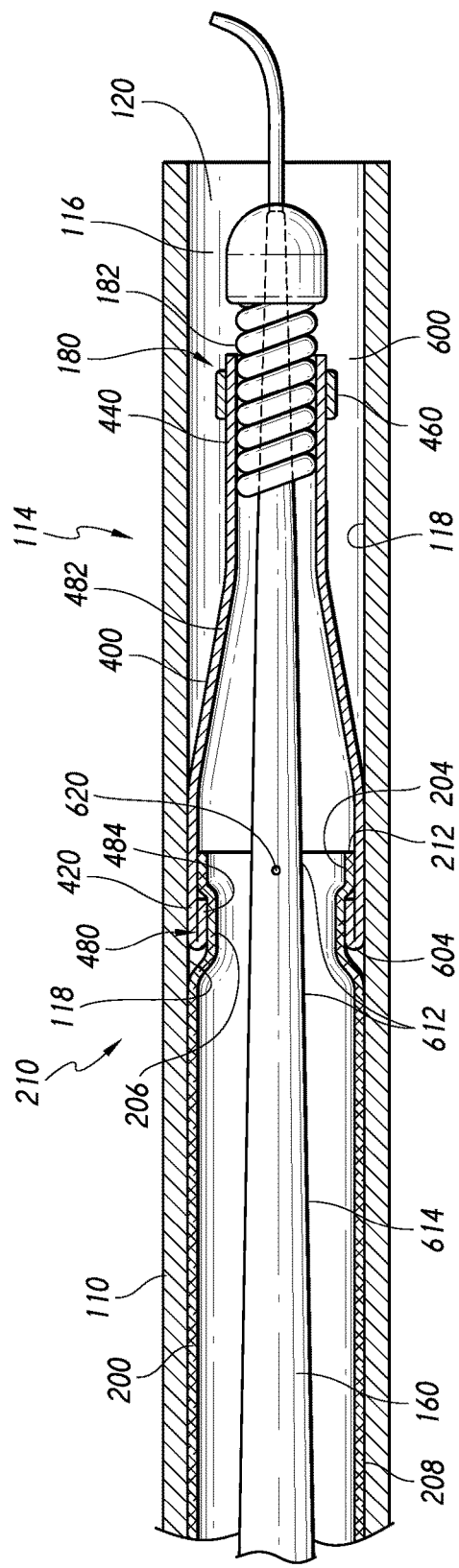
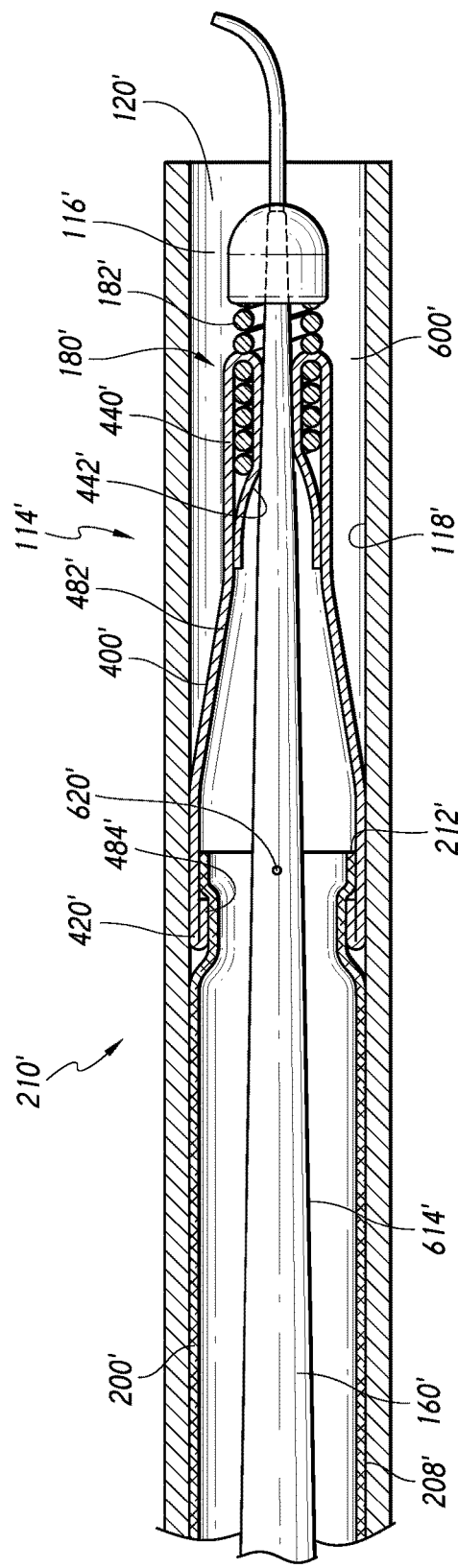
FIG. 5A
FIG. 5B

LUMINAL STENTING

CROSS-REFERENCE TO RELATED APPLICATIONS

This application is a continuation of U.S. patent application Ser. No. 14/754,766, filed Jun. 30, 2015, which is a continuation of U.S. patent application Ser. No. 14/040,501, filed Sep. 27, 2013, now U.S. Pat. No. 9,072,624, which claims the benefit of U.S. Provisional Application No. 61/870,755, filed Aug. 27, 2013. U.S. patent application Ser. No. 14/040,501, filed Sep. 27, 2013, now U.S. Pat. No. 9,072,624 is also a continuation-in-part of U.S. patent application Ser. No. 13/692,021, filed Dec. 3, 2012, now U.S. Pat. No. 8,591,566, which claims the benefit of U.S. Provisional Patent Application No. 61/602,567, filed Feb. 23, 2012, and U.S. Provisional Patent Application No. 61/679,106, filed Aug. 3, 2012. The entireties of each of the foregoing prior applications and patents are incorporated herein by reference.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neuro-vasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Methods for delivering these intravascular stents are also well known.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

SUMMARY

At least one aspect of the disclosure provides methods and apparatuses for delivering an occluding device or devices (e.g., stent or stents) in the body. The occluding device can easily conform to the shape of the tortuous vessels of the vasculature. The occluding device can be used in a variety of applications. For example, in some embodiments, the occluding device can direct the blood flow within a vessel away from an aneurysm. Additionally, such an occluding device can allow adequate blood flow to be provided to adjacent structures such that those structures, whether they are branch vessels or oxygen demanding tissues, are not deprived of the necessary blood flow.

The delivery of an intravascular stent to a treatment site within the vessel of a patient requires substantial precision. Generally, during the implantation process, a stent is passed through a vessel to a treatment location. The stent can be expanded at the treatment location, often by allowing a first end of the stent to expand and thereafter slowly expanding the remainder of the stent until the entire stent has been expanded. The process of initially contacting the vessel wall as the first end of the stent expands can be referred to as "landing" the stent. The final position of the stent within the vessel is generally determined by its initial placement or landing within the vessel. In some situations, the stent may initially be "landed" in a suboptimal location within the vessel. Using traditional methods and apparatuses, it may be very difficult for a clinician to reposition the stent within the vessel. For example, a clinician may be unable to recapture, collapse, withdraw, or resheath the stent back into the catheter after the stent has been partially expanded within the vessel. As such, the initial landing is critical to successful placement of the stent.

In accordance with an aspect of at least some embodiments disclosed herein is the realization that a medical device delivery system can be configured to advantageously enable a clinician to recapture, collapse, withdraw, or resheath a stent within a catheter of the delivery system after the stent has been at least partially expanded and landed in the vessel in order to allow the clinician to improve the placement of the stent within the vessel. Further, some embodiments can be configured to enable a clinician to recapture, collapse, withdraw, or resheath the stent even the entire stent has been moved out of the catheter lumen and at least partially expanded against the vessel wall. Moreover, some embodiments can be provided such that the delivery system can engage and retain any braided stent without requiring special-purpose engagement structures on the stent.

Some embodiments of the system can enable a clinician to advance, recapture, collapse, withdraw, or resheath a stent within a patient's vasculature. According to some embodiments, the system can comprise a core member for moving, either by distally advancing or proximally retracting, a stent within a body lumen. The core member can be configured to extend within a sheath, microcatheter, or tube of the delivery system. The system can comprise a core assembly that is slidably disposed within a catheter and able to secure, grip, or engage at least a portion of the stent in order to control movement, deployment, and expansion of the stent.

In some embodiments, the system can compress the stent against an inner wall of a catheter or lumen. The system can optionally comprise an engagement component, protruding member, stop member or restraint, sleeve, bumper, or variable dimension portion providing a radially-extending dimension, disposed along the core member. The engagement component can provide compressive engagement of the stent against an inner wall of the catheter or lumen.

In some embodiments, the core assembly can comprise a constraining member and a core member. The stent can extend over the core member and into a recess formed by the constraining member to engage or secure a portion of the stent. Some embodiments can be configured such that the constraining member engages a proximal portion of the stent.

Optionally, the core assembly can also comprise an engagement component, protruding member, stop member or restraint, sleeve, bumper, or variable dimension portion providing a radially-extending dimension, disposed along the core member. In such embodiments, the stent can extend over the engagement component and into the recess.

For example, the engagement component and the constraining member can collectively form a gripping mechanism that engages or secures the stent. The gripping mechanism can engage a proximal or first portion of the stent in a collapsed state. The gripping mechanism can provide a press or interference fit between the constraining member and the engagement component to inhibit expansion of the first end of the stent. The gripping mechanism can enable the stent to be withdrawn, recaptured, retracted, or resheathed into the catheter even after the stent has been moved out of the catheter lumen (i.e., the catheter has been fully withdrawn from the stent) and the stent has at least partially expanded into apposition with the vessel wall.

The gripping mechanism can enable the core assembly to exert a pushing force and a pulling force on the stent to adjust its axial position relative to the catheter. In some embodiments, the gripping mechanism can be operative to exert a distal pushing force on the stent to distally advance the stent relative to the catheter until the first portion of the stent is distally beyond the distal end of the catheter. Further, the gripping mechanism can also be operative to exert a proximal pulling force on the stent to proximally withdraw the stent into the catheter when the stent first portion is distally beyond the distal end of the catheter and the stent is at least partially expanded into apposition with a vessel wall. The gripping mechanism can be configured to exert the distal pushing force and the proximal pulling force on its own without the cooperation of other components or structures.

In some embodiments, the stent can be secured or engaged between the engagement component and a distal end of the constraining member (which can be a sheath) in order to prevent expansion of a proximal or first portion of the stent. For example, the engagement component and the constraining member can secure the stent by inducing a variable diameter in the stent between the first portion and the second portion.

In some embodiments, the assembly can be configured such that the core member has a distal section and a proximal section. The distal section of the core member can be a distal tapering section. The core member can comprise a wire. For example, the distal section of the core member can comprise a distal tip. The core member distal tip can comprise polytetrafluoroethylene (PTFE or TEFLON®).

The constraining member can have an inner lumen that is configured to receive the core member. Further, the constraining member can have a distal portion that can be spaced apart from the core member and can have a capture area in the lumen. The capture area can be defined between the distal portion of the constraining member and the core member. For example, the capture area can be defined radially between an outer surface of the core member and an inner surface of the tubular constraining member.

Further, the engagement component can be disposed along the core member at least partially distal of the capture area. In some embodiments, the engagement component can extend continuously around the core member. However, the engagement component can also extend around only a portion of the core member. The engagement component can also extend radially. Further, the engagement component can have an outer surface. In some embodiments, the engagement component can be disposed axially between the distal section and the proximal section of the core member. Furthermore, the stent can have a first portion and a second portion. The first portion can be a proximal portion that is disposed within the capture area. The second portion can be disposed distal relative to the first portion. The second portion can extend across or over an outer surface of the engagement component so that the engagement component and the constraining member cooperate to inhibit expansion of the first portion of the stent.

In some embodiments, the core member can extend within the stent lumen and distally beyond a second portion of the stent. The engagement component can be coupled to the core member and be disposed distal of the distal portion of the constraining member within the stent second portion.

The engagement component can optionally have a generally cylindrical outer surface. For example, the engagement component can comprise an annular ring or sleeve coupled to or supported on the core member. The outer surface of the engagement component can be radially offset from the outer surface of the core member. Further, the engagement component can be axially spaced apart from the distal portion of the constraining member. For example, the outer surface of the engagement component can be radially offset from the inner surface of the constraining member. Furthermore, the outer surface of the engagement component can be radially offset from the capture area is defined by the constraining member and the core member. In some embodiments, the outer surface of the engagement component can be spaced radially between the outer surface of the core member and the inner surface of the constraining member. Furthermore, the second portion of the stent can extend over or be supported on the outer surface of the engagement component.

The engagement component can be disposed at least partially distal of the distal portion of the constraining member. Further, when the assembly is oriented substantially straight, the engagement component can be configured such that it does not press the stent against the inner surface of the catheter.

The engagement component can also have an outer surface that is radially spaced apart from the inner surface of the catheter such that when the assembly is oriented substantially straight, the engagement component does not press the stent against the inner surface of the catheter. For example, the engagement component can have a generally cylindrical outer surface. Further, when the assembly is oriented substantially straight, a radial distance between the outer surface of the engagement component and the inner surface of the catheter can be sized greater than a thickness of the stent.

However, in accordance with some embodiments, the engagement component can be configured to compress the stent against an inner wall of the sheath, catheter, or tube. In such embodiments, the engagement between the engagement component and the stent can be used to move the stent within the sheath, catheter, or tube without the use of a constraining member. As noted herein, the engagement component can be fixed relative to the core member (i.e., not rotatable or translatable relative to the core member) or can be configured to rotate and/or translate relative to the core member to provide advantages such as those discussed herein.

Additionally, in some embodiments, the catheter can be provided in order to form a stent delivery system. The stent delivery system can comprise the catheter and a core assembly. The catheter can have a distal end. As noted above, the core assembly can comprise a tubular constraining member, a stent, a core member, and a radially extending engagement component.

In accordance with some embodiments, the constraining sheath can include a lumen having a cross-sectional inner profile. The engagement component can have a cross-sectional outer profile that is sized about equal to or greater than the catheter inner profile. The cross-sectional outer profile of the engagement component can be sized greater than the catheter inner profile. The stent can extend over the engagement component and into the constraining sheath such that the stent has a first diameter at the stent's first portion and a second diameter at the stent's second portion, sized greater than the first diameter. Thus, the stent can be secured between the engagement component and the sheath distal end. In accordance with some embodiments, the engagement component can be rotatably mounted on the core member, as discussed further herein. Further, the engagement component and the core member can also be formed from a continuous piece of material.

Further, a collective outer profile of the stent and the proximal member can be sized greater than the sheath inner profile. The core member can be configured to be steerable when a distal end of the stent is expanded into contact with a blood vessel by being rotatable relative to the stent and the constraining sheath. In some embodiments comprising an engagement component, the core member can also be rotatable relative to the engagement component.

The delivery of a stent in a vessel and subsequent expansion of the stent into apposition with the vessel wall can present some challenges in tortuous vessels. For example, during delivery to the treatment site, the delivery system can be configured to comprise one or more rotatable components that allow components of the system to rotate relative to each other while the delivery system traverses tortuous geometries. Such flexibility can reduce the overall pushing force required and tend to avoid "whipping" of the stent when it is unsheathed and/or expanded into the vessel.

For example, in accordance with some embodiments, the delivery system can comprise a rotatable core assembly. In such embodiments, the core member can rotate independently of the engagement component (if present) and/or the stent and the constraining member within the catheter to reduce "whipping" and also to enable steering of the core member, as discussed further herein. Such rotatability can facilitate the movement of the core assembly through a catheter of the delivery system so as to reduce the delivery force required to reach the treatment site.

Further, the rotatable core assembly can be configured to allow the core member to rotate independently of the stent being deployed in the vessel. Thus, the protruding end of the core member can be rotated without disrupting the contact between the vessel wall and the stent. Thus, the clinician can rotate a distal, protruding end of the core member to preferentially align the protruding end with the adjacent vessel geometry to avoid abrading or perforating the vessel wall while advancing the assembly.

For example, after the stent has been moved to the treatment site, the core member of the delivery system may often include a distally protruding end that may be displaced distally as the stent is expanded and released. The distal movement of the protruding end represents a hazard of potentially abrading or perforating a wall of the vessel in which the stent is being delivered. Further, when the stent is being delivered adjacent to a vessel bifurcation or a sharp turn in the vessel, the vessel geometry, such as an apex of the bifurcation, may be particularly difficult to avoid.

In some embodiments, a core assembly can be rotatable by providing an engagement component that is rotatably positioned about the core member and rotatably coupled to or mounted on the core member. In such embodiments, the core member can be rotatably coupled relative to the engagement component thereof in order to allow the core member to rotate relative to the engagement component, the constraining member, and the stent. For example, the engagement component can comprise an annular component or sleeve that is rotatably mounted on the core member.

Thus, a rotatable (and in some embodiments, steerable) stent delivery system can be provided. Embodiments of such a system can comprise a microcatheter, a core member, and a stent. The microcatheter can have a distal end configured to be inserted into a blood vessel. The core member can extend within the microcatheter. Further, the core member can have a distal portion and an intermediate portion proximal to the distal portion. The stent can extend along the intermediate portion. Further, the core member can be configured to be steerable when a distal end of the stent is expanded into contact with the vessel by being rotatable relative to the stent and the microcatheter. Accordingly, the core member can be steerable to avoid dislodging of the stent from the vessel wall and abrading or perforation of the vessel wall.

In some embodiments wherein the system comprises an engagement component, the engagement component can be positioned along the core member in the intermediate portion and be rotatably coupled to the core member. In some embodiments, the core member can comprise an arcuate tip that extends distal of the engagement component. The core member distal portion can comprise the arcuate tip, which can extend transverse to a longitudinal axis of the microcatheter. The arcuate tip can extend transverse to or bends away from a central axis of the microcatheter lumen. The microcatheter can be either as the constraining sheath or catheter discussed herein.

In some embodiments, the distal portion can comprise an assembly including the distal cover and a distal tip structure. The tip structure can be rotatably or fixedly coupled relative to the core member. Further, the distal cover can be coupled to the tip structure.

The distal tip structure can comprise at least one member or component that can be carried by the core member. In some embodiments, the at least one member can be oriented generally transverse or parallel to the core member. For example, the tip structure can comprise a coil(s), a circumferentially-extending band(s) of material, a clamp(s), and/or other structures that can pass smoothly within a vessel at the distal portion of the core member. Further, the at least one member can comprise at least one segment of the coil or other structure.

In some embodiments of a rotatable core assembly, the distal portion of the core member can comprise a distal tip structure and/or distal cover that can be rotatably coupled to the core member. Thus, a rotatable interconnection between the distal tip structure and/or distal cover and the core member can allow the core member to rotate freely of the distal tip structure and/or distal cover, thus avoiding transmission of any rotational or torsional stresses to the stent via the distal cover. For example, the distal cover can be configured to rotate about the core member. Further, the second end of the distal cover can be rotatably coupled with respect to the core member. Furthermore, the stent can be configured to rotate about the core member at least in part by virtue of the rotatable coupling of the distal cover.

In operation, after the catheter has been positioned in the blood vessel, the stent can be partially expanded into apposition with a wall of the vessel. The clinician can rotate a distalmost curvilinear tip of the core member of the delivery system. The tip can be configured to bend away from a central longitudinal axis of the core member. Thus, when rotated, the core member's curvilinear tip can rotate relative to the stent and the constraining member. Further, as noted above in some embodiments comprising an engagement component, the core member can be rotatably coupled to the engagement component. In such embodiments, when rotated, the core member's curvilinear tip can rotate relative to the stent, the engagement component, and the constraining member. Accordingly, the clinician can align the curvilinear tip with a path of the vessel to avoid abrading or perforating the vessel wall. Thereafter, the core member can be advanced distally to guide the core member along a path of the vessel. Such methods and systems can be particularly useful when the geometry of the vessel includes a bifurcation or a sharp turn in the vessel, especially to guide the tip of the core member away from an apex of a bifurcation adjacent to the treatment site.

In accordance with yet other embodiments disclosed herein, the core assembly can be configured to comprise a distal portion that enables a distal or leading end of the core assembly and stent to be lubriciously passed through a catheter while also facilitating the resheathing of the distal portion within the catheter, as desired.

In some embodiments in which the distal portion comprises a distal cover, the distal cover can be coupled to the core member and at least partially surround or cover the stent second portion. Thus, when the core assembly is slidably disposed within the catheter, the distal cover can be positioned between, for example, radially between, the stent second portion and the catheter inner wall.

In embodiments that comprise a distal cover, the distal cover can comprise a flexible material that can extend anteriorly over at least a portion of the stent in order to provide a lubricious interface between the core assembly and an inner surface of the catheter lumen.

The distal cover can be attached are coupled to the distal tip structure or core wire using a variety of attachment means. According to some embodiments, the distal cover can be coupled to the distal tip structure by virtue of forming an enclosure that encloses at least one member of the distal tip structure. For example, the distal cover can form an enclosure that encloses the tip structure, e.g., at least one coil segment, by virtue of at least partially wrapping around the segment.

The distal cover can comprise one or more elongate strips of material. For example, the distal cover can comprise a pair of a longitudinally extending elongate strips that at least partially cover or surround the second portion of the stent. In some embodiments, the distal cover comprises no more than two elongate strips of material. In some embodiments, the distal cover can be cut from a tubular member such that a plurality of elongate strips are formed and interconnected by an annular ring of material.

Further, the distal cover can be configured to allow the distal end of the stent to expand when the distal end of the stent is moved axially beyond a distal end of the catheter. In some embodiments, the distal cover can be configured to provide little or no constraining force or otherwise inhibit the expansion of the distal end of the stent.

The distal cover can be configured to flip, evert, or otherwise move from one position to another. In accordance with some embodiments, the distal cover can comprise a first end and a second end. The first end can be a free first end, and the second end can be coupled to the distal portion. The distal cover can have a first, delivery, or proximally oriented position, orientation, or configuration in which the first end extends proximally relative to the core member distal portion and at least partially covers or surrounds the stent second portion. The distal cover can be movable from the first, delivery, or proximally oriented position, orientation, or configuration, in which the free first end is located proximally relative to the second end, to a second, resheathing, everted, or distally oriented position, orientation, or configuration wherein the first end is positioned distally relative to the second end. Thus, the distal cover can enable the core assembly to be easily withdrawn or received into the catheter lumen. Further, the distal portion of the constraining member can be axially spaced apart from a distal portion of the stent in both the delivery position or configuration and the resheathing position or configuration.

In some embodiments, the distal cover can extend anteriorly relative to the attachment point of the distal cover and/or the distal tip structure while the stent is being delivered to the treatment site. For example, the distal cover can extend along at least about one third of the stent. Further, the distal cover can be everted to extend distally relative to the attachment point of the distal cover and/or the distal tip structure after the distal end of the stent has been expanded.

Various methods for operating the core assembly and the stent delivery system are also provided. Initially, in order to position the stent delivery system within a vessel of a patient, a clinician can first position a catheter in the vessel. The catheter can have a lumen that defines an axis extending between a proximal end and a distal end, such that the catheter distal end is at a treatment site. The clinician can position a core assembly within the catheter lumen. The clinician can also advance the core assembly distally within the catheter. Thereafter, various implementations of methods can be performed using one or more of the core assemblies disclosed herein.

For example, operation of an embodiment of a stent delivery system can be performed by first moving a core assembly through a catheter to a treatment site. A constraining member of the assembly can be configured to receive a portion of a stent first portion, such that the stent is secured between a distal end of the constraining member and a proximal end of an engagement component in a delivery position. The catheter can be proximally retracted relative to the core assembly until the constraining member distal end and the stent first portion are positioned distally beyond a catheter distal end while maintaining the stent first portion in the delivery position or configuration with the core member distal section extending distally relative to the stent. Further, a distal portion of the stent can be expanded into apposition with a vessel wall while maintaining the stent first portion in the delivery position.

Thus, in accordance with some embodiments, the core assembly can be proximally withdrawn into the catheter to resheath the stent within the catheter after the distal portion of the stent has already been expanded. When using a self-expanding stent, a distal portion of the stent can expand automatically when the distal portion of the stent exits the catheter. Further, in order to expand a distal portion of the stent, a distal cover, which at least partially surrounds or covers a distal portion of the stent, can be unfurled.

Additionally, in some embodiments in which the core assembly comprises the distal cover, the distal cover can extend in a proximal direction to at least partially cover a distal portion of a stent supported on the core assembly. At least a portion of the distal cover can be interposed between the stent distal portion and the inner wall. The stent distal portion can be distally advanced beyond the catheter distal end to permit expansion of the stent distal portion. The core assembly can then be withdrawn into the lumen, such that the distal cover is retracted into the lumen in an everted configuration and oriented distally from the core assembly.

Further, in some embodiments, in which the core assembly has (i) an elongate member comprising a distal end, (ii) an intermediate portion comprising a distal end positioned at the member distal end, (iii) a stent having a distal portion and being carried by the intermediate portion, and (iv) a distal cover coupled to the member distal end, the core assembly can be positioned within the lumen such that the intermediate portion distal end is positioned axially adjacent the catheter distal end with at least a portion of the distal cover extending in a space within the lumen radially between the intermediate portion distal end and the catheter distal end. The clinician can then distally advance the core assembly relative to the catheter to permit expansion of the stent distal portion. The expansion can urge the distal cover away from the intermediate portion. Finally, the clinician can proximally withdraw the core assembly into the catheter such that the intermediate portion is positioned axially adjacent to the catheter distal end with the distal cover positioned outside of the space. In some embodiments, during proximal withdrawal of the core assembly into the catheter, the distal cover can be positioned outside of the space to provide a clearance between the intermediate portion and the catheter.

Furthermore, in some embodiments, the core assembly can have (i) a distal portion, (ii) a distal cover extending from the distal portion, and (iii) a stent having a distal portion and being carried by the core assembly. The core assembly can be advanced within the catheter such that the distal cover extends proximally from the distal portion and an annular space between the distal portion and the catheter. The clinician can distally advance the core assembly relative to the catheter to permit expansion of the stent distal portion. The expansion can urge the distal cover radially away from the core assembly. Further, the core assembly can be proximally withdrawn into the catheter such that the distal cover extends distally through the annular space. In such embodiments, during proximal withdrawal of the core assembly into the catheter, the distal cover can extend distally through the annular space to provide a clearance between the catheter and an intermediate portion of the core assembly proximal to the distal cover.

Further, embodiments of the methods can further comprise advancing the core assembly distally within the catheter such that a proximal end of the stent is positioned outside of the lumen. The method can be performed to further comprise the step of releasing the stent at the treatment site within the vessel. The method can also comprise proximally withdrawing the core assembly from the lumen while maintaining the catheter distal end in place at the treatment site. Additionally, a second core assembly can be inserted into the lumen. The second core assembly can be configured to deliver a second stent at the treatment site.

In some embodiments of the methods, proximally withdrawing the core assembly can comprise everting a free first end of the distal cover from a proximally oriented position to a distally oriented position. Further, the distal cover can be coupled to the core assembly at a distal cover second end, and the first end can be positioned distally relative to the second end when the distal cover is everted.

In accordance with yet other embodiments of the methods, the distal cover can comprise a plurality of elongate flexible strips having first ends and second ends. The second ends can be coupled to the core assembly. In such embodiments, proximally withdrawing the core assembly can comprise everting the distal cover, such that the first ends are drawn together distal to the second ends.

In accordance with some embodiments, a rotatable stent delivery system is provided that can comprise a microcatheter, a core member, at least one engagement component, and a stent.

In some embodiments, the microcatheter can have a distal end configured to be inserted into a blood vessel. The core member can extend within the microcatheter. The core member can have a distal segment. The at least one engagement component can comprise a sleeve, which can be positioned about the core member distal segment and rotatably coupled to the core member. The stent can extend along the core member distal segment.

In some embodiments, a proximal end of the stent can be engaged with the constraining member distal portion and the engagement component or sleeve to restrict movement of the stent relative to the constraining member and the engagement component or sleeve while the core member is rotatable relative to the stent, the constraining member, and the engagement component or sleeve. Thus, in some embodiments, the distal portion of the core member can comprise a distal tip structure and/or distal cover that can be rotatably coupled to the core member, and the sleeve and distal cover can permit rotation of the core member relative to the stent.

Further, in some embodiments, the microcatheter can have a lumen, and the constraining sheath can have a distal portion and extend within the microcatheter lumen. The core member can extend within the microcatheter lumen. The at least one sleeve can be positioned about and rotatably coupled to the core member. Further, the stent can be self-expanding and have (i) a proximal or first portion disposed within the sheath lumen and (ii) a distal portion extending over an outer surface of the sleeve, while the core member is rotatable relative to the stent, the constraining member, and the sleeve.

The microcatheter can comprise a lumen having a central axis, and the core member distal segment can comprise an arcuate tip that extends transverse to the axis.

The core member can be rotatable or steerable to avoid (i) dislodging of the stent from the vessel wall and (ii) perforation of the vessel wall. The core member can extend within the constraining member or sheath. In some embodiments, the core member can comprise a delivery wire.

The constraining member or sheath can be disposed along the core member and a distal portion (i) spaced apart from the core member and (ii) having a capture area. The engagement component or sleeve can be positioned adjacent to a distal end of the constraining member in an engaged position. The stent can have (i) a first portion disposed within the capture area and (ii) a second portion, distal to the first portion, supported on an outer surface of the engagement component or sleeve to restrict movement of the stent relative to the engagement component or sleeve and the constraining member. Further, some embodiments, the constraining member and the sleeve can cooperate to grip the first portion or proximal end of the stent.

The system can also comprise a distal cover extending proximally from the core member distal segment and interposed between an outer surface of the stent and an inner surface of the microcatheter. The system can also comprise a distal tip attached to the core member at the distal segment thereof, and the distal cover can be attached to the distal tip. The distal tip can be rotatably coupled to the core member. The distal tip and the core member can be formed from a continuous piece of material.

The system can further comprise an actuator attached to a proximal portion of the core member, and the actuator can be configured to impart rotation the core member.

In some embodiments, the stent distal portion can be at least partially covered at the core member distal segment. The stent can have a first diameter at the first portion and a second diameter at the distal portion, sized greater than the first diameter, such that the stent is secured between the engagement component and the sheath distal portion.

The engagement component can have a cross-sectional outer profile that is sized about equal to or greater than the constraining member inner profile. In some embodiments, the engagement component can have a cross-sectional outer profile that is sized greater than the constraining member inner profile.

The system can be configured such that in a delivery position, the first portion of the stent is restricted from expansion and restricted from movement, such as longitudinal movement, relative to the engagement member and the sheath distal portion. Further, a collective outer profile of the stent and the engagement component can be sized greater than the sheath inner profile.

The core member can be rotatable relative to the stent and the microcatheter when the stent is partially expanded within the vessel. For example, the engagement component outer profile can be generally cylindrical. The engagement component can comprise a tubular structure fitted over the core member. The constraining sheath can comprise a distal portion (i) spaced apart from the core member and (ii) having a capture area. Optionally, an outer surface of the engagement component can be radially offset from the capture area. The stent can be engaged between the engagement component and the constraining sheath in a press fit to prevent expansion of the stent first portion. The stent can be engaged between the engagement component and the constraining sheath in an interference fit to prevent expansion of the stent first portion.

According to some embodiments, the stent delivery system can comprise a core member and first and second restraints for restraining movement of a stent engagement component therebetween. The core member can have a distal segment. The first and second restraints can be coupled to the core member distal segment and axially spaced apart from each other to provide an axial gap. The first and second restraints can each have an outer profile that tapers radially inwardly, in directions away from the gap. For example, the first restraint can taper in a distal direction and the second restraint can taper in a proximal direction. Further, the stent engagement component can be, for example, a stent cover component or a stent engagement or support member.

In some embodiments, the first restraint can be positioned distally of the second restraint. The first and second restraints can have different maximum outer cross-sectional profiles. For example, the first restraint can have an outer profile that is less than an outer profile of the second restraint. The first restraint can have a maximum outer diameter less than a maximum outer diameter of the second restraint. The first restraint can have a maximum outer diameter less than a maximum cross-sectional profile of the stent cover component.

In some embodiments, the stent engagement component can be at least partially disposed in the axial gap between the first and second restraints such that the component is slidably and rotatably coupled to the core member distal segment. The stent engagement component can be formed separately from the core member such that it can rotate about and slide along the core member between the restraints. The first and second restraints can have maximum outer cross-sectional profiles that are less than a maximum diameter of the stent engagement component. The system can also comprise a stent, carried by the core member, that can have an inner diameter that is greater than maximum cross-sectional profiles of the first and second restraints.

Additionally, the stent engagement component can be a stent engagement or support member that is rotatably coupled to the core member distal segment in the gap between the first and second restraints. The first and second restraints can have maximum outer cross-sectional profiles that are less than a maximum diameter of the stent engagement or support member.

In some embodiments, the stent engagement component can be a stent cover component having a first end positioned in the axial gap between the first and second restraints such that the first end is rotatably coupled to the core member distal segment. The stent cover component can have at least one second end extending from the first end. The at least one second end can be configured to at least partially surround at least a distal portion of a stent carried by the stent delivery system. The first end of the stent cover component can be formed separately from the core member such that the first end is rotatable about and slidable along the core member between the first and second restraints.

Some embodiments of the system can further comprise third and fourth restraints and a stent engagement member. The third and fourth restraints can be rotatably coupled to the core member distal segment and axially spaced apart from each other to provide a second axial gap. Another stent engagement component (e.g., a stent engagement or support member or a stent cover component) can be rotatably coupled to the core member distal segment in the second axial gap between the first and second restraints.

The stent engagement component can be formed separately from the core member such that it can rotate about and slide along the core member between the third and fourth restraints. The engagement component can also have a maximum outer diameter that is greater than maximum cross-sectional profiles of the third and fourth restraints.

In addition, the system can further comprise a stent positioned over and engaged by the stent engagement member or at least partially enclosed within the stent cover component such that the stent is freely rotatable about the core member. The stent can have an inner diameter that is greater than maximum cross-sectional profiles of the third and fourth restraints.

In some embodiments, the axial gap has an axial length of between about 0.30 mm and about 0.70 mm greater than an axial length of the stent engagement component. In some embodiments, the axial gap has an axial length of between about 0.50 mm and about 0.70 mm greater than an axial length of the stent engagement component. For example, the axial length of the axial gap can be about 0.60 mm greater than an axial length of the stent engagement component. Further, the second axial gap can have an axial length that is between about 0.30 mm and about 0.50 mm greater than an axial length of the stent engagement component. For example, the axial length of the second axial gap can be about 0.40 mm greater than the axial length of the stent engagement component.

The system can also comprise an introducer sheath having a lumen configured to receive the core member, the first and second restraints, and the stent cover component.

In some embodiments, the delivery system can comprise a first radiopaque marker and the catheter can comprise a second radiopaque marker. The first and second radiopaque markers can be longitudinally movable relative to each other and longitudinally alignable with each other such that the system achieves a pre-release position beyond which additional distal advancement of the core member permits release of a stent from the delivery system. Further, the first restraint can comprise the first radiopaque marker, and a distal portion of the catheter can comprise the second radiopaque marker. The second radiopaque marker can be positioned at the catheter distal end. The first restraint can be positioned distally of the second restraint.

Methods of operating a rotatable stent delivery system, such as one of the systems disclosed herein, can also be provided. For example, the delivery system can comprise a stent, a constraining member, a core member or wire having a central longitudinal axis, and an engagement component or sleeve that is rotatably coupled to the core wire. The stent can extend over the engagement component and be restricted from movement, such as longitudinal movement, relative to the engagement component and the constraining member. The core wire can thus be rotatable relative to the stent, the engagement component, and the constraining member.

In accordance with some aspects of methods disclosed herein, a clinician can advance a distal end of a catheter of the delivery system in a blood vessel. Further, the clinician can advance the delivery system within the catheter. The clinician can advance the core wire distally to guide the delivery system along a path of the vessel.

The clinician can also move or partially expand the stent of the delivery system into apposition with a wall of the blood vessel. The clinician can rotate the core member relative to the other components of the core assembly.

For example, the clinician can rotate a distalmost curvilinear tip relative to the stent, the engagement component, and the constraining member. The clinician can rotate the tip, for example, via the core wire or member, until the tip achieves a desired orientation relative to the blood vessel geometry. Thereafter, the clinician can continue to advance the core wire distally to guide the core wire along a path of the vessel.

In some embodiments, when the clinician rotates the tip, for example, via the core wire or member, the relative movement between the core wire and the stent can avoid dislocation of the stent from the vessel wall. Further, in some embodiments, the clinician can advance the tip toward a vessel bifurcation. Furthermore, in some embodiments, the method can be implemented wherein rotating the tip comprises directing the tip in a direction away from an apex of the bifurcation.

In accordance with some embodiments, a method of delivering a stent delivery system is also provided that can comprise: inserting the delivery system into a curved path, the delivery system comprising a catheter, a core member disposed within the catheter, first and second restraints coupled to the core member, a stent engagement component coupled to the core member between the first and second restraints, and a stent having a first portion (i) supported on the stent engagement component and (ii) extending over at least one of the first and second restraints, the first and second restraints each having a longitudinally tapered end. The core member can be caused to bend in the curved path, more than the core member could if the first and second restraints were not tapered, without causing the first and second restraints to compress the stent against an inner wall of the catheter.

In accordance with some embodiments of methods disclosed herein, the first restraint can be positioned distally of the second restraint, and the core member can be advanced until the first restraint is determined to be positioned adjacent to the distal end of the catheter. Additionally, the axial position of the core member can be held or maintained relative to the catheter, when the first restraint is determined to be positioned adjacent to the distal end of the catheter, until initial placement of the stent is determined to be correct.

Further, in some embodiments, the delivery system can comprise a first radiopaque marker and the catheter can comprise a second radiopaque marker longitudinally movable relative to the first radiopaque marker. In such embodiments, the first and second radiopaque markers can be longitudinally aligned such that the system achieves a pre-release position beyond which additional distal advancement of the core member permits release of the stent from the delivery system. Some embodiments can be configured such that the first restraint comprises the first radiopaque marker and a distal portion of the catheter comprises the second radiopaque marker. The method can then comprise observing an image of the first radiopaque marker and the second radiopaque marker as the core member is advanced relative to the catheter. Further, when the second radiopaque marker is positioned at the catheter distal end, and the first restraint can be longitudinally aligned with the catheter distal end. Further, the first and second restraints can be advanced distally of the catheter distal end such that the stent first portion is released and the stent is disengaged from the delivery system.

In some embodiments of methods disclosed herein, the stent first portion can undergo a bend of at least about 30°. Some embodiments of the methods can be implemented to cause the stent first portion to undergo the bend without causing the first and second restraints to contact an inner surface of the stent. The stent first portion can be caused to undergo a bend of at least about 45° without causing the first and second restraints to compress the stent against the inner wall of the catheter. The stent first portion can be caused to undergo the bend without causing the first and second restraints to contact an inner surface of the stent. The stent first portion can be caused to undergo a bend of at least about 60° without causing the first and second restraints to compress the stent against the inner wall of the catheter. The stent first portion can be caused to undergo a bend of at least about 90° without causing the first and second restraints to compress the stent against the inner wall of the catheter. The stent first portion can be caused to undergo a bend of at least about 110° without causing the first and second restraints to compress the stent against the inner wall of the catheter.

Methods can also be implemented such that the delivery system further comprises third and fourth restraints coupled to the core member distally of the first and second restraints. The third and fourth restraints can be spaced apart to provide a gap wherein a first end of a stent cover component is coupled to the core member. The stent first portion can extend over the first, second, and third restraints. In such embodiments, the stent first portion can be caused to undergo the bend without causing the first, second, and third restraints to compress the stent against the inner wall of the catheter. Further, the stent first portion can be caused to undergo the bend without causing the first, second, and third restraints to contact an inner surface of the stent. According to such advantageous implementations and methods, the core member and the stent can be advanced through various tortuous passageways, such as vessels within the patient or a catheter in a torturous configuration. For example, the core member and the stent can be advanced through the aortic arch without causing restraints to compress the stent against the inner wall of the catheter.

Additionally, some embodiments of methods disclosed herein can be implemented in delivery systems that comprise one or more radiopaque markers. For example, the delivery system can comprise a first radiopaque marker and the catheter can comprise a second radiopaque marker. The first and second radiopaque markers can be longitudinally movable relative to each other and longitudinally alignable with each other such that the system achieves a pre-release position beyond which additional distal advancement of the core member permits release of a stent from the delivery system. The relative movement of the radiopaque markers can signal the location and/or deployment position of the stent to the clinician. For example, the markers can signal the stent is approaching the target site. Further, the markers can signal that the stent distal end is beginning to extend beyond a distal end of the catheter. Furthermore, the markers can also signal that the stent proximal end is approaching or about to exit the catheter.

Some embodiments of the system can be configured such that the first restraint comprises a first radiopaque marker and a distal portion of the catheter comprises a second radiopaque marker. For example, the second radiopaque marker can be positioned at the catheter distal end, and the first restraint can be positioned distally of the second restraint. Accordingly, as the first radiopaque marker approaches the second radiopaque marker during distal advancement of the core assembly within the catheter, the clinician can visually determine a position of the stent or core assembly relative to a distal end of the catheter. This visual determination can provide further information to the clinician during the deployment operation. For example, the clinician can adjust or more parameters of the advancement, such as the speed or position of the system within the vasculature, or facilitate resheathing of the stent, if necessary.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 3A is a schematic side cross-sectional view of a proximal portion of the core assembly shown in FIG. 2, according to some embodiments.

FIG. 3B is a schematic side cross-sectional view of a proximal portion of the core assembly shown in FIG. 2, according to some embodiments.

FIG. 4A is a schematic side cross-sectional view of an embodiment of a core assembly.

FIG. 4B is a schematic side cross-sectional view of another embodiment of a core assembly.

FIG. 5A is a schematic side cross-sectional view of a distal portion of the core assembly shown in FIG. 2, according to some embodiments.

FIG. 5B is a schematic side cross-sectional view of another embodiment of a distal portion of the core assembly shown in FIG. 2.

DETAILED DESCRIPTION

Figure 1:
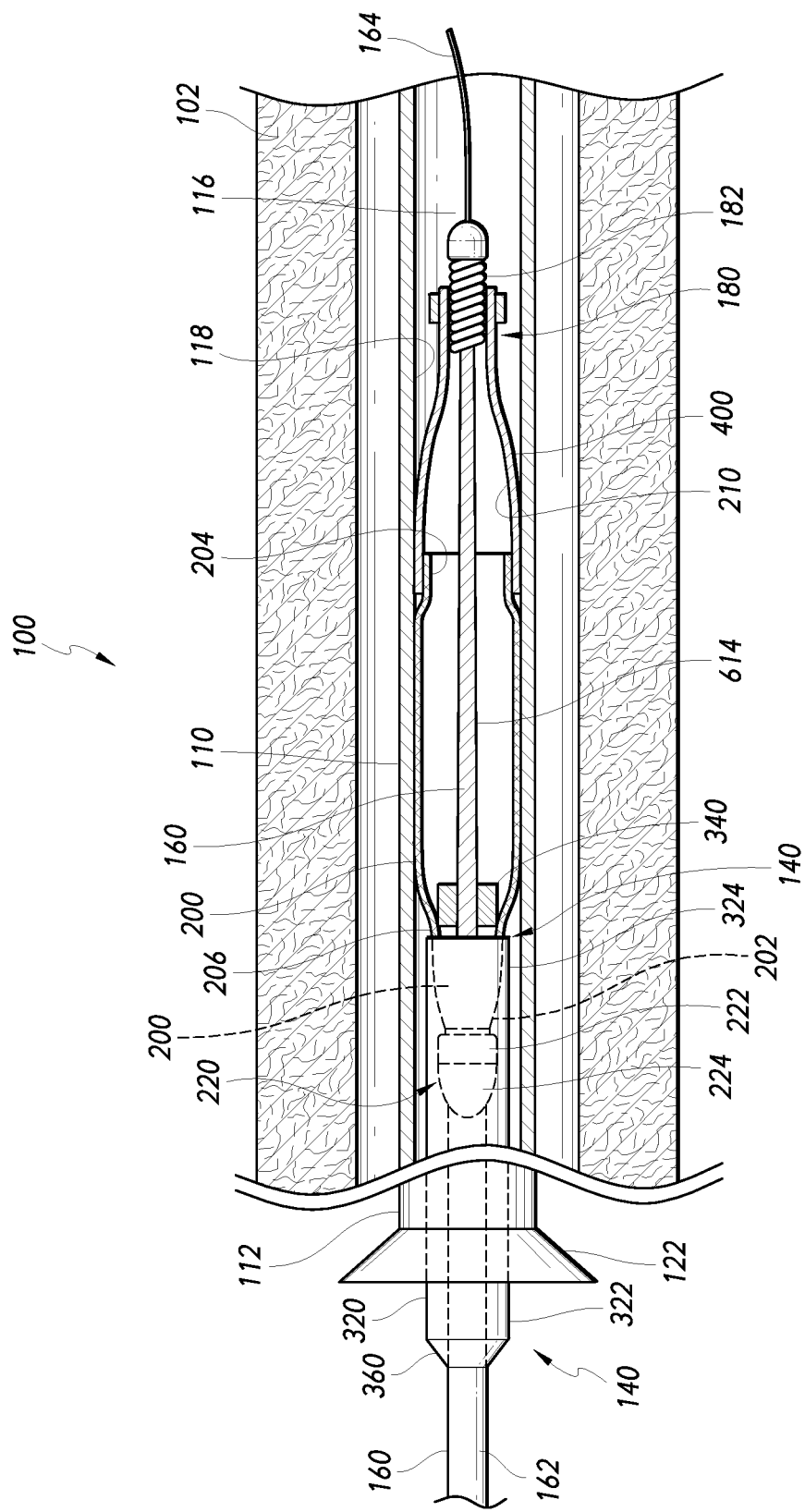
FIG. 1 is a schematic, partial cross-sectional view of a stent delivery system, according to one or more embodiments disclosed.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Described herein are various embodiments of stent delivery systems exhibiting small cross-sections which are highly flexible and can provide advantages such as allowing the clinician to recapture, collapse, withdraw, or resheath and reposition a partially expanded stent, avoid vessel abrasions or perforations during placement, place several stents (e.g., "telescoping") without removing the microcatheter, and/or avoid torsional stress and "whipping" that can occur during delivery of the stent. Various other features and advantages of embodiments are discussed and shown herein.

In some embodiments, a stent delivery system is provided that can include a core assembly and an introducer sheath and/or catheter. The core assembly can comprise a stent extending over, carried, or supported by a core member. The core member can comprise a core wire. The core assembly can be movable within the introducer sheath and/or catheter in order to deliver the stent to a predetermined treatment site, such as an aneurysm, within the vasculature of a patient. Thus, prior to delivery of the stent, the catheter can be configured to be introduced and advanced through the vasculature of the patient. The catheter can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheter or an adjacent surface with a hydrophilic material such as polyvinylpyrrolidone (PVP) or some other plastic coating. Additionally, either surface can be coated with various combinations of different materials, depending upon the desired results.

The stent can take the form of a vascular occluding device, a revascularization device and/or an embolization device. In some embodiments, the stent can be an expandable stent made of two or more filaments. The filaments can be formed of known flexible materials including shape memory materials, such as nitinol, platinum and stainless steel. In some embodiments, the filaments can be round or ovoid wire. Further, the filaments can be configured such that the stent is self-expanding. In some embodiments, the stent can be fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer.

The wire filaments can be braided into a resulting lattice-like structure. In at least one embodiment, during braiding or winding of the stent, the filaments can be braided using a 1-over-2-under-2 pattern. In other embodiments, however, other methods of braiding can be followed, without departing from the scope of the disclosure. The stent can exhibit a porosity configured to reduce haemodynamic flow into and/or induce thrombosis within, for example, an aneurysm, but simultaneously allow perfusion to an adjacent branch vessel whose ostium is crossed by a portion of the stent. As will be appreciated, the porosity of the stent can be adjusted by "packing" the stent during deployment, as known in the art. The ends of the stent can be cut to length and therefore remain free for radial expansion and contraction. The stent can exhibit a high degree of flexibility due to the materials used, the density (i.e., the porosity) of the filaments, and the fact that the ends are not secured.

Information regarding additional embodiments, features, and other details of the occlusion devices or stents, methods of use, and other components that can optionally be used or implemented in embodiments of the occlusion devices or stents described herein, can be found in Applicants' co-pending applications U.S. patent application Ser. No. 12/751,997, filed on Mar. 31, 2010; Ser. No. 12/426,560, filed on Apr. 20, 2009; Ser. No. 11/136,395, filed May 25, 2005; Ser. No. 11/420,025, filed May 24, 2006; Ser. No. 11/420,027, filed May 24, 2006; Ser. No. 12/425,604, filed Apr. 17, 2009; Ser. No. 12/896,707, filed Oct. 1, 2010; 61/483,615, filed May 6, 2011; 61/615,183, filed Mar. 23, 2012; 61/753,533, titled Methods and Apparatus for Luminal Stenting, filed on Jan. 17, 2013; Ser. No. 13/614,349, titled Methods and Apparatus for Luminal Stenting, filed on Sep. 13, 2012; and Ser. No. 13/692,021, titled Methods and Apparatus for Luminal Stenting, filed on Dec. 3, 2012; the entireties of each of which are incorporated herein by reference.

For example, in some embodiments, the occluding device or stent may be a self-expanding stent made of two or more round or ovoid wire filaments. The filaments may be formed of flexible materials including biocompatible metals or alloys, such as nitinol, platinum, platinum-tungsten, stainless steel, cobalt-chromium, or cobalt-nickel. In some embodiments, the occluding device or stent can be fabricated from a first plurality of filaments of platinum/8% tungsten and a second plurality of filaments of 35N LT (cobalt nickel alloy, which is a low titanium version of MP35N alloy). In other embodiments, one or more of the filaments can be formed of a biocompatible metal material or a biocompatible polymer.

The core member can be sufficiently flexible to allow the stent delivery system to bend and conform to the curvature of the vasculature as needed for axial movement of the stent within the vasculature. The core member can be made of a conventional guidewire material and have a solid cross-section. Alternatively, the core member can be formed from a hypotube. The material used for the core member can be any of the known guidewire materials including superelastic metals or shape memory alloys, e.g., nitinol. For example, the core member, along its length or at least at its distal end or tip, can comprise polytetrafluoroethylene (PTFE or TEFLON®). Alternatively, the core member can be formed of metals such as stainless steel.

In one or more embodiments, the stent delivery system can exhibit the same degree of flexion along its entire length. In other embodiments, however, the stent delivery system can have two or more longitudinal sections, each with differing degrees of flexion or stiffness. The different degrees of flexion for the stent delivery system can be created using different materials and/or thicknesses within different longitudinal sections of the core member. In another embodiment, the flexion of the core member can be controlled by spaced cuts (not shown) formed within the core member. These cuts can be longitudinally and/or circumferentially spaced from each other.

In some embodiments, the core assembly can secure, grasp, or engage in a proximal end of the stent to facilitate recapture, retraction, withdrawal, or resheathing of the stent into the catheter lumen. The core assembly can optionally comprise a constraining member or containment sheath. Further, the core member of the core assembly can optionally comprise at least one engagement component, protruding member, stop member or restraint, sleeve, bumper, or other variable diameter portion providing a radially-extending dimension, disposed along the length of the core member that can cooperate with the constraining member or containment sheath to secure, grasp, or engage the stent in a press, friction, or interference fit. Although some embodiments may refer to one or another type of engagement component or protruding member, various structures can be used in accordance with various implementations of these embodiments. Accordingly, in some embodiments, the constraining member and the engagement component can cooperate to form a gripping mechanism that engages a proximal or first portion of the stent. The gripping mechanism can secure or engage the first portion of the stent in a collapsed or expanded state.

For example, the containment sheath can be movable relative to the core member and configured to receive a proximal or first end of the stent. When assembled, the stent can extend over the core member with a proximal or first portion of the stent extending over a variable diameter portion of the core member and the proximal end of the stent received axially within a distal end of the containment sheath. The distal end of the containment sheath and the variable diameter portion of the core member can be axially spaced or offset from each other. The spacing of the distal end of the containment sheath and the variable diameter portion of the core member can be configured to create a press, friction or interference fit with the stent extending therebetween in order to secure, grasp, retain, or engage the first portion of the stent. Accordingly, the variable diameter portion or engagement component can cooperate with the containment sheath or constraining member to inhibit expansion of the proximal or first portion of the stent.

In some embodiments, the first portion of the stent can be secured, grasped, retained, maintained, or engaged in a collapsed or unexpanded state. Further, in some embodiments, the first portion of the stent can be secured or engaged in a manner that induces a change in diameter in the first portion of the stent. For example, the first portion of the stent can extend over or be seated on the variable diameter portion of the core member while a section of the first portion of the stent is disposed axially within the distal end of the containment sheath, which section is urged to a smaller diameter size than the diameter size of the first portion extending over or seated on the variable diameter portion of the core member. Furthermore, in some embodiments, the distal end of the containment sheath can abut a diameter-changing portion of the stent to thereby create a press, friction, or interference fit.

In some embodiments, the variable diameter portion of the core member can comprise one or more steps and/or axially extending protrusions. The variable diameter portion can be formed as an integrated structure of the core member (e.g., the core member and the variable diameter portion can be formed from a single, continuous piece of material). However, the variable diameter portion can be a separate structure that is placed onto, coupled, and/or attached to the core member. Further, in some embodiments, the variable diameter portion can be fixed relative to the core member. In other embodiments, the variable diameter portion can be rotationally and/or longitudinally movable relative to the core member.

For example, the variable diameter portion can comprise a cylindrical structure or support member that is configured to rotate about the core member, but can be fixed in a longitudinal position (or have a limited range of longitudinal movement) relative to the core member. Accordingly, in some embodiments, the variable diameter portion can facilitate rotation of the stent. Typically, during delivery of the stent to the treatment site, passing through tortuous vessels can induce a torsional stress in the delivery system and/or stent. However, in some embodiments, a rotatable (preferably cylindrical) variable diameter portion can support the stent and allow the stent to rotate about the core member, thereby alleviating torsional stresses during delivery. Such a rotatable variable diameter portion can thus reduce or eliminate the tendency of the stent to "whip" when released or expanded. "Whipping" is the rapid, rotational unwinding that sometimes occurs when the stent is released, due to the release of torsional forces that have been exerted on the stent during delivery. Further, the rotatable variable diameter portion can also allow the core assembly to exhibit greater flexibility during delivery of the stent to the treatment site.

Further, the securement or engagement of the first portion of the stent can allow a clinician to exert a distal pushing force on the stent to distally advance the stent relative to the catheter, as well as to exert a proximal pulling force on the stent to proximally withdraw or retract the stent into the catheter, even after the entire stent has been moved distally beyond a distal end of the catheter and partially expanded into apposition with a vessel wall.

Indeed, after navigating the core assembly along the length of the catheter to the treatment site within the patient, the stent can be deployed from the catheter in a variety of ways. In one embodiment, the catheter can be retracted while maintaining the position of the core member to expose the distal end of the core member and the distal end of the stent. While this is being done, the stent can be engaged in a collapsed state at least at the proximal end or portion thereof. In some embodiments, the stent can be engaged at both the proximal and distal ends or portions thereof while the catheter is being retracted.

For example, the catheter can be proximally withdrawn relative to the core assembly, thereby exposing a distal tip assembly of the core assembly. The distal portion or assembly of the core assembly can comprise a distal tip structure and/or a flexible distal cover.

The distal tip structure can comprise at least one member or component that can be carried by the core member. In some embodiments, the at least one member can be oriented generally transverse or parallel to the core member. For example, the tip structure can comprise a coil(s), a circumferentially-extending band(s) of material, a clamp(s), and/or other structures that can pass smoothly within a vessel at the distal portion of the core member. Further, the at least one member can comprise at least one segment of the coil or other structure.

In some embodiments, the distal cover can at least partially cover or surround a distal end of the stent extending over an intermediate portion of the core assembly in a first, wrapping, delivery, or pre-expansion position. For example, in this position, the core assembly can be positioned axially within the lumen of the catheter such that the distal end of the stent is positioned axially adjacent to the distal end of the catheter with at least a portion of the distal cover extending in a space within the catheter lumen radially between the distal end of the catheter and at least one of the stent or the intermediate portion of the core assembly. The distal cover can extend proximally from the distal portion or assembly and the space between the distal portion and the catheter. Further, in some embodiments, at least a portion of the distal cover can be positioned outside of a space radially between the distal tip structure of the core assembly and the catheter. Accordingly, in some embodiments, the distal cover can comprise one or more strips of a flexible and/or lubricious material that can be positioned radially in between portions of the distal end of the stent and the inner surface of the catheter to reduce sliding friction between the core assembly and the catheter.

However, as the distal end of the stent is unsheathed or moved beyond the distal end of the catheter lumen, the distal end of the stent can begin expanding and thereby urge the distal cover from the first, wrapping, delivery, or pre-expansion position or configuration to a second, unfurled, expanded, resheathing, or everted position or configuration. As the distal cover moves to the everted position or configuration, the distal end of the stent can be expanded into apposition with the vessel wall. If the stent is "landed" at the correct position within the vessel, the remainder of the stent can be unsheathed, expanded, and released into the target vessel.

However, in accordance with some embodiments, after the stent has been partially expanded and even if the stent has been fully unsheathed or moved beyond a distal end of the catheter, the stent delivery system can allow the clinician to recapture, collapse, withdraw, or resheath the stent into the catheter and later deploy, expand or unsheath the stent again from the catheter. As noted above, some embodiments allow the stent to be proximally secured, grasped, or engaged by the core assembly in order to both exert a distal pushing force on the stent and to exert a proximal pulling force on the stent. Thus, even when the stent has been fully unsheathed or moved beyond a distal end of the catheter, a proximal end of the stent can remain secured, grasped, or engaged with the core assembly to allow the stent to be retracted or withdrawn proximally into the catheter until the entire length of the stent has been resheathed into the catheter. In accordance with some embodiments, the distal cover can be retracted or withdrawn into the catheter in its second, unfurled, expanded, resheathing, or everted position or configuration.

For example, while the stent is being retracted or withdrawn back into the catheter, the distal cover can be positioned outside of the space radially between the catheter and at least one of the stent or the intermediate portion to provide a clearance therebetween and facilitate resheathing for retraction of the stent and core assembly into the catheter. Further, in some embodiments, the distal cover can be positioned in the space radially between the catheter and the distal tip structure of the core assembly. Thereafter, the catheter and/or core assembly can be repositioned axially within the vasculature at a desired location and the stent can be unsheathed, expanded, landed, and released into the vasculature if the placement location is proper.

Therefore, in accordance with some embodiments, the distal cover can facilitate resheathing of the core assembly. The resheathing of the core assembly can be done with or without the stent engaged or secured with the core assembly.

In some embodiments, the distal cover can also facilitate the retraction and withdrawal of the core assembly after the stent has been released into the vasculature. As noted, the distal cover can be withdrawn into the catheter in its second, unfurled, expanded, resheathing, or everted position or configuration. Whether or not the stent has been released into the vasculature, the entire core assembly can be withdrawn proximally into the catheter and proximally removed from the catheter. Thus, if the stent has been released into the vasculature, the core assembly can be removed from the catheter and a second core assembly can be introduced into the catheter in order to deploy a second stent at the treatment site. Such embodiments can provide significant advantages to a clinician including, for example, that the catheter need not be withdrawn and removed from the vasculature in order to deploy a first or subsequent stent to the treatment site. Accordingly then, the vasculature or need not undergo additional stress and the operation can be performed with greater speed and efficiency.

The stent delivery system can also optionally include a steerable tip mechanism or steerable tip assembly. The steerable tip mechanism can allow a clinician to avoid abrading or perforating the vessel wall during the procedure. In some embodiments, the steerable tip mechanism can comprise a steerable wire having a curvilinear distal end. For example, a core member of the core assembly can be configured to be steerable by being rotatable relative to an engagement component (if present) and the stent, the catheter, and/or other components of the stent delivery system. The core member can comprise a core wire. Further, the core wire can comprise a curved or arcuate distal section that can be rotated or reoriented, for example, by importing rotation via the core wire core member, to point the core wire in a desired direction by rotating the core wire. Accordingly, in some embodiments, the rotation of the core member relative to the stent can allow the clinician to avoid dislodging the stent from the vessel wall after initial expansion of the stent and also avoid abrasion or perforation of the blood vessel.

For example, in some embodiments, the stent can extend over an engagement component of the core member and be secured or restricted for movement relative to the engagement component and a constraining member. The engagement component can be rotatably coupled to or supported on the core member such that the core member is rotatable relative to the stent, the engagement component, and the constraining member. Accordingly, rotation of the core member can allow a clinician to adjust the position or orientation of a terminal or distal portion of the core member. Further, in some embodiments, the distal portion of the core member can be formed in an arcuate or curved configuration to enable the core member to conform to tortuous vessel geometries. For example, the distal portion of the core member can comprise a curled, curved or arcuate tip that extends distally from the core member and is oriented transverse to or bends away from a central axis of the catheter lumen.

Therefore, if the treatment site is adjacent to a tortuous vessel location (e.g., a sharp turn in the vessel) or a bifurcation, for example, the clinician can select or control the direction in which the core member extends in order to avoid abrasions or perforations of the vessel during expansion and delivery of the stent at the treatment site.

For example, prior to or during unsheathing of the stent at the treatment site, the clinician can observe the position of the distal tip assembly of the core member relative to surrounding vasculature. As the stent expands during the deployment process, it may generally foreshorten, which can require or cause the core assembly including the distal tip assembly to move distally to accommodate the shortening of the stent. This distal movement of the tip assembly to accommodate the shortening of the stent. This distal movement of the tip assembly can present an abrasion or perforation hazard, or a risk that the distal tip may engage the vessel wall in a manner that can create an abrasion or perforation in the vessel. If the clinician can identify an abrasion or perforation hazard, the clinician can evaluate whether reorienting the tip would allow it to move distally without producing an abrasion or perforation. The clinician can use a proximal actuator of the stent delivery system to rotate the core member, thereby rotating the distal tip of the core member. In some embodiments, the distal tip can have a curvilinear or arcuate configuration. In some embodiments, the arcuate or curved part of the tip can be radiopaque to enable the physician to observe via fluoroscopy or other imaging the orientation of the tip relative to the surrounding vasculature, and determine whether the tip should be rotated or reoriented into a position wherein the further distal advance of the core assembly is less likely to injure the vasculature. Such a position could be one wherein the tip points toward a lower-risk path (e.g., at a bifurcation, the gentler rather than the sharper of the turns provided at the bifurcation, or the larger rather than the smaller vessel). Thus, rotation of the distal tip can reorient the direction of the core member to avoid a bifurcation apex, a sharp turn in the vessel, or other structures of the vasculature which may represent an abrasion or perforation hazard. Thereafter, if the core member is distally advanced axially within the vasculature, a properly oriented distal tip can follow the path of the vasculature without abrading, perforating, or otherwise damaging the vessel wall.

Additionally, in some embodiments, the core assembly of the stent delivery system can be configured to comprise one or more rotatable engagement components mounted on the core member or core wire. The engagement component can be positioned axially adjacent to a distal end of a constraining member extending over the core member. In some embodiments, the engagement component can have a cross-sectional outer profile that is sized about equal to or greater than the cross-sectional inner profile of the catheter. For example, the engagement component can have a cross-sectional outer profile that is sized greater than the inner profile of the catheter.

Further, in some embodiments, the distal tip assembly or structure, e.g., including the distal cover, can be configured to rotate about the core member. For example, an end of the distal cover can be rotatably coupled with respect to the core member. Thus, the stent can be configured to rotate about the core member at least in part by virtue of the rotatable coupling of the distal cover.

As noted similarly above in other embodiments, a stent can extend over the engagement component and be engaged or secured between the engagement component and the constraining member. In some embodiments, the engagement component can extend continuously around the core member. However, the engagement component can also extend around only a portion of the core member. The stent can have a variable diameter from a first portion to a second portion thereof as the stent is engaged in a frictional and/or interference fit. The rotatable engagement component can allow the core assembly to exhibit torsional flexibility which can reduce the pushing force required to move the core assembly through the catheter the treatment site.

FIGS. 1-6 depict embodiments of a stent delivery system 100 which may be used to deliver and/or deploy a stent 200 into a hollow anatomical structure such as a blood vessel 102. The stent 200 can comprise a proximal end 202 and a distal end 204. The stent 200 can comprise a braided stent or other form of stent such as a laser-cut stent, roll-up stent etc. The stent 200 can optionally be configured to act as a "flow diverter" device for treatment of aneurysms, such as those found in blood vessels including arteries in the brain or within the cranium, or in other locations in the body such as peripheral arteries. The stent 200 can optionally be similar to any of the versions or sizes of the PIPELINE™ Embolization Device marketed by Covidien of Mansfield, Mass. USA. The stent 200 can further alternatively comprise any suitable tubular medical device and/or other features, as described herein.

Figure 2:
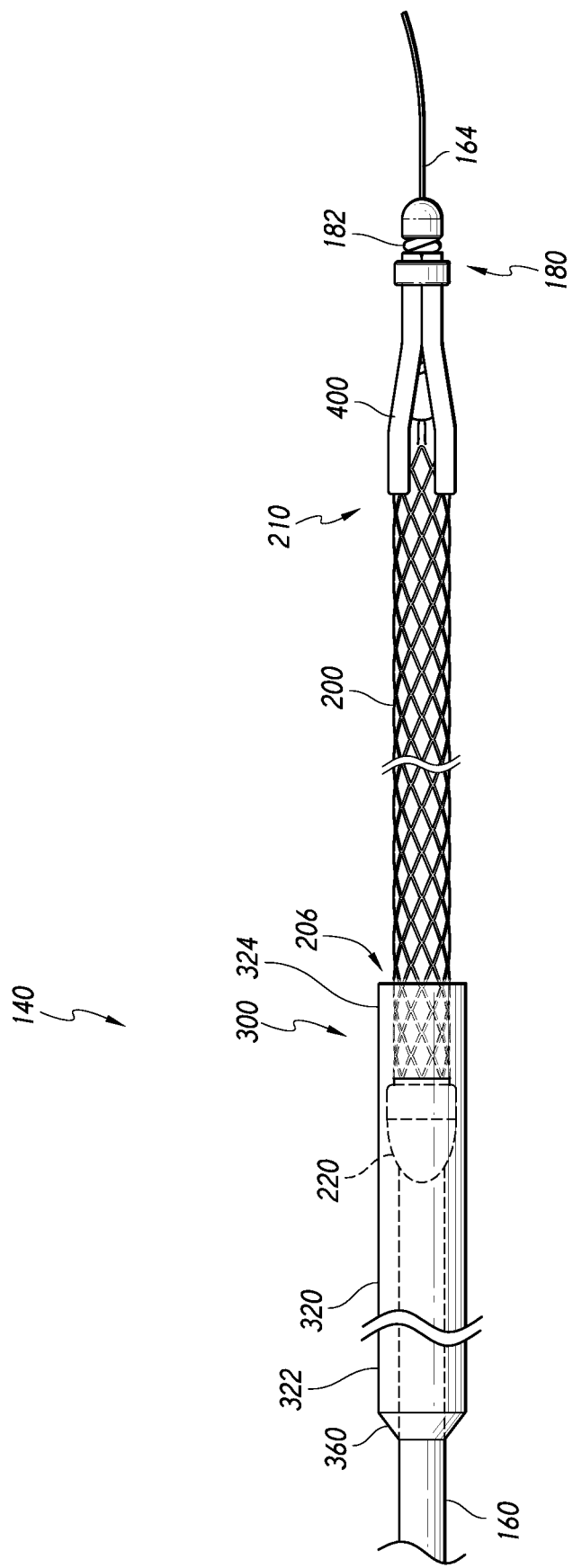
FIG. 2 is a schematic side view of a core assembly of the system shown in FIG. 1 with a stent mounted thereon, according to some embodiments.

As shown in FIG. 1, the depicted stent delivery system 100 can comprise an elongate tube or catheter 110 which slidably receives a core assembly 140 configured to carry the stent 200 through the catheter 110. FIG. 2 illustrates the core assembly 140 without depicting the catheter 110 for clarity. The depicted catheter 110, 710 (see FIGS. 1, 5, 7-8, and 12A-13) has a proximal end 112 and an opposing distal end 114, an internal lumen 116 extending from the proximal end 112 to the distal end 114, and an inner surface 118 facing the lumen 116. At the distal end 114, the catheter 110 has a distal opening 120 through which the core assembly 140 may be advanced beyond the distal end 114 in order to expand the stent 200 within the blood vessel 102. The proximal end 112 may include a catheter hub 122.

The catheter 110 can optionally comprise a microcatheter. For example, the catheter 110 can optionally comprise any of the various lengths of the MARKSMAN™ catheter available from Covidien of Mansfield, Mass. USA. The catheter 110 can optionally comprise a microcatheter having an inner diameter of about 0.030 inches or less, and/or an outer diameter of 3 French or less near the distal end 114. Instead of or in addition to these specifications, the catheter 110 can comprise a microcatheter which is configured to percutaneously access the internal carotid artery, or a location within the neurovasculature distal of the internal carotid artery, with its distal opening 120.

Information regarding additional embodiments of the catheter 110, and additional details and components that can optionally be used or implemented in the embodiments of the catheter described herein, can be found in U.S. Patent Application Publication No. US 2011/0238041 A1, published on Sep. 29, 2011, titled Variable Flexibility Catheter. The entirety of the aforementioned publication is hereby incorporated by reference herein and made a part of this specification.

The core assembly 140 can comprise a core member 160 configured to extend generally longitudinally through the lumen 116 of the catheter 110. The catheter 110 can define a generally longitudinal axis extending between a proximal end and a distal end thereof. As discussed herein, the distal end of the catheter 110 can be positioned at a treatment site within a patient. The core member 160 can comprise an intermediate portion 614 which is the portion of the core member onto or over which the stent 200 is positioned or extends when the core assembly 140 is in the pre-deployment configuration as shown in FIGS. 1-5B, 13A and 13B. The stent 200 can be fitted onto or extend over the intermediate portion of the core member 160. The core member 160 can comprise a core wire. The core member 160 can have a proximal end or section 162 and a terminal or distal end 164. In some embodiments, the distal end 164 and/or other portions of the core member 160 can be tapered such that the core member 164 becomes thinner as it extends distally.

The core member 160 can be coupled with, terminate at, or end in a distal tip. In some embodiments, the core member 160 can comprise a proximal section and a distal section. The distal section of the core member 160 can be a distal tapering section, as illustrated. The distal tapering section can have a gradual taper that continues to the distal tip of the core member 160.

The distal tip of the core member 160 can comprise a distal portion or assembly 180. In some embodiments, the distal tip assembly 180 can comprise a distal tip structure 182 and/or a distal cover 400 or stent-engaging portion. The distal tip structure 182 can comprise at least one member or component that can be carried by the core member 160. In some embodiments, the at least one member can be oriented generally transverse or parallel to the core member 160. For example, the tip structure 182 can comprise a coil(s), a circumferentially-extending band(s) of material, a clamp(s), and/or other structures that can pass smoothly within a vessel. Further, the at least one member can comprise at least one segment of a coil or other structure.

In the illustrated embodiment, the core wire can optionally be configured to extend through the distal tip assembly 180 and terminate at the distal end 164. In some embodiments, the core member 160 can be configured to transmit torque and axial/longitudinal force from the proximal end 162 of the core member 160 to the distal end 164, where the distal tip assembly 180 is disposed.

The distal end 164 of the core member 160 can be a flattened section of the core member 160. The distal end 164 can be flattened from a tapered diameter of the core member 160 to a generally rectangular cross-section having a thickness sized less than the diameter of the adjacent portion of the core member. For example, the distal end 164 can have a thickness of between about 0.0005 inches to about 0.003 inches. The distal end 164 can thus be flattened from a distal portion of the core member 160 having a diameter of between about 0.003 inches to about 0.005 inches. In some embodiments, the distal end 164 can be a flat portion having a thickness of about 0.001 inches. Additionally, the length of the flat portion of the distal end 164 can be between about 8 mm and about 15 mm. In some embodiments, the length of the flat portion of the distal end 164 can be between about 10 mm and about 12 mm. Whether in the form of the flattened wire described above, or of a distally extending tip coil, or other configuration, the distal end 164 can optionally be covered with or include radiopaque material, such as a radiopaque polymer. One suitable radiopaque polymer is a thermoplastic polyurethane (e.g., PELLETHANE™ 80A or TECOFLEX™) doped with a radiopacifier such as tungsten or barium sulfate.

As illustrated in FIGS. 1-2, some embodiments of the core member 160 can be configured with an arcuate or curved distal end 164. The distal end 164 extends distally from the core member 160 and can be oriented transverse to or bend away from a central axis of the catheter lumen 116. The distal end 164 can be curved or bent to form an angle of approximately 45 degrees with the longitudinal axis of the core member 160. The distal end 164 can be heat-set or otherwise processed to retain the arcuate/curved/angled configuration. As discussed further herein, the core member 160 can be twisted or torqued to rotate the arcuate or curved distal end 164 thereof in order to advantageously allow a clinician to carefully navigate and steer the distal tip assembly 180 and core member 160 through tortuous vessel geometry, thereby avoiding abrasion or perforation of a vessel wall.

The distal tip assembly 180 may be coupled axially adjacent to the distal end 164 of the core member 160. Moreover, the core member 160 may extend into and form a core of the distal tip assembly 180, or otherwise be connected to the distal tip assembly 180.

In some embodiments, the distal tip assembly 180 can be rotatably coupled to the distal end 164 of the core member 160. As discussed further herein, a rotatable coupling between the distal end 164 of the core member 160 and the distal tip assembly 180 can allow the core member 160 to rotate independently relative to the distal tip assembly 180 (and possibly other components of the core assembly 140). Such relative rotation can advantageously impart greater flexibility to the core assembly 140 as it is passed through the catheter 110 to the treatment site. Further, in embodiments in which the distal end 164 of the core member 160 extends distally beyond the distal tip assembly 180, such relative rotation can also advantageously allow the distal end 164 to be rotated independently of the distal tip assembly 180, which may reduce any torsional stress on the stent 200, the core assembly 140, and/or the surrounding vasculature.

However, in other embodiments, the distal tip assembly 180 can be rigidly or fixedly coupled to the distal end 164 of the core member 160 such that the distal tip assembly 180 and the core member 160 rotate as a single unit. For example, the core member 160 can be operatively coupled with the distal tip assembly 180 such that the distal tip assembly 180 is usable to radially direct or steer the core member 160 within the catheter 110 and/or a blood vessel by twisting or torquing the core member 160.

The distal tip structure 182 can be configured to comprise an atraumatic distal end face formed by a rounded solder bead, especially in embodiments in which the distal end 164 of the core member 160 does not extend distally beyond the distal tip assembly 180. Further, the distal tip structure 182 can have other atraumatic shapes designed to avoid injury to the vessel into which it may be introduced.

The core member 160 can be sufficiently flexible to allow flexure and bend as it traverses tortuous blood vessels. In some embodiments, the core member 160 can be tapered along at least part of its length or contain multiple tapering or stepped sections of different diameters or profiles, and become narrower and more flexible as it extends distally.

The core assembly 140 may also optionally include a proximal retaining member 220 located proximal of the stent 200. The proximal retaining member 220 can comprise one or more materials. For example, in some embodiments, the proximal retaining member 220 may include a marker band 222 fixed to the core member 160 via a solder bead 224 or other suitable connection. The marker band 222 may be a generally cylindrical structure made of platinum or other radiopaque material. In at least one embodiment, the proximal retaining member 220 may be arranged in the core assembly 140 such that there is a small gap, e.g., from about 0.0 mm to about 0.5 mm, axially between the band 222 of the retaining member 220 and the proximal end 202 of the stent 200.

In embodiments where the marker band 222 of the proximal retaining member 220 is made of platinum or another radiopaque material/substance visible through fluoroscopy, CAT scan, X-Ray, MRI, ultrasound technology or other imaging, a user may be able to determine the location and track the progress of the proximal end 202 of the stent 200 within the catheter 110 or blood vessel 102 by determining the location of the proximal retaining member 220.

Instead of, or in addition to, the depicted components of the proximal retaining member 220, the retaining member 220 may include a marker coil (not shown) or a coil or other sleeve (not shown) having a longitudinally oriented, distally open lumen that at least partially receives and surrounds the proximal end 202 and/or other proximal portion of the stent 200. Further, the proximal retaining member 220 can also comprise a biasing member, such as a coil spring wound around the core member 160, which can be configured to bias the stent 200 in the distal direction.

Referring now to FIG. 3A, some embodiments of the system 100 can also comprise a stent holding assembly 300 configured to releasably engage a first portion 206 of the stent 200. The stent holding assembly 300 can enable a clinician to secure, grasp, or engage the first portion 206 of the stent 200 in a manner that allows the stent to be controlled, positioned, and released at a precise, desired position within the vessel. In some embodiments, the stent holding assembly 300 can enable a clinician to push the stent distally, pull the stent proximally, unsheath or move the stent distally beyond the distal end of the catheter, and/or recapture, collapse, withdraw, or resheath the stent into the catheter after the stent has been partially expanded within the vessel.

Further, in accordance with some embodiments, the stent holding assembly 300 can be configured to accomplish such superior control using only the securement, grasping, or engagement between the stent holding assembly 300 and the first portion 206 of the stent 200. Thus, a distal portion 210 of the stent need not undergo or directly receive the pushing or pulling forces exerted by the clinician. Instead, the distal portion 210 of the stent can be guided by the forces exerted on the first portion of the stent and generally expand freely when moved outside of the catheter. As such, the clinician can carefully control the axial position of the distal portion of the stent in order to properly land the stent within the vessel and should the stent need to be repositioned, the clinician can recapture, collapse, withdraw, or resheath the stent into the catheter and attempt to land the stent again within the vessel at the desired position.

The stent holding assembly can comprise one or more components that cooperate to secure, grasp, or engage a portion of the stent 200. In some embodiments, a component attached to, coupled to, carried by, or formed on the core member 160 can cooperate with other structures of the system 100 in order to provide such superior stent control.

For example, as seen in FIGS. 2-3A, the core assembly 140 can also comprise a constraining member or outer grip member 320. The constraining member 320 can have a proximal end 322 and a distal end 324. The constraining member 320 can comprise an elongate sheath having a central lumen extending between the proximal end 322 and the distal end 324. The central lumen can be configured to receive the core member 160 therethrough.

In some embodiments, the constraining member can be a simple tube or sheath. For example, the constraining member can have an inner diameter of between about 0.015 inches and about 0.023 inches. The inner diameter can also be between about 0.017 inches and about 0.021 inches. In some embodiments, the inner diameter can be about 0.017 inches or about 0.021 inches. Further, an outer diameter of the constraining member can be between about 0.018 inches and about 0.028 inches. The outer diameter can also be between about 0.020 inches and about 0.026 inches. In some embodiments, the outer diameter can be about 0.020 inches or about 0.025 inches. The axial length of the constraining member can also be between about 150 cm and about 200 cm. Further, the constraining member can be formed from a flexible material. For example, the constraining member can be formed from material such as PTFE, polyimide, or other such polymers.

However, the constraining member can also be configured as a structural alternative to a simple tube or sheath. Such structures can include a distal end portion that is "fully" tubular coupled to a proximal portion that is made up of one or more longitudinal struts or wires, or that comprises a slotted or spiral-cut tube. In any of the disclosed constraining members, the distal end portion may comprise a coil (e.g., a metallic coil) or other form of proximally retractable sleeve suitably sized for use in the core assembly 140.

Further, the core assembly 140 can also comprise at least one engagement component, protruding member, stop member or restraint, sleeve, bumper, or variable dimension portion providing a radially-extending dimension, disposed along the core member. The engagement component can comprise a protrusion or a recess disposed along the core member 160. For example, the engagement component can comprise an protruding member, stop member or restraint, sleeve, bumper, or variable dimension portion 340. The engagement component 340 can be a radially extending component. The engagement component 340 can be disposed along the core member 160 between the distal section 164 and the proximal section 162 thereof. For example, the engagement component 340 can be disposed axially between the proximal section 162 and the distal section of the core member 160. In accordance with some embodiments, the stent holding assembly 300 can be configured such that the constraining member 320 and the engagement component 340 cooperate to secure, engage, or grip the proximal end 202 and/or first portion 206 of the stent 200. Further, the constraining member 320 can be longitudinally displaceable relative to the core member 160 and/or the engagement component 340 to release the first portion of the stent and allow it to expand within the vessel. Thus, during axial advancement or withdrawal of the stent 200 within the lumen 116 of the catheter 110 or expansion of the stent 200 within the vessel, the first portion 206 of the stent 200 can be controlled by the stent holding assembly 300.

In some embodiments, the stent holding assembly 300 can be configured such that one or more components thereof define a capture area in which at least a portion of the first portion of the stent can be secured, engaged, or grasped. The capture area can extend around at least a portion of the circumference of the core member 160. Accordingly, at least a portion of the circumference of the first portion of the stent can be secured, engaged, or grasped in the capture area.

As shown in FIG. 3A, the depicted embodiment illustrates that the constraining member 320 can comprise a tube or sheath that receives a portion of the core member 160 in a lumen of the constraining member 320. The distal end 324 of the constraining member 320 can be spaced apart from the core member 160 to define a capture area 350 therebetween. The capture area 350 in the illustrated embodiment can be formed as a generally cylindrically shaped gap configured to receive at least the proximal end 202 of the stent 200 therewithin. Accordingly, the distal end 324 of the constraining member 320 can circumferentially at least partially cover or surround at least the proximal end 202 of the stent 200 when the proximal end 202 is received axially within the capture area 350.

In some embodiments, a distal portion of the constraining member can be fitted over or extend over the proximal end of the stent. As shown in FIGS. 1-3A, proximal end 202 of the stent 200 can be positioned in the lumen of the constraining member 320; preferably the proximal end portion of the stent 200 is slightly radially compressed and lies radially adjacent to the inner wall of the constraining member 320. The engagement component 340 can hold the first portion of the stent 200 in the constraining member 320. Where the engagement component 340 is located distal of the distal end of the constraining member 320, this can be accomplished in whole or in part by engaging, securing, or gripping the stent 200 between the engagement component 340 and the rim of the distal opening of the constraining member 320. In such embodiments, the stent 200 can be engaged, secured, or gripped in a generally axial direction. Where the engagement component 340 is positioned partly or wholly within the lumen of the constraining member 320, this can be accomplished in whole or in part by gripping the stent 200 between the outer surface of the engagement component 340 and the inner surface of the constraining member 320. In such embodiments, the stent 200 can be engaged, secured, or gripped in a generally radial direction. Further, some embodiments can be provided in which the stent 200 can be engaged, secured, or gripped in a direction transverse to the radial and axial directions.

In certain embodiments, the outer surface of the engagement component 340 can be tapered such that its outer diameter increases in a distal direction, and the inner surface of the constraining member 320 may be tapered to match the taper of the engagement component 340. In those embodiments, the stent 200 may be gripped between the outer surface of the engagement component 340 and the inner surface of the constraining member 320, and/or between the engagement component 340 and the rim of the distal opening of the constraining member 320.

With reference to FIGS. 1-4B and 7-10, preferably only a relatively small portion (e.g., significantly less than half the length, or less than 25% of the length, or less than 10% of the length) of the stent 200 is positioned axially within the constraining member 320. In the delivery or in-catheter configuration shown in FIG. 1, the balance of the stent 200 extends distally and somewhat radially outward of the distal end 324 of the constraining member 320, preferably lying radially adjacent the inner surface 118 of the catheter 110 except where the distal portion 210 of the stent extends into a distal cover or distal stent covering 400 (discussed further herein). For example, the axial length of the constraining member that extends over the stent can be between about 4 mm and 15 mm. The axial length of the constraining member that extends over the stent can also be between about 6 mm and 10 mm. Further, in some embodiments, the axial length of the constraining member that extends over the stent can be about 8 mm.

Further, in the embodiment of FIG. 3A, the retaining member 220 is shown in dashed lines to illustrate that this component can optionally be included in some embodiments of the stent holding assembly 300. The securement, gripping, or engagement of the first portion 206 of the stent 200 can be accomplished with or without the use of the retaining member 220. However, in some embodiments, the retaining member 220 can provide a proximal limit to stent migration and tend to ensure that the stent 200 does not migrate proximally as the constraining member 320 is moved proximally relative to the engagement component 340 when the stent 200 is being released. The retaining member 220 can be formed integrally with the core member 160, such as being formed from a single, continuous piece of material. However, the retaining member 220 can also be formed separately from and later coupled to the core member 160. In some embodiments, the retaining member 220 can be fixed relative to the core member 160. However, the retaining member 220 can also be free to rotate and/or slide longitudinally along the core member 160.

In accordance with some embodiments, the engagement component 340 can extend in a radial direction about at least a portion of the circumference of the core member. The engagement component can have an outer surface that extends radially beyond or is spaced radially apart from an outer surface of the core member. The engagement component can be generally cylindrically shaped, oval shaped, or annularly shaped. The engagement component can be an annular ring, a cylindrical sleeve, or other such structure. However, the engagement component can also have one or more radially extending protuberances that do not extend about the entire circumference of the core member. The engagement component can also be configured to extend along at least a portion of the axial length of the intermediate portion of the core member.

The engagement component can be formed from a material that can be shrink-fitted onto the core member. The engagement component can also be configured to comprise one or more materials. For example, in some embodiments, the engagement component can formed from a material having 30% BaSO4. The engagement component can define an axial length of between about 1 mm and about 5 mm. In some embodiments, the engagement component can define an axial length of between about 2 mm and about 4 mm. Further, in some embodiments, the engagement component can define an axial length of about 2 mm. The engagement component can define an inner diameter of between about 0.005 inches and about 0.015 inches. The inner diameter can also be between about 0.009 inches and about 0.013 inches. In some embodiments, the inner diameter can be about 0.006 inches, about 0.007 inches, or about 0.011 inches. Furthermore, in some embodiments, the engagement component can define an outer diameter of between about 0.013 inches and about 0.030 inches. The outer diameter can also be between about 0.019 inches and about 0.025 inches. In some embodiments, the outer diameter can be about 0.014 inches or about 0.020 inches.

The engagement component can be formed integrally with the core member as a single, continuous piece of material. For example, the engagement component can be an enlarged portion of the core member having a diameter or profile that is sized greater than a diameter or profile of the axially adjacent portions of the core member. However, the engagement component can also be formed separately from the core member and coupled thereto. For example, in some embodiments discussed further herein, the engagement component can be rotatably coupled to the core member. Alternatively, the engagement component can also be fixedly coupled to the core member.

Figure 6:
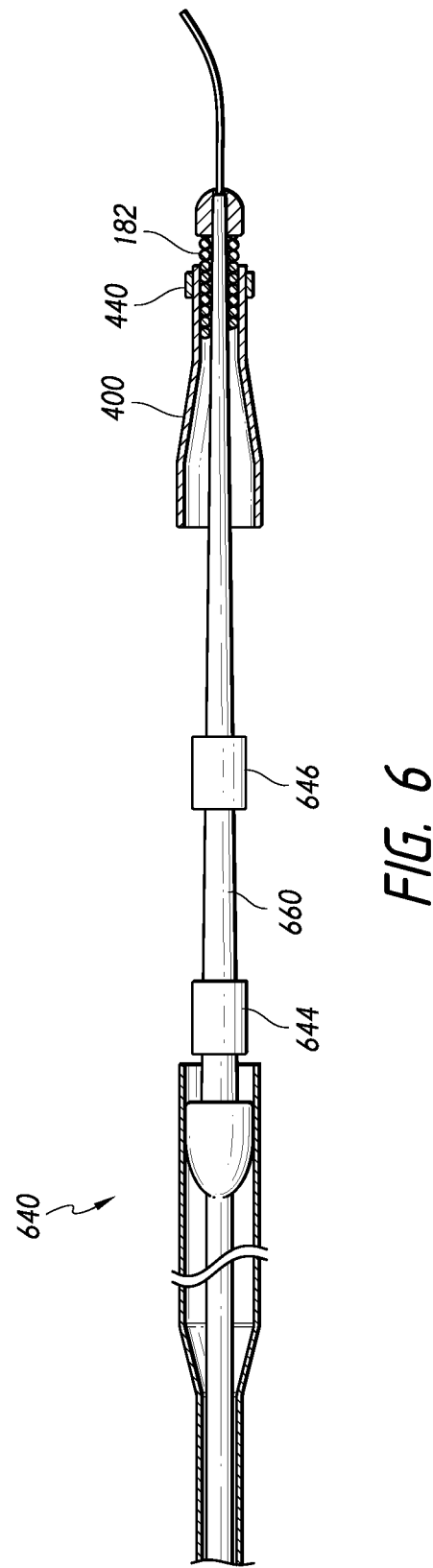
FIG. 6 is a schematic side view of the core assembly of the system of FIG. 1 wherein the stent is not shown, according to some embodiments.

Further, one or more engagement components can be used in some embodiments. For example, as shown in FIG. 6, the core assembly 640 is illustrated with a first engagement component 644 and a second engagement component 646 positioned along a core member 660. The first and second engagement components 644, 646 can be configured or operate in accordance with the configurations and functions discussed herein with respect to any of the embodiments of the engagement components. Further, the first and second engagement components 644, 646 can be configured to slide relative to each other or otherwise cooperate to support the stent on the core assembly 640.

With reference again to FIG. 3A, the engagement component 340 is shown as a radially prominent component that is integrally formed with the core member 160 from a continuous piece of material. The engagement component 340 is a generally cylindrically shaped component having a proximal section 342. The proximal section 342 can comprise a proximal wall extending in a radial direction upwardly from the core member 160, an outer circumferential surface extending generally parallel relative to a longitudinal axis of the core member 160, and/or an edge formed between the proximal wall and the outer circumferential surface. The edge can be rounded or be formed having a generally perpendicular orientation.

The engagement component 340 can alternatively comprise a component that is separate from the core member 160 (see, e.g., FIG. 1). Such an engagement component can comprise, for example, a tube of polymer or other suitable material that is attached to the core member 160 via adhesives, heat shrinking, or any other suitable technique. In one embodiment, the engagement component 340 comprises a polymeric tube which surrounds the core member 160, which passes through a lumen of the tube. One or more coils of metallic wire (such as platinum or platinum-alloy wire, not shown) can be wrapped around and welded to the core member 160, and thereby interposed between the core member and the polymeric tube to serve as a mechanical interlock therebetween. Preferably, the tube is heat shrink material such as PET that is heat-shrunk onto the outer surface of the coil(s), so that the shrunken tube adheres closely to the coil(s) and becomes securely attached to the core member 160. An engagement component 340 that can rotate about, and/or move longitudinally along, the core member 160 can be constructed in a somewhat similar manner. In this case, the underlying coil(s) can have a luminal inside diameter that is slightly larger than the outside diameter of the core member 160. The desired coil luminal inside diameter can be set by winding the coil(s) on an appropriately sized mandrel. The polymeric tube is then heat-shrunk onto the coil(s) (or otherwise joined thereto) to form the outer portion of the engagement component 340. The resulting engagement component 340 is then slid over the core member 160 to its desired position thereon, where the engagement component can rotate and/or translate with respect to the core member. Stop member(s) or restraint(s) can be formed on the core member 160 proximal and/or distal of the rotatable/translatable engagement component 340, to set boundaries for any longitudinal movement of the engagement component and allow it to rotate. Such restraint(s) can be formed in the manner described above for the fixed engagement component, with an underlying coil welded to the core member and an overlying shrink tube, but at a somewhat smaller outside diameter than the engagement component.

Figure 5C:
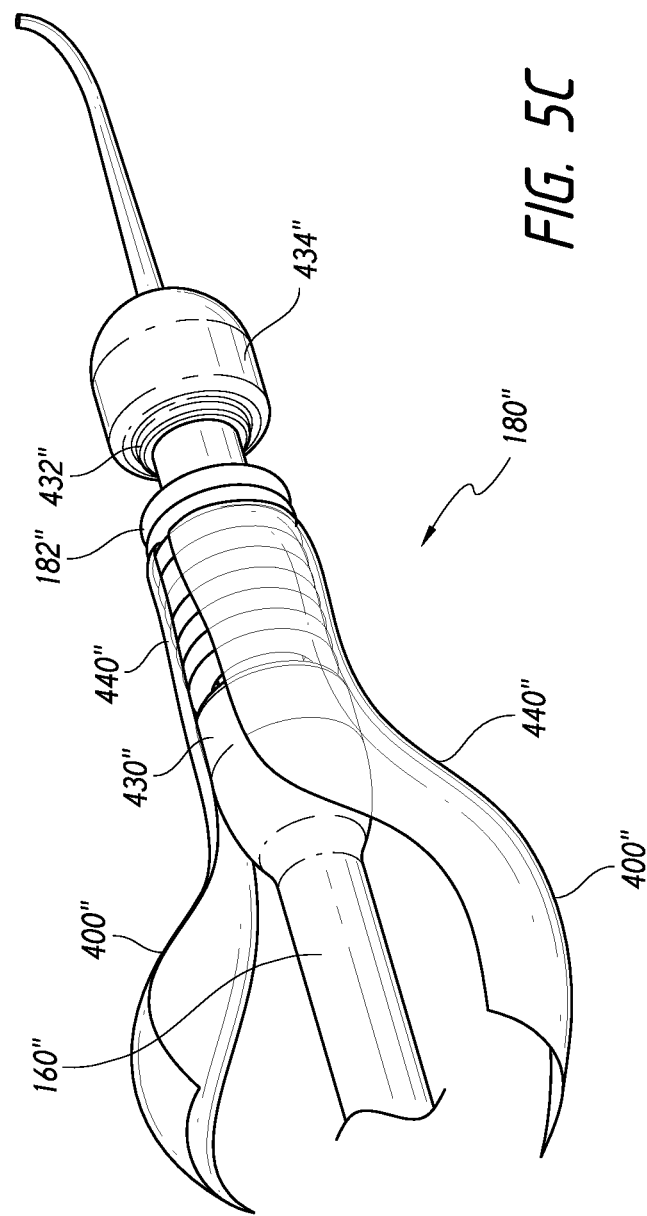
FIG. 5C is a rear perspective view of yet another embodiment of a distal portion of the core assembly shown in FIG. 2.
Figure 8:
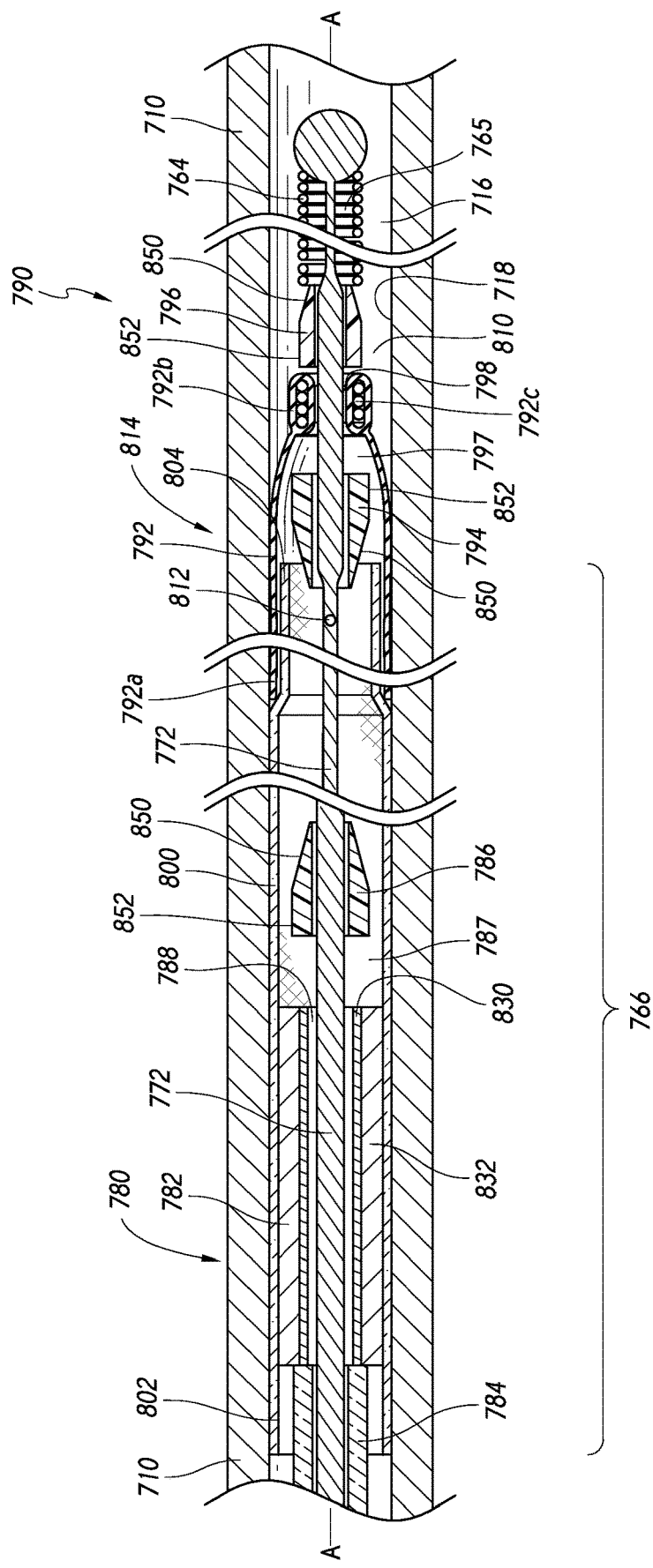
FIG. 8 is an enlarged side, cross-sectional view of the delivery system shown in FIG. 7.
Figure 9:
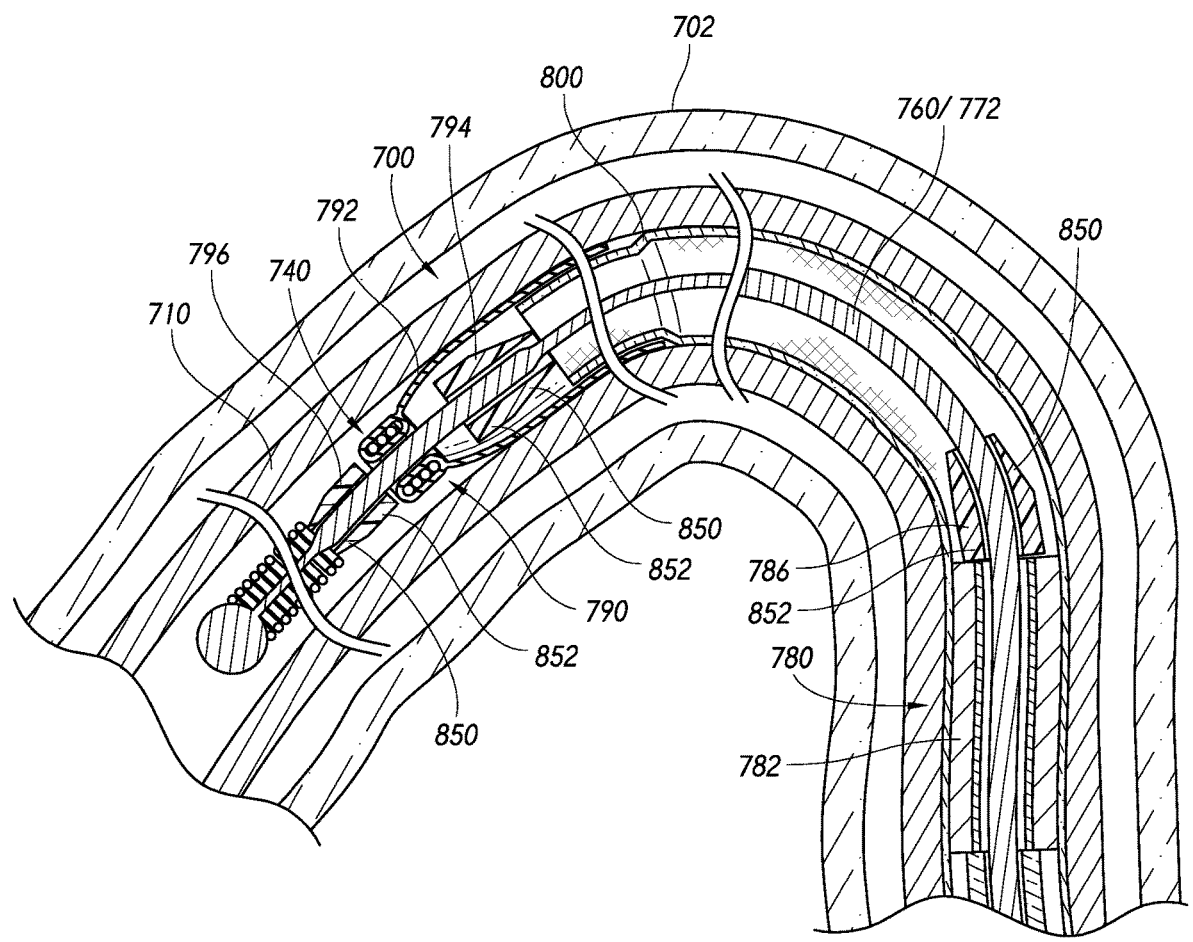
FIG. 9 is a side, cross-sectional view of a medical device delivery system being advanced through a torturous pathway, according to some embodiments.
Figure 10:
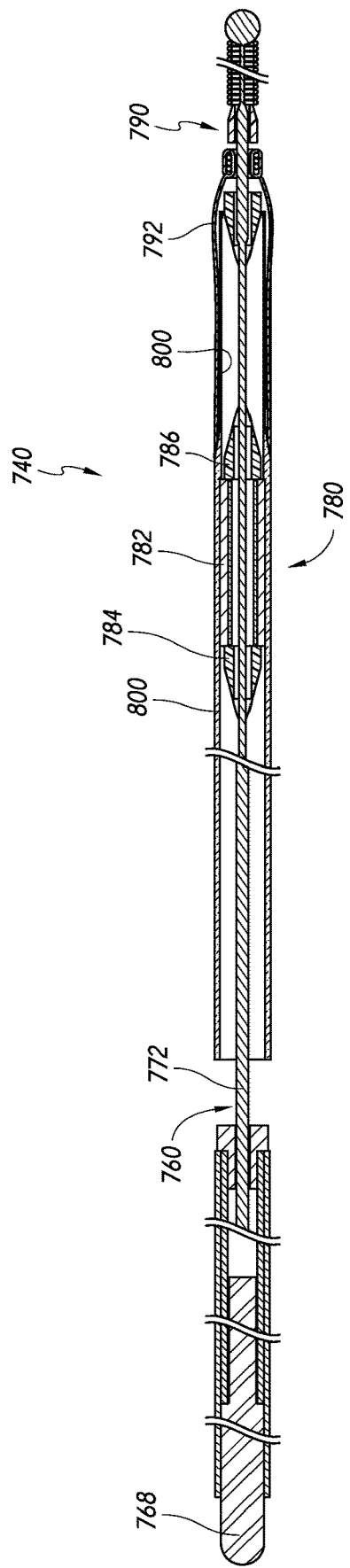
FIG. 10 is a side, cross-sectional view of another core assembly, according to some embodiments.
Figure 11:
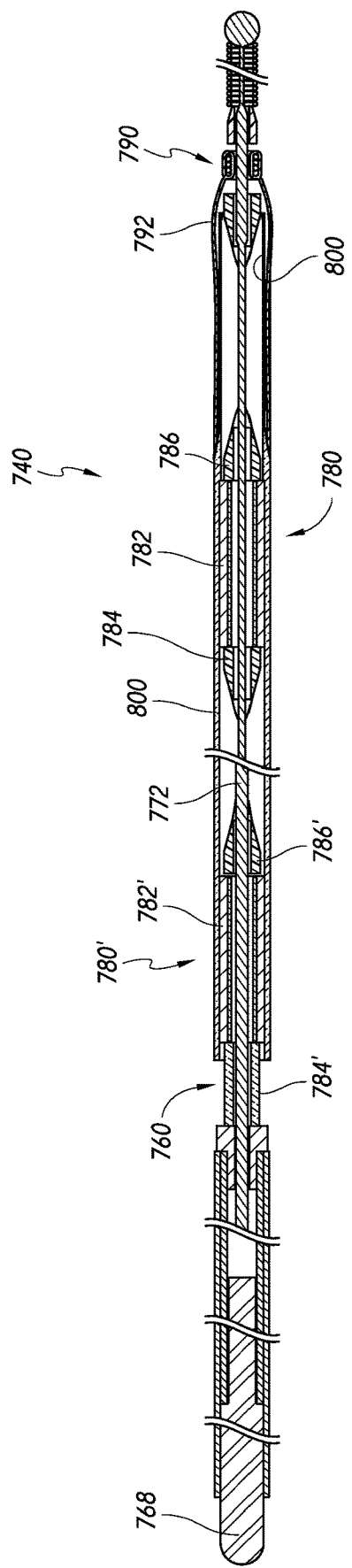
FIG. 11 is a side, cross-sectional view of yet another core assembly, according to some embodiments.

For example, FIGS. 5C and 7-11 illustrate embodiments of a system having at least one rotatable component coupled to the core member between restraints that have a tapered configuration. FIG. 5C illustrates a distal cover that is rotatably attached to a core member and positioned in a gap between restraints. FIGS. 10-11 illustrate additional embodiments in which at least one engagement component is rotatably coupled to the core member and positioned within a gap between adjacent restraints.

As illustrated in FIG. 3A, the first portion 206 of the stent 200 can extend over the engagement component 340 and the proximal end 202 of the stent can extend into the capture area 350 formed radially between the constraining member 320 and the core member 160. In this embodiment, these components cooperate to form the stent holding assembly 300, which can secure, engage, or grip the proximal end 202 and/or first portion 206 of the stent 200. Thus, during axial advancement or withdrawal of the stent 200 within the lumen 116 of the catheter 110 or during expansion of the stent 200 within the vessel, the first portion 206 of the stent 200 can be controlled by the stent holding assembly 300.

In particular, the engagement component 340 and the constraining member 320 can cooperate to engage, secure, or grasp the stent 200 in a press fit, an interference fit, or a frictional fit, as illustrated in FIGS. 3A-4B. The presence of the engagement component 340 can create a slight increase in the diameter of the stent 200 axially adjacent to the distal end 324 of the constraining member 320. Thus, the diameter of the proximal end 202 of the stent 200 within the capture area 350 can become smaller than the diameter of the stent 200 extending over the engagement component 340. Instead of or in addition to these conditions, the stent 200 can be in frictional contact with a distal inner surface 331 and/or edge 332 of the sidewall of the constraining member 320 and the proximal section 342 of the engagement component 340, thereby securing, engaging, or grasping the stent 200 therebetween.

Further, in some embodiments, the engagement component 340 can have an outer profile or diameter that is sized about equal to or greater than an inner profile or inner diameter of the lumen of the constraining member 320. The relative sizing of the profiles of the engagement component 340 and the constraining member 320 can be configured such that the engagement component 340 can be positioned axially adjacent to the constraining member 320 in order to "pinch," secure, grasp, or engage the first portion 206 of the stent 200 in a press or interference fit. The outer profile of the engagement component 340 can also be configured to be sized less than the inner profile of the lumen of the constraining member 320 if the stent thickness is sufficient to create an interference or otherwise restrict or slow movement of the engagement component 340 into or through the lumen of the constraining member 320. For example, a collective outer profile of the stent 200 and the engagement component 340 can be sized greater than the inner profile of the lumen of the constraining member 320. In some embodiments, the collective outer profile can be an outside diameter calculated by adding the outside diameter of the engagement component 340 and two times the thickness of the stent 200. However, in other embodiments the outer and inner profiles (which can be measured as a size or shape of a cross section of the corresponding component(s)) can be noncircular, comprise one or more radial protrusions, or otherwise comprise shapes that are other than circular or rounded.

Additionally, although the embodiment illustrated in FIG. 3A illustrates that the stent 200 can be secured, grasped, or engaged without having the engagement component 340 enter the lumen of the constraining member 320, in some embodiments the engagement component 340 extends into or is received at least partially in the lumen of the constraining member 320.

FIG. 3B illustrates an alternative embodiment of an stent holding assembly. As noted herein, the configuration of the core member, stop member or restraint, and retaining member can be varied in accordance with several embodiments. FIG. 3B illustrates a stent holding assembly 300' in which a stop member or restraint is formed as a recess 170 within a body of a core member 160'. The recess 170 can extend circumferentially around the core member 160' to provide a capture area 350' configured to receive at least a portion of the proximal end 202' of the stent 200'. Alternatively, the recess 170 can comprise one or more indentations into which a portion of the first portion 206' of the stent 200' can be received.

Thus, in the illustrated embodiment of FIG. 3B, the core member 160' can have a generally constant diameter (or a tapering diameter) and the recess 170 can be configured to receive at least a portion of a first portion of the stent 200'. The diameter of the core member 160' can be sized larger along an engagement component section 340' than along a proximal section that extends within a lumen of a constraining member 320'. However, the relative diameters of the sections of the core member 160' can be varied and configured in relation to the inner diameter or inner profile of the constraining member 320', as discussed similarly above with respect to FIG. 3A. As with the embodiments discussed above, the stent holding assembly 300' can cooperatively engage, secure, or grasp a first portion 206' of the stent 200' in order to provide superior control of the stent 200' during the operation.

Referring again to FIG. 2, embodiments of the system 100 can be configured such that the constraining member 320 can be removably coupled relative to the core member 160 via a removable, disengageable or breakable coupling 360 (or otherwise selectively longitudinally moveable, adjustable or retractable relative to the core member 160). The coupling 360 is located preferably near the proximal end 162 of the core member 160, or at another location on the core member that is accessible to the clinician outside of the patient's body, proximal of the hub 122 or other proximal end portion of the catheter 110. The constraining member 320 can extend distally from a proximal end 322 thereof at the coupling 360 to a distal end 324 that is located slightly proximal of (or overlying) the engagement component 340.

A longitudinal or axial position of the constraining member 320 relative to the core member 160 can be maintained or modified by means of the coupling 360. The coupling 360 can be located at a proximal location that is outside of a body lumen such that a clinician can actuate the coupling 360 to either maintain or change the relative axial positioning of the constraining member 320 relative to the core member 160. Accordingly, in some embodiments, a clinician can disengage or break a bond between the coupling 360 and the constraining member 320 in order to move the distal end 324 of the constraining member 320 relative to the core member 160. The clinician can therefore maintain an engagement, securement, or grasp of the stent using the stent holding assembly until the stent is positioned at a desired location at the treatment site. Once the stent is in the desired location and properly landed, the clinician can thereafter disengage and release the stent by actuating the coupling 360 to proximally withdraw the constraining member 320 relative to the core member 160 (or to enable the subsequent proximal withdrawal of the constraining member).

Further, in some embodiments, the coupling 360 and the constraining member 320 can be configured with one or more stop points along a range of longitudinal movement of the constraining member 320 relative to the core member 160. Such stop points can control the relative axial movement between the constraining member 320 and the core member 160, causing the constraining member to stop at one or more desired locations. For example, a first stop point can be provided wherein the constraining member 320 is in an engaged position (e.g., wherein the first portion of the stent is gripped by the stent holding assembly 300). The first stop point may indicate tactilely to the clinician that the constraining member 320 is positioned to grip the first portion of the stent. Instead of or in addition to the first stop point, a second stop point can be provided that tactilely signals to the clinician that the constraining member 320 has been proximally retracted relative to the core member 160 and/or stop member by a distance that is sufficient to ensure that the stent has been be released from the stent holding assembly.

The embodiments disclosed herein provide useful advantages. In addition to those discussed herein, the stent holding assembly can provide a system with superior flexibility and therefore lower the delivery force necessary to advance the system to the treatment site. To some extent, the stent holding assembly retains a portion of the stent in a collapsed configuration which will tend to lessen the amount of frictional engagement between the stent and the inner surface of the catheter, further decreasing the delivery force required.

Moreover, as discussed further herein, some embodiments can provide for a delivery system in which the distal end of the stent automatically expands upon exiting the distal end of the catheter, thereby eliminating the need for structure that controls the expansion characteristics of the distal end of the stent. For example, some embodiments disclosed herein would not require a distal cover that would have to be rotated or otherwise moved to disengage from the distal end of the stent.

Furthermore, embodiments of the stent holding structure can enable a clinician to recapture, collapse, withdraw, or resheath the stent to within the catheter after partial expansion of the stent. Even in situations where the entire stent has exited the catheter lumen, some embodiments of the stent holding structure disclosed herein can enable the clinician to recapture, collapse, withdraw, or resheath the first portion of the stent and therefore the entire stent into the catheter lumen so that the core assembly can be entirely withdrawn or to allow the stent to be repositioned and landed again at a desired location at the treatment site.

As noted above, the engagement component of the core assembly can be formed integrally with the core member as a single, continuous piece of material or formed separately from the core member and coupled thereto. In some embodiments, the engagement component can be rotatably coupled to the core member.

For example, referring to FIGS. 4A-B, alternative embodiments of the engagement component are shown. As shown in FIG. 4A, similarly to FIG. 3A, core assembly 500 comprises a constraining member 502, a distal cover 504, an engagement component 506, a core member 508, and a stent 510. The engagement component 506 can be formed from a single, continuous piece of material with the core member 508, as discussed above with respect to some embodiments.

However, FIG. 4B illustrates another core assembly 540 that comprises a constraining member 542, a distal cover 544, an engagement component 546, and a core member 548. The engagement component 546 is formed separately from the core member 548. The engagement component 546 can optionally be configured to rotate with respect to the core member 548. Accordingly, in the core assembly 540, the core member 548 can rotate freely within the constraining member 542, the engagement component 546, and the stent 550. In some such embodiments, a distal tip assembly 552 of the core assembly 540 can be rotatably coupled relative to the core member 548, which can allow the core member 548 to also rotate freely relative to the distal tip assembly 552 instead of or in addition to the engagement component 546 and stent 550.

In embodiments using a rotatable engagement component, the core assembly can exhibit improved flexibility and also reduce torsional stress on the stent mounted thereon. Accordingly, while the core assembly is being delivered to the treatment site, the rotational freedom of the core member can allow the core member to adjust as it traverses tortuous pathways without transferring a torque to the stent. This enhanced rotatability can reduce "whipping." Further, the improved flexibility of the core assembly can also reduce the required delivery force.

Additionally, in some embodiments, the rotatable engagement component can be rotatably coupled relative to the core member while the distal tip assembly is fixedly coupled relative to the core member such that the distal tip assembly and the core member rotate as a unit. In such embodiments, the rotatability of the engagement component can be indirectly affected via the contact of the stent with the distal tip assembly and the engagement component. Although the stent may not be rotatably fixed relative to the distal tip assembly, the interaction between the distal tip assembly and the stent may create some resistance to rotation of the stent relative to the core member that would otherwise be freely permitted at the interconnection of the engagement component and the core member. However, once the distal tip assembly exits the catheter and the distal end of the stent is allowed to expand, the core member can freely rotate relative to the engagement component and the stent.

In accordance with aspects of some embodiments, the engagement component can also be configured to slide longitudinally relative to the core member, instead of or in addition to any rotational capability. For example, the engagement component and the core member can be configured such that the core member comprises one or more protrusions or limits against which the engagement component can abut to limit the longitudinal movement (proximal or distal) of the engagement component.

The engagement component preferably comprises a relatively soft or compressible cylindrical member, and can be formed from a suitable polymer or elastomer. In some embodiments, the outside diameter of the engagement component is preferably sufficiently small relative to the inside diameter of the catheter to inhibit the engagement component from gripping or urging the stent against the inner wall of the catheter and thereby generating significant friction between the stent and catheter. For example, as illustrated in FIG. 1, the engagement component 340 can leave sufficient radial space between the outer surface of the engagement component 340 and an inner surface or wall 118 of the catheter 110 to allow the stent wall to move radially between the engagement component 340 and catheter inner surface 118 when otherwise unconstrained. Alternatively, the engagement component 340 may be sized and configured to grip the stent 200 against the inner surface 118 of the catheter 110.

In the depicted core assembly 140, the constraining member 320 and the engagement component 340 can grip the stent 200 to facilitate delivery of the stent 200 through the lumen 116 of the catheter 110, and resheathing of the stent 200 when partially expanded, while completely or substantially isolating the catheter 110 from the grip forces involved in gripping the stent 200 by the core assembly 140. In this manner, the core assembly 140 may securely grip the proximal end of the stent 200—securely enough even to facilitate resheathing—without generating high radial friction forces between the stent 200 and the inner surface 118 of the catheter 110 that can impede advancement of the stent through the catheter 110. Instead, only relatively light radial frictional forces may exist between the stent 200 and the catheter 110, generated by the stent self-expanding against the inner surface 118, that do not significantly impede axial advancement of the stent 200 within the lumen 116 of the catheter 110.

It may also be observed that the stent delivery system 100 can grip the stent 200 radially and/or axially between components that do not (or need not) move with respect to each other during axial movement of the stent within the lumen 116 of the catheter 110, thereby reducing the friction that may arise between two components (the core assembly 140 and the catheter 110) that can move with respect to each other by a significant distance during delivery of the stent 200. The catheter 110 may remain relatively stationary within the patient's vasculature while the core assembly 140 and stent 200 are advanced to and/or through the distal end of the catheter 110. During this advancement, the constraining member 320 and the engagement component 340 may remain stationary with respect to each other, and either one or both remain stationary with respect to the stent 200.

Structures other than the herein-described embodiments of the constraining member 320 and the engagement component 340 may be used in the core assembly 140 to move the stent 200 along the catheter 110. For example, the constraining member 320 and the engagement component 340 may be omitted and the proximal bumper 220 employed for that purpose. Instead of, or in addition to, the bumper 220, additional pads or bumpers may be mounted on the core member 160, underlying the stent 200 and configured to cooperate with the radially adjacent portions of the catheter sidewall to grip the stent 200 and facilitate movement along the catheter 110.

In accordance with some embodiments, the distal tip assembly of the core assembly can comprise a distal cover configured to reduce friction between the stent (e.g., the distal portion or distal end thereof) and the inner surface of the catheter. The distal tip assembly can be configured to comprise either or both the distal tip structure and the distal cover.

Some embodiments can be provided in which the distal cover provides a restrictive force that aids in maintaining the distal portion of the stent in a collapsed configuration until released by the clinician. However, the distal cover of other embodiments disclosed herein does not on its own provide a restraining force to maintain the stent in a collapsed diameter.

For example, the distal cover can be configured as a lubricious, flexible structure having a free first end or section that can extend over at least a portion of the stent and/or intermediate portion of the core assembly and a fixed second end or section that can be coupled to the distal tip structure and/or the core member at an attachment point. The second section may be coupled directly to the core member or indirectly to the core member, for example by being coupled to the distal tip structure. The distal cover can have a first or delivery position, configuration, or orientation (see, e.g., FIGS. 1, 2, 4A, 4B, 5A, 5B, 6, 13A, 13B) in which the distal cover can extend proximally relative to the distal tip structure or the attachment point and at least partially surround or cover a distal portion of the stent. Further, the distal cover can be movable from the first or delivery orientation to a second or resheathing position, configuration, or orientation (see, e.g., FIGS. 12B-12C, 13-17) in which the distal cover can be everted such that the first end of the distal cover is positioned distally relative to the second end of the distal cover to enable the resheathing of the core assembly 140, either with the stent 200 held by the stent holding assembly 300, or without the stent.

FIGS. 5A and 5B depict embodiments of the distal cover 400. The embodiments of FIGS. 5A and 5B can be similar to each other in structure, function and method of use, except for the manner in which the cover 400 is attached to the core assembly 140. Accordingly, in the discussion herein of the distal cover 400/400', any mention of a component having a reference numeral used in FIG. 5A (e.g. 420) should be understood to include the corresponding "prime" reference numeral used in FIG. 5B (e.g. 420'), and to apply with equal force to the component so designated in FIG. 5B, and vice versa.

Referring to FIGS. 5A-5B, the core assembly 140 may include the distal cover 400 which, as noted above, can be configured to reduce radial friction between the stent 200 (e.g., the distal portion 210 or distal end 204 thereof) and the inner surface 118 of the catheter 110. The distal cover 400 may include a free first section or end 420 and a fixed second section or end 440. As illustrated, the second section 440 is coupled indirectly to the core member 160 via the distal tip structure 182, which is discussed further below.

Further, as shown in FIGS. 5A-5B, at least a portion of the distal cover 400 can at least partially extend or be interposed radially between the distal portion 210 of the stent 200 and the inner surface 118 of the catheter 110 in the first position, configuration, or orientation. In the first orientation, the first section 420 of the distal cover 400 can extend from the second section 440 in a proximal direction to a point where the first section is interposed between the distal portion 210 of the stent 200 and the inner surface 118 of the catheter 110. In this orientation, the first section of the distal cover can take on a "proximally oriented" position or configuration.

Figure 12A:
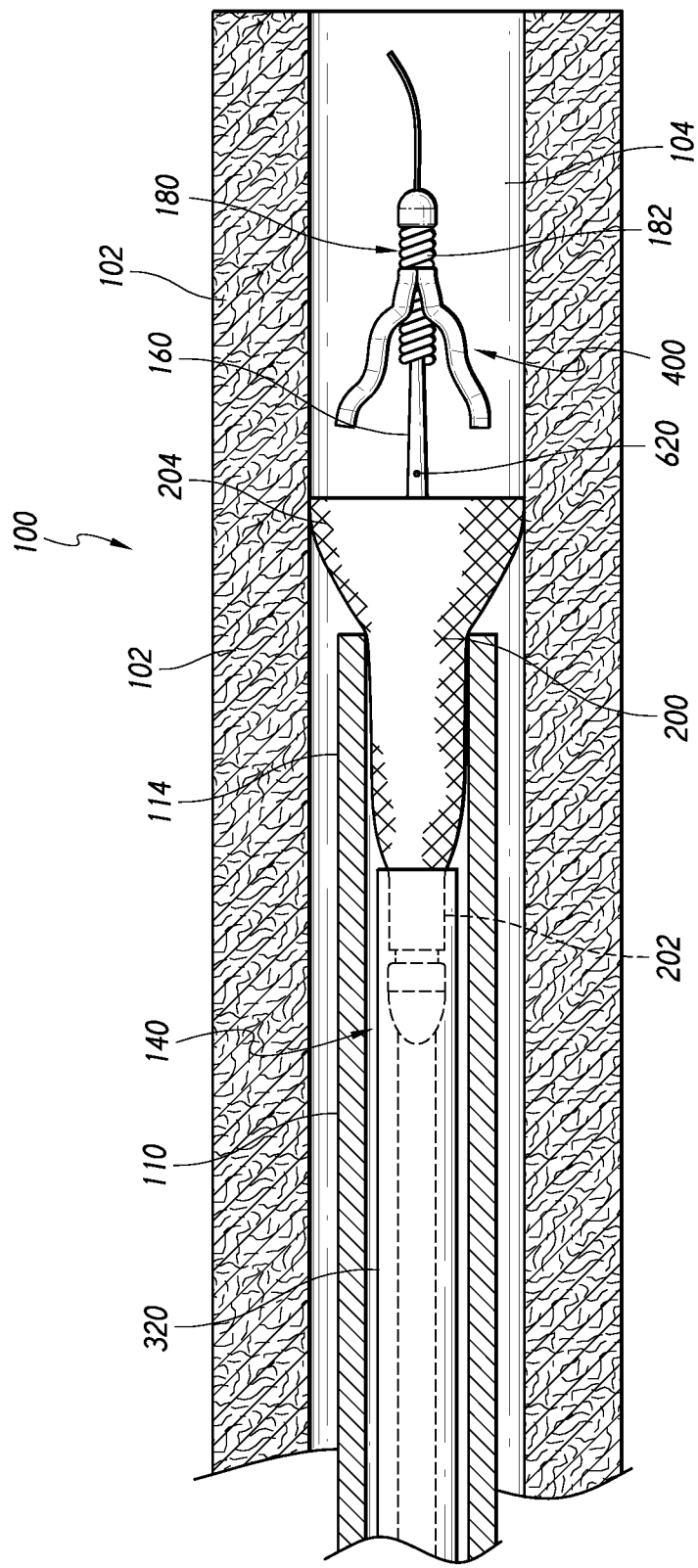
FIG. 12A is a schematic, partial cross-sectional view of the system of FIG. 1, in which a stent has been initially expanded against a vessel wall and a distal cover of the system is disengaged, according to some embodiments.
Figure 12B:
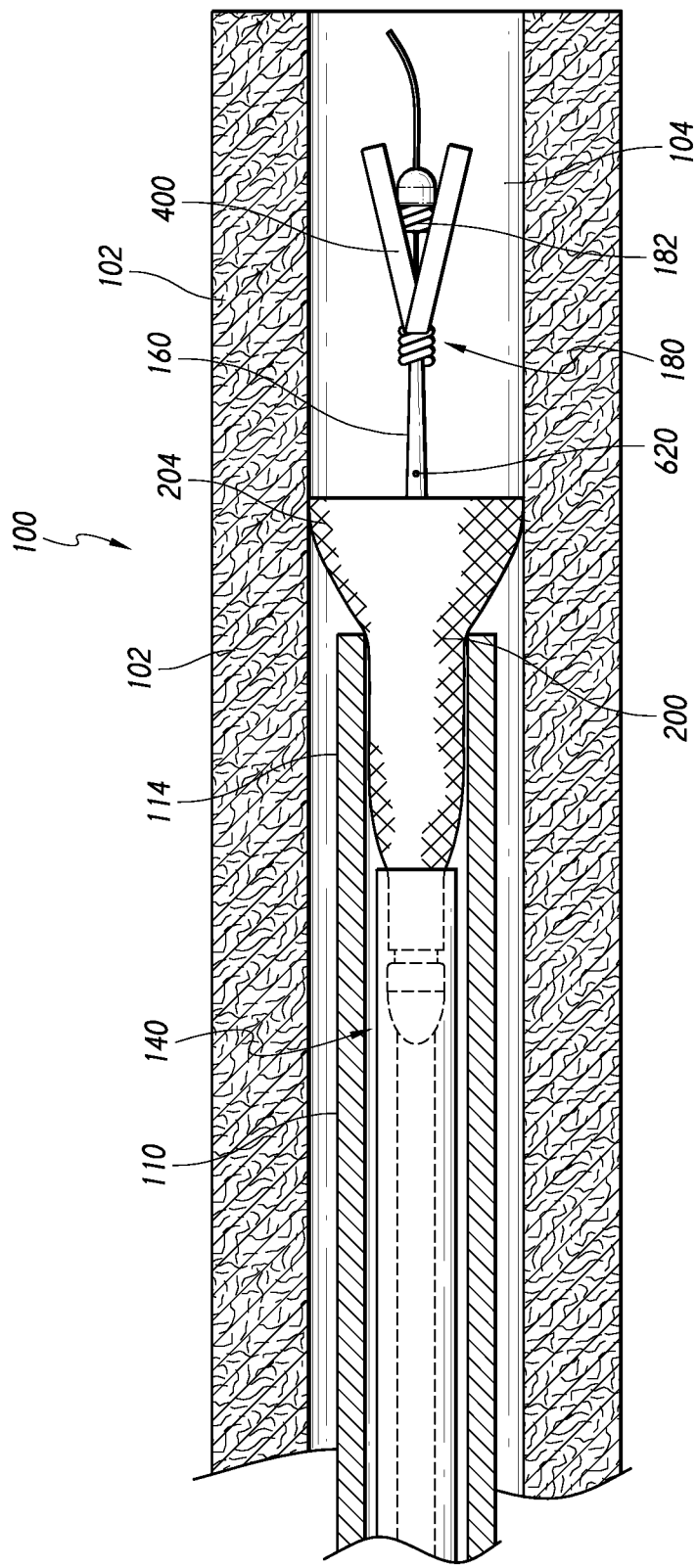
FIG. 12B is a schematic, partial cross-sectional view of the system of FIG. 1, in which the distal cover has migrated to an everted position, according to some embodiments.
Figure 12C:
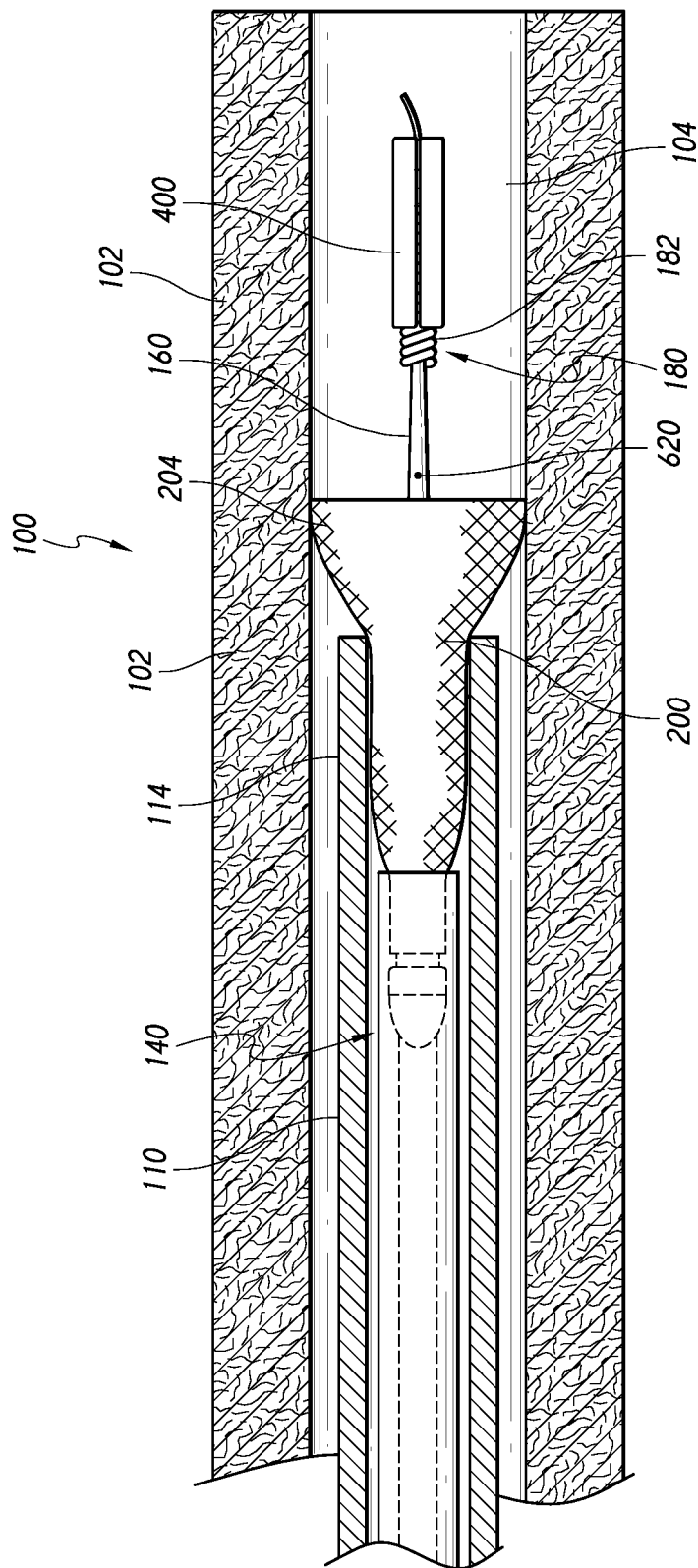
FIG. 12C is a schematic, partial cross-sectional view of the system of FIG. 1, in which the distal cover has migrated to another everted position, according to some embodiments.

The core assembly 140 shown in FIGS. 5A-5B can operate as illustrated in FIGS. 12A-12C. Referring to FIGS. 12A-12C, the core assembly 140 can be distally advanced until the distal portion 210 of the stent 200 is positioned distally beyond the distal end 114 of the catheter 110 to permit expansion of the distal portion 210 of the stent 200 into a lumen 104 of the blood vessel 102. As the distal portion 210 of the stent 200 expands, it can cause the distal cover 400 to be opened or moved from the first orientation. Because the stent 200 can foreshorten as it expands, the stent 200 can withdraw from engagement with the distal cover 400, as shown in FIG. 12A.

Figure 15:
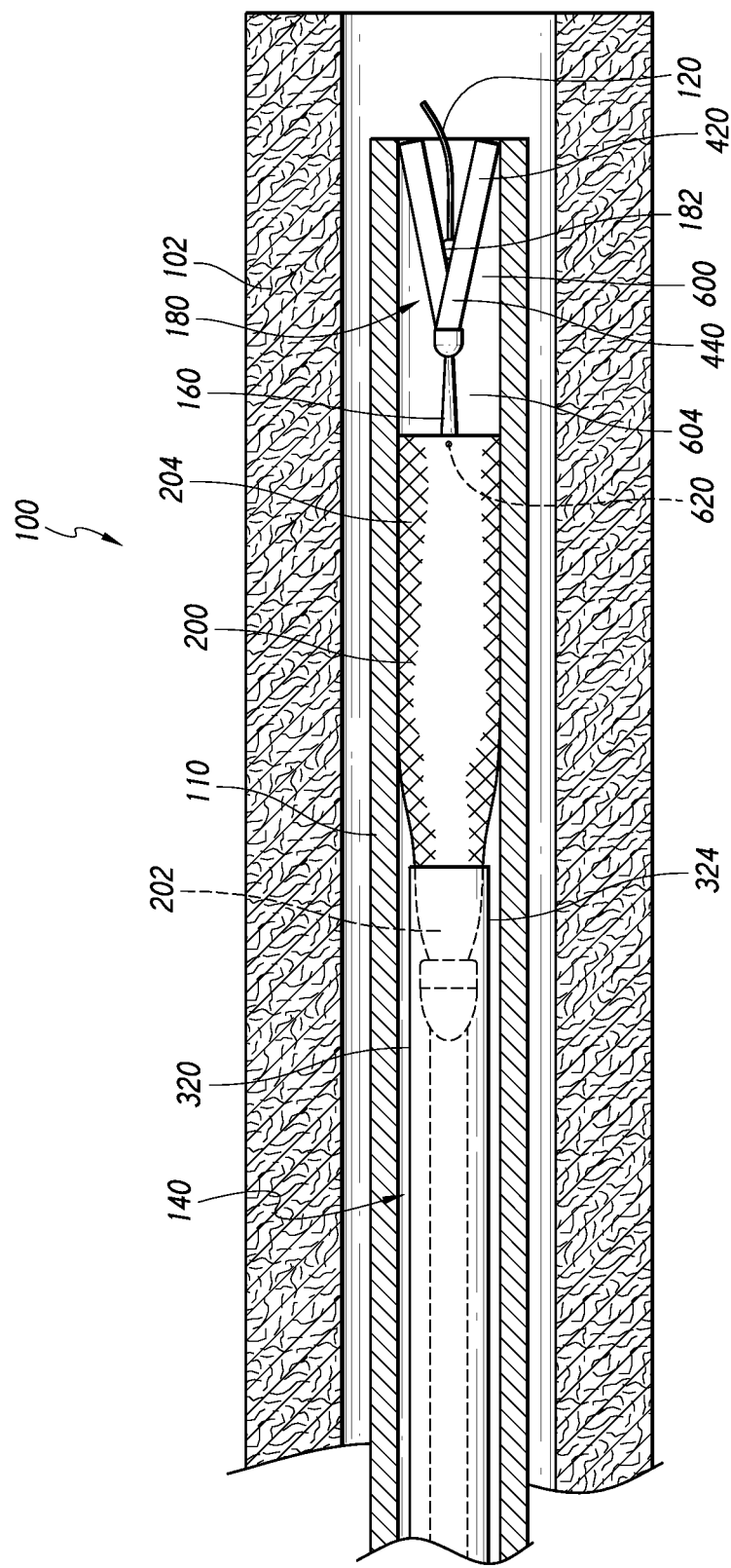
FIG. 15 is a schematic, partial cross-sectional view of the system of FIG. 1, in which the stent and a distal tip assembly of the core assembly have been retracted or resheathed into the catheter lumen after initial expansion of the stent, according to some embodiments.
Figure 17:
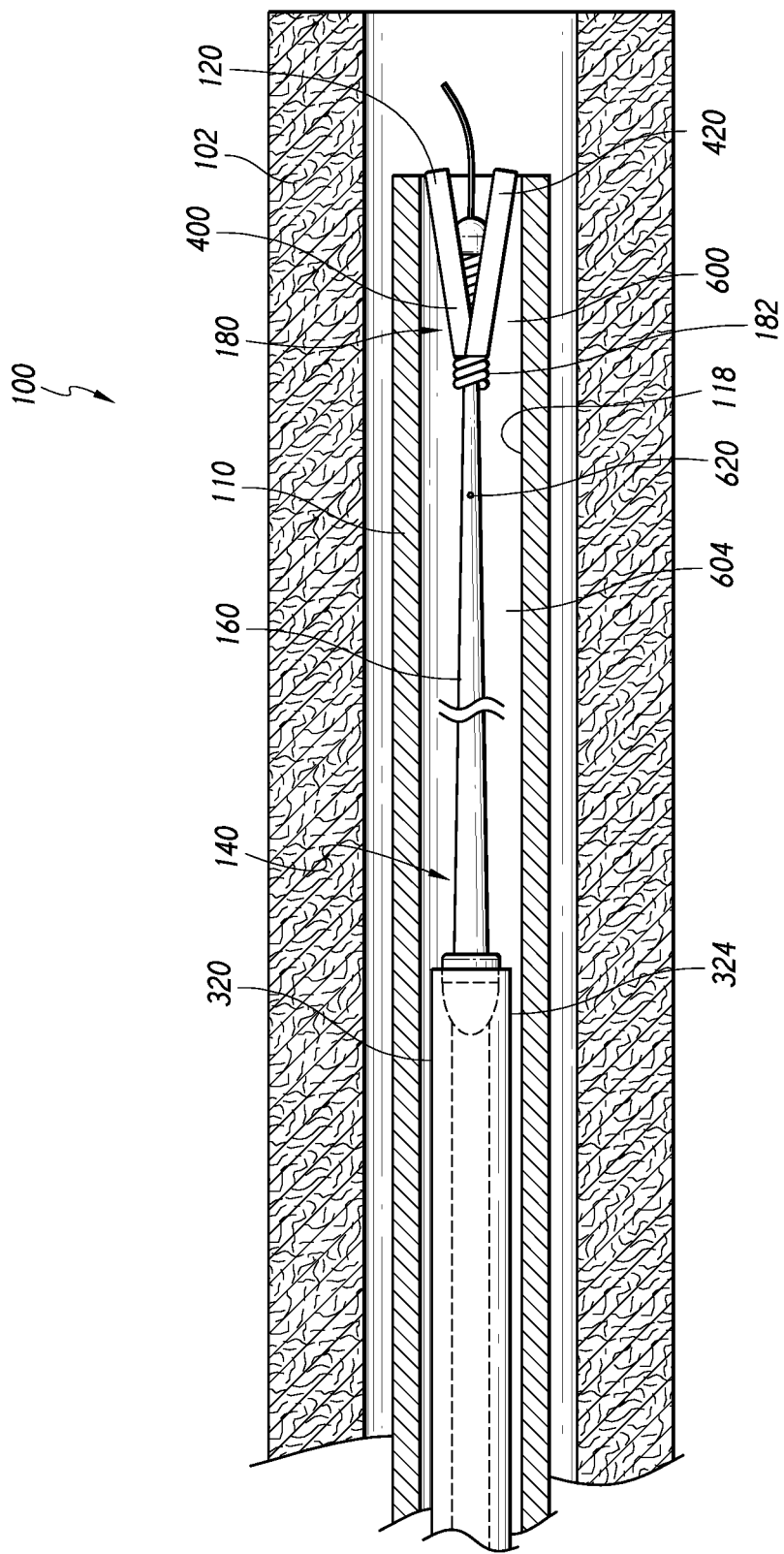
FIG. 17 is a schematic, partial cross-sectional view of the system of FIG. 1, in which the core assembly has been retracted or received into the catheter lumen after releasing the stent, according to some embodiments.

After the distal cover 400 has become disengaged from the stent 200 to reach the state shown in FIG. 12A, the cover can proceed to the second orientation as shown in FIG. 12B or 12C, as oncoming blood flow urges the first section 420 distally. Alternatively, the distal cover 400 can remain substantially in the disengaged, distally-extending configuration shown in FIG. 12A until the core assembly 140 is withdrawn proximally into the catheter 110, at which point the distal end of the catheter 110 can force the approaching first section 420 of the cover 400 to evert or otherwise take on the second configuration as shown in FIG. 15 or 17. In each case, the distal cover 400 can move toward an everted position or configuration in which the first section 420 of the distal cover 400 is flipped, everted or rotated to extend in a distal direction or in a "distally oriented" position or configuration. In some embodiments of a distally-oriented second configuration, all or at least a portion of the first section 420 is located distal of all or at least a portion of the second section 440.

Figure 13:
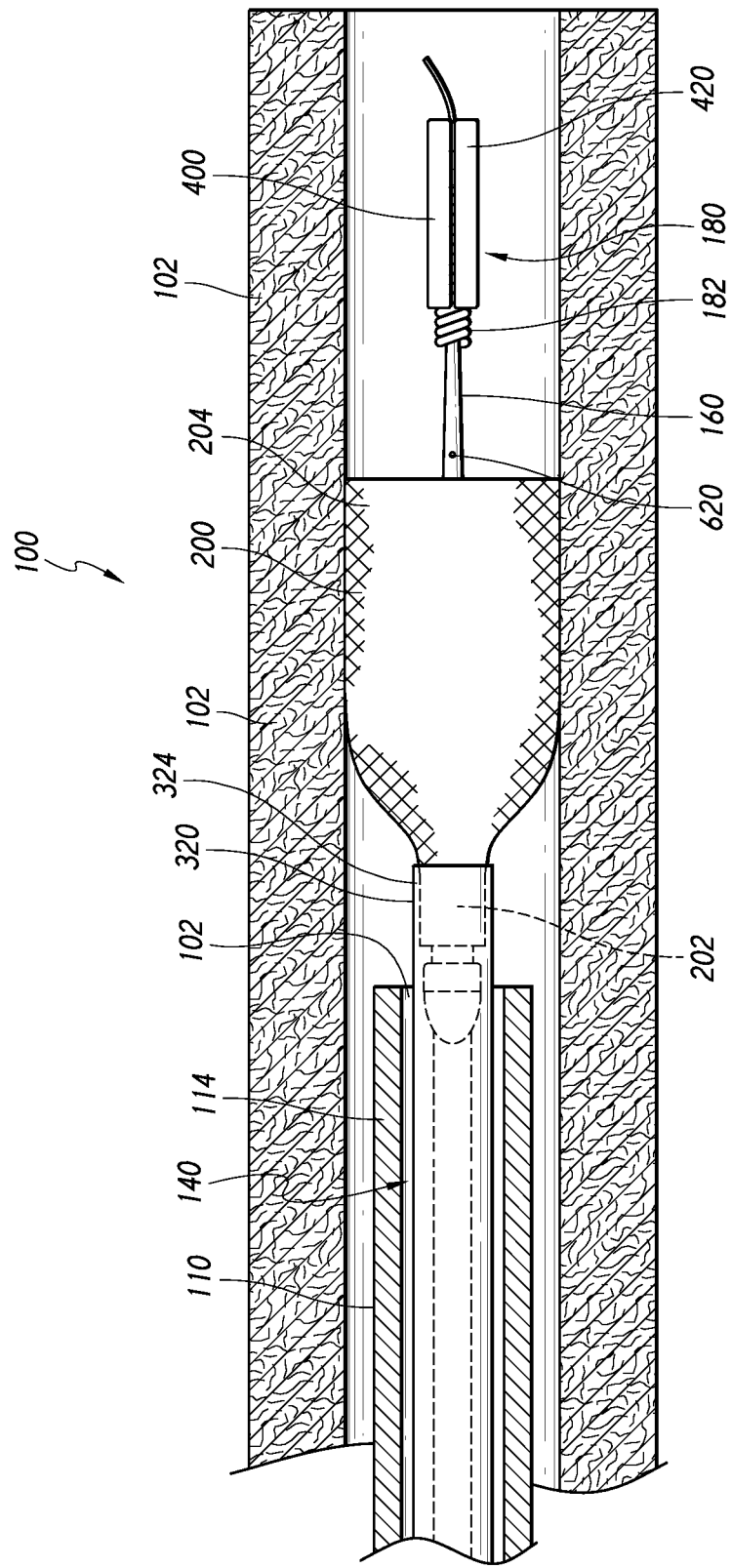
FIG. 13 is a schematic, partial cross-sectional view of the system of FIG. 1, in which the stent has been partially expanded against the vessel wall and moved outside of a catheter lumen, according to some embodiments.
Figure 14:
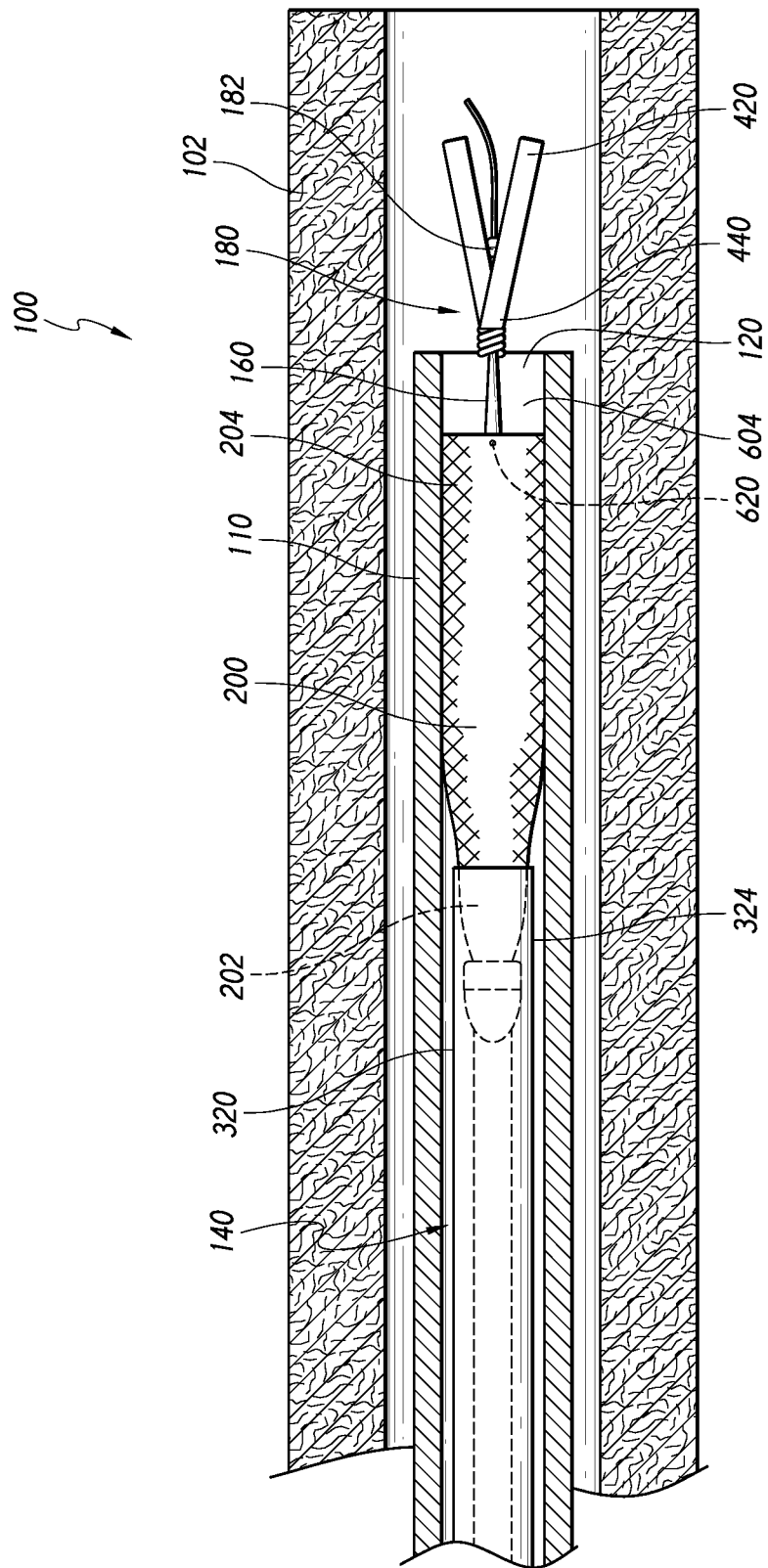
FIG. 14 is a schematic, partial cross-sectional view of the system of FIG. 1, in which the stent has been retracted or resheathed into the catheter lumen after initial expansion of the stent, according to some embodiments.
Figure 16:
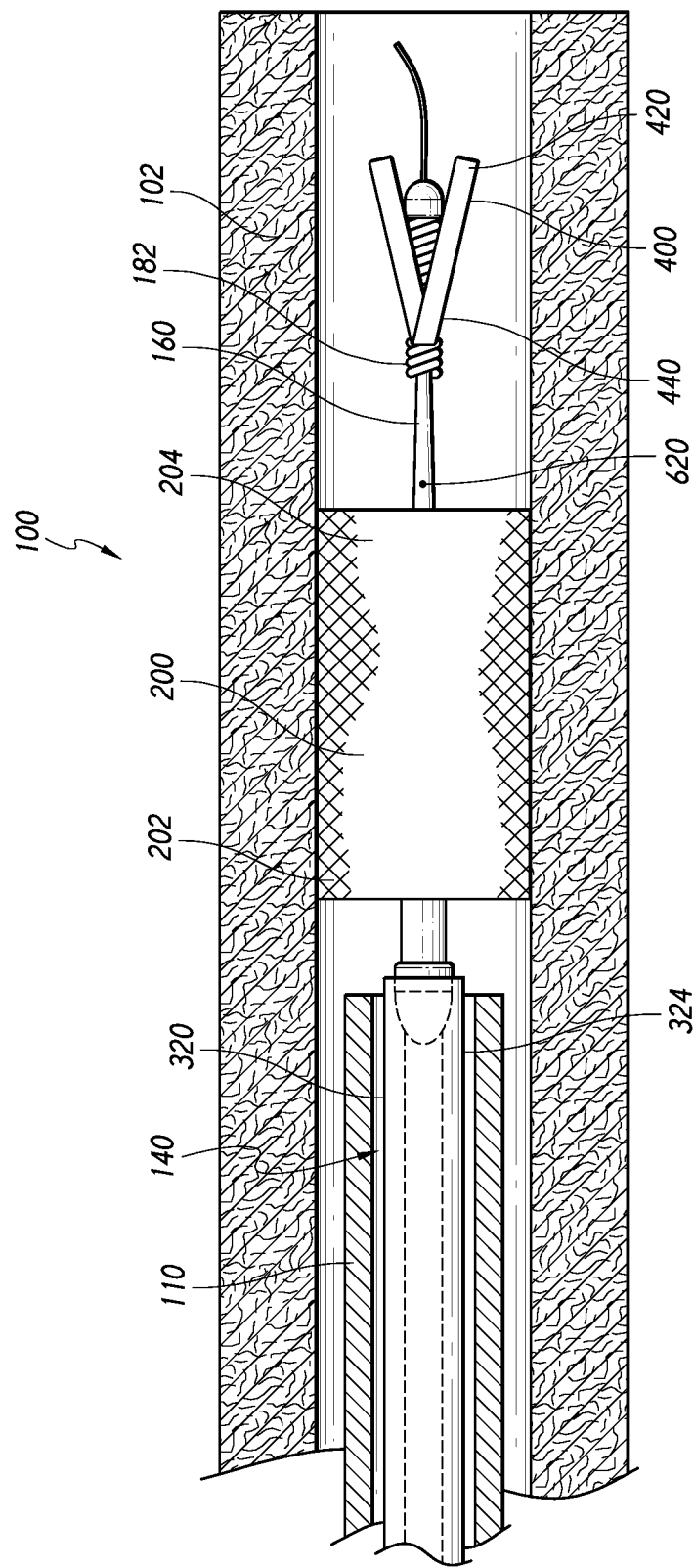
FIG. 16 is a schematic, partial cross-sectional view of the system of FIG. 1, in which the stent has been expanded and released from the core assembly into apposition with the vessel wall, according to some embodiments.

The stent 200 can be further unsheathed (as shown in FIG. 13) and subsequently released (as shown in FIG. 16), or the stent 200 can be retracted and withdrawn back into the catheter 110 (as shown in FIG. 14-15), if needed. In either situation, when the distal portion of the core assembly 140 is withdrawn into the lumen of the catheter 110, the distal cover 400 can be retracted into the catheter 110 in the second position, configuration, or orientation, in which the distal cover 400 can be at least partially everted, as shown in FIGS. 14-15 and 17. This can facilitate complete resheathing of the stent 200 and/or the core assembly 140 within the catheter 110.

In some embodiments, in the first orientation, the first section 420 of the distal cover 400 is positioned outside of a radial space 600 located between the tip assembly 180 and the catheter 110, as shown in FIG. 5. The distal cover 400 can extend proximally from the distal portion or the tip assembly 180 and from the radial space 600 between the distal portion or tip assembly 180 and the catheter 110. Additionally, in some such embodiments, in the second orientation, the first section 420 of the distal cover 400 extends distally through the radial space 600 upon retraction of the core assembly 140 into the catheter 110, as shown in FIGS. 15 and 17.

Further, in some embodiments, in the first orientation, at least a portion of the distal cover 400 can extend into a radial space 604 within the catheter lumen 116 located between a distal end 612 of the intermediate portion 614 of the core member 160 and the distal end 114 of the catheter 110. For example, referring to FIGS. 5A-B, the first section 420 of the distal cover 400 can extend or be interposed radially between the distal end 612 of the intermediate portion 614 and the inner surface 118 of the catheter 110. Additionally, in some embodiments, in the second orientation, the first section 420 of the distal cover 400 no longer extends or is no longer interposed radially between the distal end 612 of the intermediate portion 614 and the inner surface 118 of the catheter 110 (and the first section 420 can be located distally of such location), upon retraction of the core assembly 140 into the catheter 110, as shown in FIGS. 15 and 17.

Further, in some embodiments, the first section 420 of the distal cover 400 can radially overlap with the distal end 204 of the stent 200 at an overlap point 620 along the core member 160. As illustrated in FIGS. 5A-B and 12, the overlap point 620 can be located along the core member 160 proximal to the tip assembly 180. In some embodiments, the overlap point 620 can be spaced about 5 mm to about 12 mm from the proximal end of the distal tip structure 182. In some embodiments, the overlap point 620 can be spaced about 6 mm to about 10 mm from the proximal end of the distal tip structure 182. Further in some embodiments, the overlap point 620 can be spaced about 8 mm from the proximal end of the distal tip structure 182. The overlap point 620 can be located at or near the distal end 612 of the intermediate portion 614 of the core member 160, or at any location along the core member 160 that underlies an overlap of the (first section 420 of the) distal cover 400 over the stent 200 when the core assembly 140 is in its pre-deployment configuration shown in FIGS. 1-5B and 13A-13B. Additionally, in some such embodiments, in the second orientation, the first section 420 of the distal cover 400 no longer overlaps with the (distal end 204 of) the stent 200 at the overlap point 620 (and the first section 420 can be located distally of such location), upon retraction of the core assembly 140 into the catheter 110, as shown in FIGS. 15 and 17.

In the second orientation, as shown in FIGS. 12A-13, there is no longer radial overlap of the stent 200 and the cover 400 at the overlap point 620 or at the distal end 612 of the intermediate section 614. Thus, after disengagement of the distal cover 400 from the stent 200, the core assembly 140 can be proximally withdrawn into the catheter 110 and the distal cover 400 will generally extend in a distal direction away from the overlap point 620. As also shown in FIG. 14-15, at such time that the stent 200 is resheathed or withdrawn into the catheter 110 after partial expansion, the stent 200 and the distal cover 400 will not overlap at the overlap point 620. Thus, the distal cover 400 will not overlap the stent 200 or the overlap point 620 after at least partial expansion of the stent 200 when the core assembly 140 is withdrawn into the catheter 110. Further, once the distal cover 400 is disengaged, the intermediate portion 614 of the core member 160 can be positioned radially adjacent to the distal end 114 of the catheter 110 with the distal cover 400 being positioned outside of the radial space 604 between the intermediate portion 614 and the catheter 110. Accordingly, the movement and configuration of the distal cover 400 can enable the core assembly 140 to provide radial clearance between the core member 160 or the intermediate portion 614 and the catheter 110 for facilitating resheathing of the core member 160, as shown in FIGS. 14-15 and 17.

The distal cover can be coupled relative to the core member. The distal cover can be bonded to the core member and/or the tip assembly 180 of the core assembly. In some embodiments, the distal cover can be threaded into a coil of the tip assembly 180. In the embodiment shown in FIG. 5A, the distal cover 400 can be coupled directly to the distal tip structure 182 and indirectly coupled to the core member 160. In the embodiment of FIG. 5A, the distal tip structure 182 is rigidly coupled to the core member 160. However, the distal tip structure 182 can also be movable relative to the core member 160, to provide relative rotation or sliding along the core member 160, as discussed below with regard to FIG. 5C.

For example, the distal cover 400 and/or the distal tip structure 182 can be configured to rotate about the core member 160. For example, an end of the distal cover 400 can be rotatably coupled with respect to the core member 160. Thus, the stent 200 can be configured to rotate about the core member 160 at least in part by virtue of the rotatable coupling of the distal cover 400. Accordingly, in some embodiments, the stent can rotate with respect to the core member 160 while minimizing any torsional stresses on the stent.

In the embodiment of FIG. 5A, the distal cover 400 comprises a shrink tube 460 configured to shrink and adhere the second section 440 to the distal tip structure 182. Alternatively, the second section 440 of the distal cover 400 can be coupled to the distal tip structure 182 via other devices or attachment means, including, but not limited to mechanical fasteners, welding techniques, adhesives, heat bonding, combinations thereof, or the like. In yet another alternative, the second section 440 can be coupled directly to a distal portion or the distal end 164 of the core member 160 itself using any suitable attachment.

In some embodiments, the distal tip structure 182 can comprise at least one member that can be oriented generally transverse or parallel to the core member. For example, the tip structure 182 can comprise a coil(s), a circumferentially-extending band(s) of material, a clamp(s), and/or other structures that can pass smoothly within a vessel at the distal portion of the core member. Further, the at least one member can comprise at least one segment of the coil or other structure. According to some embodiments, the distal cover 400 can be coupled to the distal tip structure 182 by virtue of forming an enclosure that encloses the at least one member. For example, the distal cover 400 can form an enclosure that encloses at least one coil segment of the distal tip structure 182 by virtue of at least partially wrapping around the segment.

FIG. 5B illustrates another embodiment of a core assembly 140'. The core assembly 140' comprises a core member 160', a distal tip assembly 180' (having a distal tip structure 182' in the form of a coil), and a distal cover 400'. The distal cover 400' comprises a free first section 420' and a fixed second section 440'. The second section 440' is attached to the coil of the distal tip structure 182' by passing or being looped between adjacent windings of the coil (or otherwise through a side of the coil or around one or more windings of the coil), as illustrated. The second section 440' can comprise a looped portion 442' that extends between the adjacent coil windings and proximally back into contact with another portion of the second section 440'. The overlapping aspects of the looped portion 442' and the second section 440' can be fused or otherwise joined or adhered to each other to securely attach the distal cover 400' to the distal tip structure 182'. Other components of the core assembly 140' and catheter 110' are labeled similarly to FIG. 5A, as illustrated.

FIG. 5C is a rear perspective view of a distal cover 400". The distal cover 400" can be similar in structure, function and method of use to the distal cover 400 (e.g., as shown in FIG. 5A) and/or the distal cover 400' (e.g., as shown in FIG. 5B), but with additional or substituted structures, functions and uses as described herein. The distal cover 400" can be used in place of the distal covers 400/400' in constructing any embodiment of the core assembly 140. The distal cover 400" can be coupled to a distal tip assembly 180" in a manner similar to that illustrated in FIG. 5B. However, in this embodiment, the distal tip assembly 180" comprises a distal tip structure 182" that is longitudinally and/or rotatably movable relative to the core member 160".

In some embodiments, the core member 160" can comprise an proximal stop member or restraint 430" and a distal stop member or restraint 432". The proximal restraint 430" and the distal restraint 432" can be configured to limit the range of sliding movement of the distal tip structure 182". The proximal restraint 430" and the distal restraint 432" can be spaced apart from each other along the core member 160" by a distance that permits longitudinal movement of the tip structure 182" relative to the core member 160". In some embodiments, the restraints 430, 432 permit substantially zero longitudinal movement of the tip structure 182" and cover 400" but do allow these components to rotate about the core member 160".

The distal tip structure 182" can comprise an inner lumen that receives the core member 160" therein such that the distal tip structure 182" can slide and/or rotate relative to the core member 160". For example, some embodiments of the distal tip structure 182" can comprise a coil. Thus, the distal cover 400" can rotate and/or slide relative to the core member 160". Such movement can allow the distal cover 400" to move or rotate with the stent during delivery to reduce stresses and pushing force as the core assembly 140" traverses the vasculature of the patient.

The distal cover can be one or more strips, wings, or elongate portions that are coupled to the tip assembly and/or core member of the core assembly. In some embodiments, the distal cover comprises no more than two elongate strips, wings, or elongate portions. The strips, wings, or elongate portions can be formed as separate components that are coupled to the core assembly. Further, the strips, wings, or elongate portions can also be formed from a single, continuous piece of material that is coupled to the core assembly. The strips, wings, or elongate portions can have free first ends, as well as second ends that are coupled to the core assembly. The free first ends can cover at least a portion of the stent distal portion during delivery of the stent. Further, when the core assembly is proximally withdrawn into the catheter, the strips, wings, or elongate portions can be everted, such that free first ends of the strips, wings, or elongate portions are drawn together distal to the second ends.

For example, the distal cover can be manufactured or otherwise cut from a tube of the material selected for the distal cover. As illustrated in FIGS. 5-6, in some embodiments, the first section 420 may be formed as multiple longitudinal strips cut from the tube, and the second section 440 may be an uncut length of the tube. Accordingly, the tubular second section 440 and the proximally extending strips of the first section 420 may form a single, integral device or structure.

In some embodiments, the distal cover 400 may comprise a tube and the first section 420 can include two or more semi-cylindrical or partially cylindrical strips or tube portions separated by a corresponding number of generally parallel, longitudinally oriented cuts or separations formed or otherwise positioned in the sidewall of the tube. Therefore, when in the pre-expansion state, as shown in FIGS. 1, 2, 4, 5 and 6, the first section 420 may generally have the shape of a longitudinally split or longitudinally slotted tube extending or interposed radially between the outer surface 208 of the stent 200 and the inner surface 118 of the catheter 110.

In various embodiments, the strips, wings, or elongate portions of the first section 420 may collectively span substantially the entire circumference of the outer surface 208 of the stent 200 (e.g., where the cuts between the strips are splits of substantially zero width), or be sized somewhat less than the entire circumference (e.g., where the cuts between the strips are slots having a nonzero width). In accordance with some embodiments, the width of the strips, wings, or elongate portions of the first section 420 can be between about 0.5 mm and about 4 mm. The width can be about 0.5 mm to about 1.5 mm. In accordance with some embodiments, the width can be about 1 mm.

The strips, wings, or elongate portions of the first section 420 can also extend longitudinally over at least a portion of the distal portion of the stent. In some embodiments, the first section 420 can extend between about 1 mm and about 3 mm over the distal portion of the stent. Further, the first section 420 can also extend between about 1.5 mm and about 2.5 mm over the distal portion of the stent. In accordance with some embodiments, the first section 420 can extend about 2 mm over the distal portion of the stent.

The first section 420 and the second section 440 can define a total length of the distal cover 400. In some embodiments, the total length can be between about 4 mm and about 10 mm. The total length can also be between about 5.5 mm and about 8.5 mm. In some embodiments, the total length can be about 7 mm.

The strips of the first section 420 may be of substantially uniform size. For example, the first section 420 can comprise two strips spanning approximately 180 degrees each, three strips spanning approximately 120 degrees each, four strips spanning approximately 90 degrees each, or otherwise be divided to collectively cover all or part of the circumference of the stent, etc. Alternatively, the strips may differ in angular sizing and coverage area without departing from the scope of the disclosure. In one embodiment, only two strips or tube portions are employed in the first section 420. The use of only two strips can facilitate radial expansion, distal movement and/or fold-over or everting of the first section 420, as discussed herein, while minimizing the number of free or uncontained strips in the blood vessel lumen and any potential for injuring the vessel by virtue of contact between a strip and the vessel wall.

In accordance with some embodiments, at or near the distal end 204 of the stent 200, the first section 420 of the distal cover 400 may be configured to evert or otherwise fold over and/or within itself, thereby creating a folded portion 480 extending or interposed radially between the outer surface 208 of the stent 200 and the inner surface 118 of the catheter 110, as shown in FIGS. 5A-B. As illustrated, the folded portion 480 can have an outer layer 482 and an inner layer 484, where the outer layer 482 is radially adjacent the inner surface 118 of the catheter 110 and the inner layer 484 is radially adjacent the outer surface 208 of the stent 200. In such embodiments, the configuration of the inner layer 484, which is radially adjacent to the outer surface 208 of the stent 200, can advantageously facilitate expansion of the stent 200 because the stent 200 would not need to slide along the inner layer 484. Instead, the inner layer 484 can be everted as the stent expands, thereby reducing any friction between the stent 200 and the distal cover 400.

Further, in some embodiments, the distal cover 400 can be configured to fold over itself, in a manner opposite to that shown in FIGS. 5A-B, such that layer 482 is the inner layer and layer 484 is the outer layer. In other embodiments, the first section 420 is not folded, everted, or everted at all, when in the first or pre-expansion configuration.

The distal cover can be manufactured using a lubricious and/or hydrophilic material such as PTFE or Teflon®, but may be made from other suitable lubricious materials or lubricious polymers. The distal cover can also comprise a radiopaque material. For example, one or more strips of Teflon® can be coupled to the core member or distal tip structure in order to form the distal cover. The distal cover can define a thickness of between about 0.0005" and about 0.003". In some embodiments, the distal cover can be one or more strips of PTFE having a thickness of about 0.001". The material of the distal cover can also be attached by means of another material, such as the shrink tube 460, fitted around the perimeter of the distal cover. The shrink tube 460 can define a radial thickness of between about 0.001" and about 0.002". Some embodiments, the radial thickness of the shrink tube is about 0.0015" (based on a tubular shape having an inner diameter of about 0.016" had an outer diameter of about 0.019"). Thus, the radial clearance between the distal cover (when everted) and the inner surface of the catheter can be about 0.002" and about 0.004".

When the core assembly 140 is being withdrawn, as shown in FIG. 15 or 17, the distal cover 400 can extend distally through the annular space between the distal tip of the core member 160 and the inner surface 118 of the catheter 110 and provide a clearance therebetween. The clearance between the inner surface 118 and the distal cover 400 (when urged against the distal tip of the core member 160) can be equal to or greater than the radial clearance between the outer surface of the constraining member 320 and the inner surface 118 of the catheter 110. Thus, as noted above, if the inner diameter of the catheter 110 is about 0.030" and the outer diameter of the constraining member 320 is about 0.025", the radial clearance between the inner surface 118 and the distal cover 400 would at least about 0.0025". Further, as also noted herein, the outer diameter of the distal tip structure 182 can be about 0.015".

In operation, the distal cover 400, and in particular the first section 420 or the folded portion 480, can generally cover and protect the distal end 204 of the stent 200 as the stent 200 is moved distally within the catheter 110. The distal cover 400 may serve as a bearing or buffer layer that, for example, inhibits filament ends 212 of the distal end 204 of the stent 200 (shown schematically in FIGS. 5A-B) from contacting the inner surface 118 of the catheter 110, which could damage the stent 200 and/or catheter 110, or otherwise compromise the structural integrity of the stent 200. Since the distal cover 400 may be made of a lubricious material, the distal cover 400 may exhibit a low coefficient of friction that allows the distal end 204 of the stent 200 to slide axially within the catheter 110 with relative ease. The coefficient of friction between the distal cover and the inner surface of the catheter can be between about 0.02 and about 0.4. For example, in embodiments in which the distal cover and the catheter are formed from Teflon®, the coefficient of friction can be about 0.04. Such embodiments can advantageously improve the ability of the core assembly to pass through the catheter, especially in tortuous vasculature.

Structures other than the herein-described embodiments of the distal cover 400 may be used in the core assembly 140 to cover the distal end of the stent 200. For example, a protective coil or other sleeve having a longitudinally oriented, proximally open lumen may be employed. Suitable such protective coils include those disclosed in the incorporated U.S. Patent Application Publication No. 2009/0318947 A1.

Further, as also noted herein, some embodiments can be configured such that the distal tip assembly (e.g., the distal tip structure 182) is rotatable and/or axially movable relative to the core member 160. Similarly, in embodiments wherein the distal tip assembly comprises only the distal cover 400, although the distal cover 400 can be fixedly coupled relative to the core member 160, the distal cover 400 can also be rotatably and/or axially movably coupled relative to the core member 160. Further, when the distal tip assembly comprises both the distal tip structure and the distal cover, the distal tip assembly can be rotatably and/or axially movably coupled relative to the core member; however, the distal tip assembly can also be fixedly coupled to the core member. Thus, as similarly noted above, some embodiments of the distal cover can allow the core member to rotate freely relative to the distal cover and the stent, thereby avoiding exertion of torsional forces on the stent and/or distal cover as the core assembly is moved through the catheter to the treatment site.

As noted, embodiments of the distal cover can provide various advantages. For example, the use of the distal cover can allow the stent holding assembly to be easily urged toward the treatment site within the catheter. This can advantageously reduce the delivery force required to move the core assembly through the catheter. In addition, the distal tip assembly can be compactly configured and therefore provide excellent maneuverability as the stent holding assembly moves through tortuous anatomy. Further, a flexible distal cover such as the depicted distal covers 400, 400', 400" can also allow the distal portion of the stent to open or expand radially immediately as the distal portion of the stent exits the catheter. The distal cover can be easily urged away from the first or encapsulating position or configuration such that the expansion of the stent is not hindered and expansion can be predictable to the clinician. Where employed, this can be a significant improvement over prior art devices that used a relatively rigid tube, such as a coil to distally restrain a distal end of the stent, which could impede or make unpredictable the proper expansion or deployment of an occluding device, especially large diameter occluding devices.

Further, where the first portion 420 is flexible, evertible, and/or provides a minimal cross-section, the distal tip assembly can be easily recaptured within the catheter to facilitate resheathing for retraction of the core assembly into the catheter. Thus, the catheter can remain in place and the entire core assembly can be withdrawn therefrom. This can enable the clinician to "telescope" one or more other occluding devices (e.g., delivering more than one occluding device such that it overlaps with another occluding device) without having to remove the catheter, saving time and reducing trauma to the patient.

Referring now to FIGS. 7-11, some embodiments of the stent delivery system can also be configured to include multiple stop members or restraints and engagement components that collectively facilitate engagement between the core assembly and the stent. Further, as discussed below, some embodiments can be provided which enable the delivery system to traverse the tortuous paths while minimizing the likelihood of damage to the stent.

Figure 7:
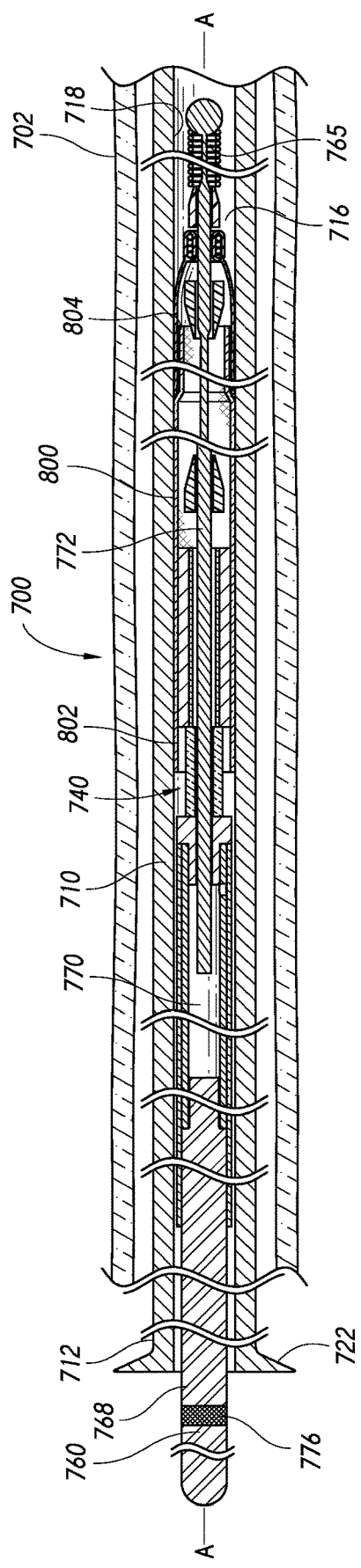
FIG. 7 is a side, cross-sectional view of a medical device delivery system disposed within a body lumen, according to some embodiments.

As shown in FIG. 7, the depicted medical device delivery system 700 can comprise an elongate tube or catheter 710 which slidably receives a core assembly 740 configured to carry the stent 800 through the catheter 710. The depicted catheter 710 (see FIGS. 7-9) has a proximal end 712 and an opposing distal end 714 which can be positioned at a treatment site within a patient, an internal lumen 716 extending from the proximal end 712 to the distal end 714, and an inner surface 718 facing the lumen 716. At the distal end 714, the catheter 710 has a distal opening 720 through which the core assembly 740 may be advanced beyond the distal end 714 in order to expand or deploy the stent 800 within the blood vessel 702. The proximal end 712 may include a catheter hub 722. The catheter 710 can define a generally longitudinal axis A-A extending between the proximal end 712 and the distal end 714. When the delivery system 700 is in use, the longitudinal axis need not be straight along some or any of its length.

The catheter 710 can optionally comprise a microcatheter. For example, the catheter 710 can optionally comprise any of the various lengths of the MARKSMAN™ catheter available from Covidien of Mansfield, Mass. USA. The catheter 710 can optionally comprise a microcatheter having an inner diameter of about 0.030 inches or less, and/or an outer diameter of 3 French or less near the distal end 714. Instead of or in addition to these specifications, the catheter 710 can comprise a microcatheter which is configured to percutaneously access the internal carotid artery, or a location within the neurovasculature distal of the internal carotid artery, with its distal opening 720.

Information regarding additional embodiments of the catheter 710, and additional details and components that can optionally be used or implemented in the embodiments of the catheter described herein, can be found in U.S. Patent Application Publication No. US 2011/0238041 A1, published on Sep. 29, 2011, titled Variable Flexibility Catheter. The entirety of the aforementioned publication is hereby incorporated by reference herein and made a part of this specification.

The core assembly 740 can comprise a core member 760 configured to extend generally longitudinally through the lumen 716 of the catheter 710. The core member 760 can have a proximal end or section 762 and a terminal or distal end 764, which can include a tip coil 765. The core member 760 can also comprise an intermediate portion 766 located between the proximal end 762 and the distal end 764, which intermediate portion is the portion of the core member 760 onto or over which the stent 800 is positioned or fitted or extends when the core assembly 740 is in the pre-deployment configuration as shown in FIGS. 7-8.

The core member 760 can generally comprise any member(s) with sufficient flexibility, column strength and thinness to move the stent 800 or other medical device through the catheter 710. The core member 760 can therefore comprise a wire, or a tube such as a hypotube, or a braid, coil, or other suitable member(s), or a combination of wire(s), tube(s), braid(s), coil(s), etc. The embodiment of the core member 760 depicted in FIGS. 7-8 is of multi-member construction, comprising a proximal wire 768, a tube 770 (e.g., a hypotube) connected at its proximal end to a distal end of the proximal wire 768, and a distal wire 772 connected at its proximal end to a distal end of the tube 770. An outer layer 774, which can comprise a layer of lubricious material such as PTFE (polytetrafluoroethylene or TEFLON™) or other lubricious polymers, can cover some or all of the tube 770 and/or proximal wire 768. The proximal and/or distal wires 768, 772 may taper or vary in diameter along some or all of their lengths. The proximal wire 768 may include one or more fluorosafe markers 776, and such marker(s) can be located on a portion of the wire 768 that is not covered by the outer layer 774, e.g., proximal of the outer layer 774. This portion of the wire 768 marked by the marker(s) 776, and/or proximal of any outer layer 774, can comprise a bare metal outer surface.

The core assembly 740 can further comprise a proximal device interface 780 and/or a distal device interface 790 that can interconnect the medical device or stent 800 with the core member 760. The proximal device interface 780 can comprise a proximal engagement member 782 that is configured to underlie the stent 800 and engage an inner wall of the stent. In this manner, the proximal engagement member 782 cooperates with the overlying inner wall 718 of the catheter 710 to grip the stent 800 such that the proximal engagement member 782 can move the stent 800 along and within the catheter 710, e.g., as the user pushes the core member 760 distally and/or pulls the core member proximally relative to the catheter 710, resulting in a corresponding distal and/or proximal movement of the stent 800 within the catheter lumen 716.

The proximal engagement member 782 can be fixed to the core member 760 (e.g., to the distal wire 772 thereof in the depicted embodiment) so as to be immovable relative to the core member 760, either in a longitudinal/sliding manner or a radial/rotational manner. Alternatively, as depicted in FIGS. 7-8, the proximal engagement member 782 can be coupled to (e.g., mounted on) the core member 760 so that the proximal engagement member 782 can rotate about the longitudinal axis A-A of the core member 760 (e.g., of the distal wire 772), and/or move or slide longitudinally along the core member. In such embodiments, the proximal engagement member 782 can have an inner lumen that receives the core member 760 therein such that the proximal engagement member 782 can slide and/or rotate relative to the core member 760. Additionally in such embodiments, the proximal device interface 780 can further comprise a proximal restraint 784 that is fixed to the core member 760 and located proximal of the proximal engagement member 782, and/or a distal restraint 786 that is fixed to the core member 760 and located distal of the proximal engagement member 782. The proximal and distal restraints 784, 786 can be spaced apart along the core member 760 by a longitudinal distance that is greater than the length of the proximal engagement member, so as to leave one or more longitudinal gaps 787 between the proximal engagement member 782 and one or both of the proximal and distal restraints 784, 786, depending on the position of the proximal engagement member between the restraints. When present, the longitudinal gap(s) 787 allow the proximal engagement member 782 to slide longitudinally along the core member 760 between the restraints 784, 786. The longitudinal range of motion of the proximal engagement member 782 between the restraints 784, 786 is approximately equal to the total length of the longitudinal gap(s) 787.

Instead of or in addition to the longitudinal gap(s) 787, the proximal device interface 780 can comprise a radial gap 788 (see FIG. 8) between the outer surface of the core member 760 and the inner surface of the proximal engagement member 782. Such a radial gap 788 can be formed when the proximal engagement member 782 is constructed with an inner luminal diameter that is somewhat larger than the outer diameter of the corresponding portion of the core member 760. When present, the radial gap 788 allows the proximal engagement member 782 to rotate about the longitudinal axis A-A of the core member 760 between the restraints 784, 786. The presence of longitudinal gaps 787 of at least a minimal size on either side of the proximal engagement member 782 can also facilitate the rotatability of the proximal engagement member.

One or both of the proximal and distal restraints 784, 786 can have an outside diameter or other radially outermost dimension that is smaller than the outside diameter or other radially outermost dimension of the proximal engagement member 782, so that one or both of the restraints 784, 786 will tend not to contact the inner surface of the stent 800 during operation of the core assembly 740.

In the proximal device interface 780 shown in FIGS. 7-8, the stent 800 can be moved distally or proximally within the catheter 700 via the proximal engagement member 782. During distal movement, the distal end of the proximal restraint 784 bears on the proximal end of the engagement member 782, and the engagement member urges the stent 800 distally via frictional engagement with the inner surface of the stent 800 (assisted by the overlying catheter 710). During proximal movement, the proximal end of the distal restraint 786 bears on the distal end of the engagement member 782, which in turn moves the stent 800 proximally via such frictional engagement. Proximal movement of the stent 800 relative to the catheter 710 can be employed when withdrawing or re-sheathing the stent 800 back into the distal end 714 of the catheter 710, as will be discussed in greater detail below. When the stent 800 has been partially deployed and a portion of the stent remains disposed between the proximal engagement member 782 and the inner wall of the catheter, the stent 800 can be withdrawn back into the distal opening 720 of the catheter by moving the core assembly 740 (including the engagement member 782) proximally relative to the catheter 710 (and/or moving the catheter 710 distally relative to the core assembly 740). Re-sheathing in this manner remains possible until the engagement member 782 and/or catheter 710 have been moved to a point where the engagement member 782 is beyond the distal opening 720 of the catheter 710 and the stent 800 is released from between the member 782 and the catheter 710.

Optionally, the proximal edge of the proximal engagement member 782 can be positioned just distal of the proximal edge of the stent 800 when in the delivery configuration shown in FIGS. 7-8. In some such embodiments, this enables the stent 800 to be re-sheathed when as little as about 3 mm of the stent remains in the catheter 710. Therefore, with stents 800 of typical length, resheathability of 75% or more can be provided (i.e. the stent 800 can be re-sheathed when 75% or more of it has been deployed).

The distal device interface 790 can comprise a distal engagement member 792 that can take the form of, for example, a distal device cover or distal stent cover (generically, a "distal cover"). The distal cover 792 can be configured to reduce friction between the medical device or stent 800 (e.g., the distal portion or distal end thereof) and the inner surface 718 of the catheter 710. For example, the distal cover 792 can be configured as a lubricious, flexible structure having a free first end or section 792*a* that can extend over at least a portion of the stent 800 and/or intermediate portion 766 of the core assembly 760, and a fixed second end or section 792*b* that can be coupled (directly or indirectly) to the core member 760.

The distal cover 792 (e.g., the second end 792*b* thereof) can be fixed to the core member 760 (e.g., to the distal wire 772 or distal tip 764 thereof) so as to be immovable relative to the core member 760, either in a longitudinal/sliding manner or a radial/rotational manner. Alternatively, as depicted in FIGS. 7-8, the distal cover 792 (e.g., the second end 792*b* thereof) can be coupled to (e.g., mounted on) the core member 760 so that the distal cover 792 can rotate about the longitudinal axis A-A of the core member 760 (e.g., of the distal wire 772), and/or move or slide longitudinally along the core member. In such embodiments, the second end 792*b* can have an inner lumen that receives the core member 760 therein such that the distal cover 792 can slide and/or rotate relative to the core member 760. Additionally in such embodiments, the distal device interface 790 can further comprise a proximal restraint 794 that is fixed to the core member 760 and located proximal of the (second end 792*b* of the) distal cover 792, and/or a distal restraint 796 that is fixed to the core member 760 and located distal of the (second end 792*b* of the) distal cover 792. The proximal and distal restraints 794, 796 can be spaced apart along the core member 760 by a longitudinal distance that is greater than the length of the second end 792*b*, so as to leave one or more longitudinal gaps 797 between the second end 792*b* and one or both of the proximal and distal restraints 794, 796, depending on the position of the second end 792*b* between the restraints. When present, the longitudinal gap(s) 797 allow the second end 792*b* and/or distal cover 792 to slide longitudinally along the core member 760 between the restraints 794, 796. The longitudinal range of motion of the second end 792*b* and/or distal cover 792 between the restraints 794, 796 is approximately equal to the total length of the longitudinal gap(s) 797.

Instead of or in addition to the longitudinal gap(s) 797, the distal device interface 790 can comprise a radial gap 798 between the outer surface of the core member 760 (e.g., of the distal wire 772) and the inner surface of the second end 792*b*. Such a radial gap 798 can be formed when the second end 792*b* is constructed with an inner luminal diameter that is somewhat larger than the outer diameter of the corresponding portion of the core member 760. When present, the radial gap 798 allows the distal cover 792 and/or second end 792*b* to rotate about the longitudinal axis A-A of the core member 760 between the restraints 794, 796. The presence of longitudinal gaps 797 of at least a minimal size on either side of the second end 792*b* can also facilitate the rotatability of the distal cover.

One or both of the proximal and distal restraints 794, 796 can have an outside diameter or other radially outermost dimension that is smaller than the (e.g., pre-deployment) outside diameter or other radially outermost dimension of the distal cover 792, so that one or both of the restraints 794, 796 will tend not to bear against or contact the inner surface 718 of the catheter 710 during operation of the core assembly 740.

With reference now to FIGS. 8-9, it may be observed that the distal restraint 786 of the proximal device interface 780, and/or the proximal and/or distal restraints 794, 796 of the distal device interface 790, can each optionally comprise a tapered portion 850 and a cylindrical or non-tapered portion 852. In the proximal device interface 780, the distal restraint 786 can form a tapered portion 850 that is located distal of its non-tapered portion 852, and tapers down in diameter or cross-sectional size as it extends distally, away from the proximal engagement member 782. In the distal device interface 790, the proximal restraint 794 can form a tapered portion 850 that is located proximal of its non-tapered portion 852, and tapers down in diameter or cross-sectional size as it extends proximally, away from the distal engagement member 792; the distal restraint 796 can form a tapered portion 850 that is located distal of its non-tapered portion 852, and tapers down in diameter or cross-sectional size as it extends distally, away from the distal engagement member 792. Accordingly, in the depicted embodiment each of the restraints 786, 794, 796 forms a tapered portion 850 that tapers radially inwardly as it extends away from its respective engagement member 782/792 and/or its respective longitudinal gap(s) 787/797.

By incorporating the tapered portion(s) 850, the restraint(s) 786, 794, 796 can provide the benefit of relatively large diameter or cross-sectional size in the non-tapered portion 852 (effective longitudinal restraint of the engagement member 782/792) and/or relatively long axial length (secure attachment to the core member 760) without suffering the drawback of increased stiffness or reduced bendability of the core assembly 740 and delivery system 700. This may be understood best with reference to FIG. 9, which shows the delivery system 700 including the core assembly 740 passing through a bend in the vessel 702. In this drawing it can be observed that the tapered portion 850 of the distal restraint 786 of the proximal device interface 780 provides ample clearance for the sharply bending adjacent portion of the catheter 710 and stent 800, as compared to a non-tapered restraint of similar length and cross-sectional size or diameter. Accordingly the tapered restraint 786 allows the core assembly 740 and core member 760 to bend more sharply (and/or to bend without the restraint contacting the inner surface of the stent 800) in the vessel 702 than would be possible with a non-tapered restraint of similar axial length and cross-sectional size or diameter. In this manner the risk of a distal corner of the restraint 786 impinging on the inner surface of the stent 800 and creating a pressure concentration that can require a higher push force from the user, is reduced.

With further reference to FIG. 7, in some embodiments the distal restraint 796 of the distal device interface 790 may have a smaller (maximum) outside diameter or cross-sectional size than the proximal restraint 794 of the distal interface 790. Such a smaller distal restraint can help provide radial clearance for the everted first end 792*a* of the distal cover 792 during retraction into the catheter 710.

FIG. 10 shows an additional embodiment of the core assembly 740 (with the stent 800) which can be identical in structure, function and method(s) of use to any of the other embodiments of the core assembly 740 described herein, except as further described as follows. In this embodiment, the proximal device interface 780 (including for example the proximal engagement member 782 and/or its restraints 784, 786) can be located in a distal portion of the stent 800, e.g., in the distal half of the stent 800, overlapping with or just proximal of the distal cover 792, or partially or wholly overlapping with the distal cover 792. Further, according to some embodiments, that the proximal device interface 780 be located only in the distal half of the stent 800 does not mean that the proximal device interface 780 extends along the entire distal half, but instead can refer to embodiments in which the proximal device interface extends along less than the distal half.

For example, the proximal engagement member 782 can be located so that its distal end is less than 1 mm proximal of the proximal end of the cover 792, or distal of such location. With the proximal device interface 780 and proximal engagement member 782 so located, the member 782 can urge the stent 800 distally primarily by "pulling" the stent from a distal portion thereof, applying force to a point or region in a distal portion, or near the distal end, of the stent. When moving or pulling the stent in this fashion, the amount of push force necessary to be exerted through the core member 760 is reduced because the tendency of the stent to expand radially (as can occur when it is pushed distally and longitudinally compressed by a force applied to a point or region near the proximal end of the stent) is reduced. Optionally, in the embodiment of FIG. 10 there may be no additional structures proximal of the engagement member 782 and/or interface 780 that transmit force from the core member 760 or wire 772 to the stent 800.

FIG. 11 depicts an additional embodiment of the core assembly 740 which can be identical to the embodiment of FIG. 10, with the addition of a second proximal device interface 780' in a proximal portion of the stent 800, in addition to the distally located interface 780 described with reference to FIG. 10. The second interface 780' and/or its engagement member 782' can be located in a proximal portion of the stent 800, e.g., near the proximal end or in the proximal half of the stent 800. In such an arrangement, both the interfaces 780, 780' and/or members 782, 782' can urge the stent 200 distally in response to a distal push force exerted on the core member 760, thereby both "pulling" the stent from the distal portion and "pushing" it from the proximal portion. This can also reduce the amount of push force necessary to be exerted through the core member 760 to advance the stent into or through the catheter 710. In addition, the interface 780' and member 782' when located near the proximal end of the stent 800 can facilitate re-sheathing the stent 800 even when most of the stent 800 (e.g., except for the proximal-most portion thereof) has been deployed.

In the embodiments of FIGS. 10 and 11, any of the embodiments of the proximal device interface 780 and proximal engagement member 782 described herein (rotating, non-rotating, sliding, non-sliding, and any other varieties) can be employed.

FIGS. 1, 7-9, and 12A-18B depict some embodiments and methods of use of the stent delivery system 100. First, the catheter 110 can be inserted into the patient's vasculature via a percutaneous access technique or other suitable method of access. The distal end 114 of the catheter 110 is then advanced to a treatment site or location in the blood vessel 102. The blood vessel 102 may comprise a vein or artery, such as an artery in a brain or within a cranium of the patient. As previously mentioned, the catheter 110 can comprise a microcatheter. A guide catheter can be used instead of or in addition to the catheter 110; for example, the guide catheter can first be placed in the vasculature so that it extends part or all of the way to the treatment site and a microcatheter or other catheter then inserted through the guide catheter to the treatment site.

The treatment location may be near an aneurysm (not shown) formed in a wall of the blood vessel 102, and advancing the catheter 110 to the treatment location may include advancing the distal end 114 and/or distal opening 120 to a location that is distal of the aneurysm. Such advancement of the catheter 110 may include advancing the distal end 114 and/or distal opening 120 distally across the ostium or neck of the aneurysm, to the location in the vessel 102 distal of the aneurysm.

Once the catheter 110 has been inserted, it may extend proximally from the distal end 114 and/or distal opening 120 at the treatment location, through the vascular access site, to the proximal end 112 and/or hub 122 which are preferably situated outside the patient's body.

After the catheter 110 has been placed, the core assembly 140 (with the stent 200 carried thereby) can be inserted, distal end first, into the lumen 116 of the catheter 110 via the hub 122 and/or proximal end 112. Where the distal portion of the core assembly 140 is initially contained within an introducer sheath (not shown), the introducer sheath can be inserted partway into the catheter lumen 116 and the core assembly 140 is advanced distally through the introducer sheath until the distal portion and stent 200 exit the distal end of the introducer sheath and pass into (direct contact with) the lumen 116 of the catheter 110. The core assembly 140 and stent 200 are at that point disposed in the catheter 110 generally as depicted in FIG. 1, but in a proximal portion of the catheter 110. In particular, the stent 200 and distal portion of the core assembly 140 can be positioned in the lumen 116 of the catheter 110, with the proximal end 202 of the stent 200 received in the constraining member 320 and the remaining portions of the stent 200 extending distally and generally in contact with the inner surface 118 of the catheter except where the first section 420 of the distal cover 400 is extending or interposed radially between the distal end 204 of the stent 200 and the inner surface 118 of the catheter 110. Further, the core member 160 and constraining member 320 can extend proximally of the proximal end 112 and/or hub 122 of the catheter 110 to a location outside of the patient's body, so that the coupling 360 and proximal ends 162, 322 of the core member 160 and constraining member 320 can be easily accessed.

Next, the core assembly 140 with the stent 200 can be axially advanced distally within the lumen 116 of the catheter 110, toward the distal end 114 of the catheter 110 and treatment location. Generally, during advancement of the core assembly 140 in the catheter 110, the constraining member 320 and the engagement component 340 can secure, grip, or engage the stent 200 to facilitate urging the stent distally through the catheter 110, substantially without transmitting any securement forces to the catheter 110 or otherwise independently of the catheter 110. The constraining member 320 and the engagement component 340 can secure, grip, or engage the stent 200 during distal advancement through the catheter 110 without relative axial motion between the constraining member 320 and the engagement component 340, while the constraining member 320, the engagement component 340, and the stent 200 move distally relative to the catheter 110 and the vasculature.

As the stent 200 and distal cover 400 are advanced toward the distal end 114 and treatment location, the first section 420 of the distal cover 400 remains extending or interposed radially between the outer surface 208 and/or distal end 204 of the stent 200 and the inner surface 118 of the catheter 110.

Thus, the distal cover 400 may inhibit the distal end 204 of the advancing stent 200 (e.g., the filament ends 212 thereof) from damaging, abrading, or gouging the catheter 110, and from thereby impeding progress of the stent 200 along the catheter 110. This may, in turn, avoid damage to the stent 200 such as by longitudinal compression resulting from high friction generated between the distal end 204 of the stent 200 and the catheter 110 while distally directed force is applied to the first portions of the stent 200.

Where the treatment location is near an aneurysm and the distal end 114 and/or distal opening 120 of the catheter 110 has been advanced to a location that is distal of the aneurysm, advancement of the core assembly 140 with the stent 200 toward the distal end 114 and treatment location can include advancing the distal portion of the core assembly 140 and the distal end 204 of the stent 200 distally through the catheter 110 across the ostium or neck of the aneurysm, to a location in the vessel 102 distal of the aneurysm.

To begin expansion of the stent 200 (see FIG. 12A-12C), the core assembly 140 may be held stationary and the catheter 110 may be withdrawn proximally over the stent 200 and distal portion of the core assembly 140, until the distal end 114 of the catheter 110 is even with or proximal of the distal end 324 of the constraining member 320 or even with or proximal of the proximal end 202 of the stent 200 or proximal retaining member 220, as shown in FIG. 13. (Optionally, the core assembly and stent can be advanced distally while performing this step, instead of or in addition to withdrawal of the catheter.) As a result, the stent 200 (except for the portion retained in the constraining member 320) can be released and permitted to expand into engagement with the inner wall of the blood vessel 102, as shown in FIG. 13. Some embodiments of the stent 200 (such as certain braided stents) can shorten axially while expanding radially. As a result of (i) any axial foreshortening of the stent 200, (ii) radial expansion of the stent 200, and/or (iii) radial expansion of the distal cover 400 in response to radial expansion of the stent 200, the strips or tube portions of the first section 420 of the distal cover 400 can disengage from contact with the distal end 204 of the stent 200, while in some embodiments separating and moving radially outward as well.

In some embodiments, as the distal cover 400 disengages from the stent, it unfurls or otherwise unravels from its folded configuration 480 (see FIGS. 12-13). Once the distal cover 400 disengages or unravels, it no longer covers the distal end 204 of the stent 200; instead, its first section 420 is now spaced distally from the stent distal end 204 as shown in FIGS. 12-13. In this state, the strips or tube portions forming the proximal end can be free or unconfined within the lumen of the blood vessel 102. As similarly noted above, the strips or tube portions can have free first ends, as well as second ends that are coupled to the core assembly 140. The free first ends can cover at least a portion of the stent distal portion during delivery of the stent. Further, when the stent is expanded and/or the core assembly 140 is proximally withdrawn into the catheter, the strips or tube portions can be everted, such that free first ends of the strips, wings, or elongate portions are drawn together distal to the second ends thereof.

The pullback of the catheter 110 (and/or distal movement of the core assembly 140) and expansion of the stent 200 may be done in multiple discrete steps. For example, the catheter 110 may initially be pulled back proximally only part of the way to the location depicted in FIGS. 12A-12C, and only the distal portion 204 of the stent 200 expanded into engagement with the vessel wall. Such initial partial expansion facilitates anchoring the distal portion of the stent in the vessel 102, which in turn facilitates longitudinal stretching or compression of the stent 200 as desired by the clinician during or prior to expansion of the remaining portions of the stent 200 into the vessel 102. Initial partial expansion can also facilitate confirmation by the clinician that the distal portion of the stent 200 has "landed" in the desired location in the vessel 102 (e.g., distal of the neck or ostium of any aneurysm formed in the vessel wall) prior to expansion of the remaining portions of the stent 200. Generally, where an aneurysm is present in the vessel 102, proper placement of the stent 200 can include positioning a distal portion of the stent 200 in the vessel lumen distal of the aneurysm neck and a first portion of the stent in the vessel lumen proximal of the aneurysm neck, such that the stent 200 extends across the neck. Where the expanded stent 200 is appropriately configured, it may then perform a therapeutic flow-diverting function with respect to the aneurysm.

While the stent delivery system 100 is in the configuration shown in FIG. 13, with the proximal end 202 of the stent 200 retained within the constraining member 320, the partially expanded stent 200 can be resheathed or retracted proximally into the catheter 110 as shown in FIG. 14-15. The engagement mechanism, e.g., the constraining member 320 and the engagement component 340, can secure, grip, or engage the stent 200 to a sufficient degree to permit the catheter 110 to be advanced distally over the partially expanded stent 200 (and/or the core member 160 withdrawn proximally relative to the catheter 110) until the stent 200 is again positioned in the lumen 116 of the catheter 110. Thus, the engagement mechanism of the core assembly 140 can exert a proximal force on the stent 200 as the stent 200 is withdrawn or retracted into the catheter 110.

FIG. 14 shows a first aspect of a process of resheathing the stent 200, in which the stent 200, including the distal end 204, has been drawn into the lumen 116 of the catheter 110. Because the previously stent-engaging portion (e.g., the first section 420) of the distal cover 400 has moved radially outward from the core member 160 and/or distally relative to the core member 160, it does not impede the entrance of the distal portion and distal end 204 of the stent 200 into the distal opening 120 of the catheter 110 during resheathing. Accordingly, the resheathing process of FIG. 14-15 can comprise moving the stent 200 (including the distal end 204) into the catheter 110 through the distal opening 120 while the previously stent-engaging portion (e.g., the first section 420) of the distal cover 400 is in a second, everted, or resheathing configuration in which the stent-engaging portion is disposed radially outward from the core member 160 and/or the first section 420 of the distal cover 400 is disposed distally relative to the core member 160, the second section 440, and/or the distal tip structure 182, in comparison to a first, encapsulating, or delivery configuration (e.g., FIG. 1) of the stent-engaging portion (e.g., the first section 420) of the distal cover 400.

While FIG. 14 illustrates an initial aspect of the resheathing process, FIG. 15 shows a second aspect of the resheathing process currently under discussion. In this aspect of the process, the core assembly 140 can be moved further proximally into the catheter 110 (and/or the catheter 110 is moved further distally over the core assembly 140) until the distal cover 400 enters the catheter 110 via the distal opening 120. As noted above, the first section 420 of the distal cover 400 is preferably sufficiently flexible to evert and thereby attain the second, everted, or resheathing configuration shown in FIG. 14-15. In the second, everted, or resheathing configuration, the first section 420 of the distal cover 400 can extend generally in a distal direction, away from the stent 200, and/or extend distally of the second section 440 of the distal cover 400. Further, in some embodiments, the first section 420 of the distal cover 400 can also radially overlap the distal tip structure 182. Instead of or in addition to these aspects of the second, everted, or resheathing configuration, the distal cover 400 can be radially small enough to extend into the lumen 116 of the catheter 110, either partially as depicted in FIG. 14, or wholly as depicted FIG. 15, and/or the entire distal cover 400 can be spaced distally from the distal end 204 of the stent 200 in the lumen 116 of the catheter 110.

Accordingly, in accordance with some embodiments of methods disclosed herein, when operating the stent delivery system, a clinician can check the initial partial expansion of the stent 200 (e.g., as shown in FIGS. 12A-13) and, if the initial placement is unsatisfactory or if the initial expansion of the stent 200 is unsatisfactory, the clinician can recapture, collapse, withdraw, or resheath the stent 200 into the catheter 110, as described above with respect to FIGS. 14 and/or 15. After resheathing, the clinician can attempt to land the stent again, as described herein, beginning for example, with the state depicted in FIG. 14 or 13, and resulting for example, in the state depicted in FIG. 12A. Resheathing can also be performed, and the stent delivery system 100 and stent 200 removed from the patient entirely, if for example, the delivery and/or expansion of the stent 200 damages or reveals a defect in, or improper sizing of, the stent 200 or delivery system 100. After an initial partial expansion of the stent 200, the depicted core assembly 140 can optionally be entirely removed with the stent 200 from the catheter 110 without need to remove the catheter 110 from the blood vessel 102. In this manner, access to the treatment site in the blood vessel 102 can be maintained via the catheter 110 and, if desired, additional attempts to deliver the stent 200 can be made through the catheter 110.

If the initial expansion of the stent 200 in the vessel 102 is satisfactory, full expansion can be completed to result in the state depicted in FIG. 16. The coupling 360 is removed, broken, or otherwise disengaged to permit the constraining member 320 to move relative to the core member 160. The proximal end 202 of the stent 200 may then be released from the constraining member 320 and the engagement component 340 by holding the core member 160 stationary and withdrawing the constraining member 320 proximally relative to the core member 160 and the stent 200 until the distal end 324 is approximately even with the proximal retaining member 220, or otherwise proximal of the proximal end 202 of the stent 200. (If the distal end 114 of the catheter 110 has not yet been withdrawn to a location proximal of the proximal end 202 of the stent 200, that can be done as well.) No longer constrained by the constraining member 320 and the engagement component 340, the proximal end 202 of the stent 200 can now expand into contact with the wall of the vessel 102, as shown FIG. 16. (Note that until this point, according to an aspect of some embodiments, the partially expanded stent 200 had been fully resheathable.) Where the vessel 102 includes an aneurysm, the proximal end 202 is preferably located in the vessel 102 proximal of the aneurysm neck following expansion.

Following full expansion of the stent 200, the core assembly 140 can be drawn back into the catheter 110, as shown in FIG. 17. Both the catheter 110 and core assembly 140 can be withdrawn from the patient, either simultaneously or sequentially. However, when the stent has been successfully released, the core assembly 140 can also be entirely removed from the catheter 110, with the catheter 110 remaining in place, and a second core assembly can be inserted into the lumen. The second core assembly can be configured to deliver a second stent to the treatment site in order to perform, e.g., a telescoping procedure.

In another embodiment of a method, the stent 200 can be initially partially expanded (e.g., as shown in FIG. 13) in a blood vessel 102 wherein a branch vessel (not shown) joins the blood vessel at a junction located along the portion of the vessel 102 in which the stent 200 has been partially expanded. Patency of the branch vessel can then be checked by, for example, injecting a contrast agent near the junction and observing via, for example, fluoroscopy whether the agent can flow from the vessel 102 into the branch vessel. Thus it can be determined whether a portion of the stent 102 has occluded the branch vessel. If it appears that the branch vessel has been occluded, the stent 200 can be repositioned within the vessel 102 without resheathing, or the stent 200 can be resheathed using any of the techniques discussed herein. After resheathing, the stent 200 can be partially expanded again, and branch vessel patency checked again.

In the present disclosure, numerous references are made to moving the catheter 110 axially over the core assembly 140, and moving the core assembly 140 axially within the catheter 110. Except where specifically noted to the contrary, all such references to one form of this relative movement should be understood to include the other as an alternative.

As discussed above, the stent delivery system 100 can also be configured to allow the clinician to control the articulation and delivery of the system by steering a portion of the system. For example, referring to FIGS. 18A-18B, the stent delivery system 100 can optionally include a steerable tip assembly 900. The steerable tip assembly 900 can allow a clinician to avoid perforating or abrading the vessel wall of a vessel bifurcation or a sharp turn in the vessel while performing the procedure. As noted above, in some embodiments, the steerable tip assembly 900 can include the core member 160, which can have a curvilinear distal end 164. Optionally, in some embodiments, the steerable tip assembly 900 can be employed with one or more engagement components 340 that are rotatably mounted on the core member 160. Accordingly, the core member 160 can be configured to be steerable during stent expansion, or when the stent is in the catheter or partially expanded within the vessel by being rotatable relative to the stent 200, the catheter 110, and/or other components of the stent delivery system 100.

In use, the clinician can advance the stent delivery system 100 to the treatment location axially within the vessel 102. In preparation for deployment and expansion of the stent 200, the clinician can survey the surrounding vasculature of the treatment site and determine whether there is a risk of having the distal end of the core member abrade or perforate a vessel wall as the core member is advanced distally as anticipated during stent expansion or during advancement of the system 100 to the treatment location. Generally, the core member 160 and the distal tip assembly 180 are often advanced distally in the course of expanding a stent, so the anticipated distal movement can be that resulting from stent deployment near a bifurcation or sharp turn in the vessel. If there is a risk that abrasion or perforation of a vessel may take place, the clinician can carefully land the stent and thereafter (or beforehand) rotate the core member to reorient or redirect the distal end or point of the core member towards the pathway of the vessel and away from the vessel wall.

Figure 18A:
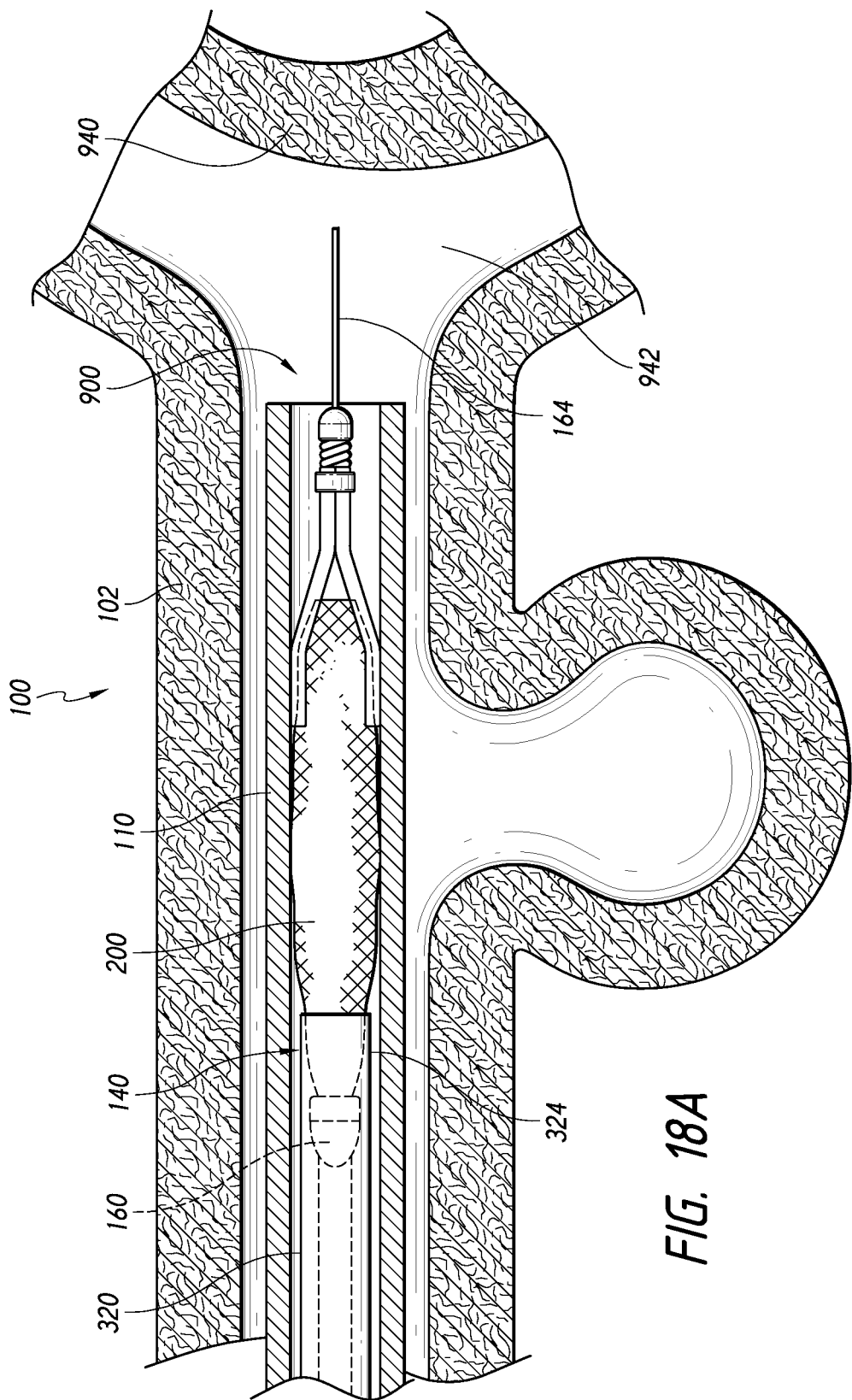
FIG. 18A is a schematic, partial cross-sectional view of a stent delivery system positioned at a treatment site adjacent to a vessel bifurcation.
Figure 18B:
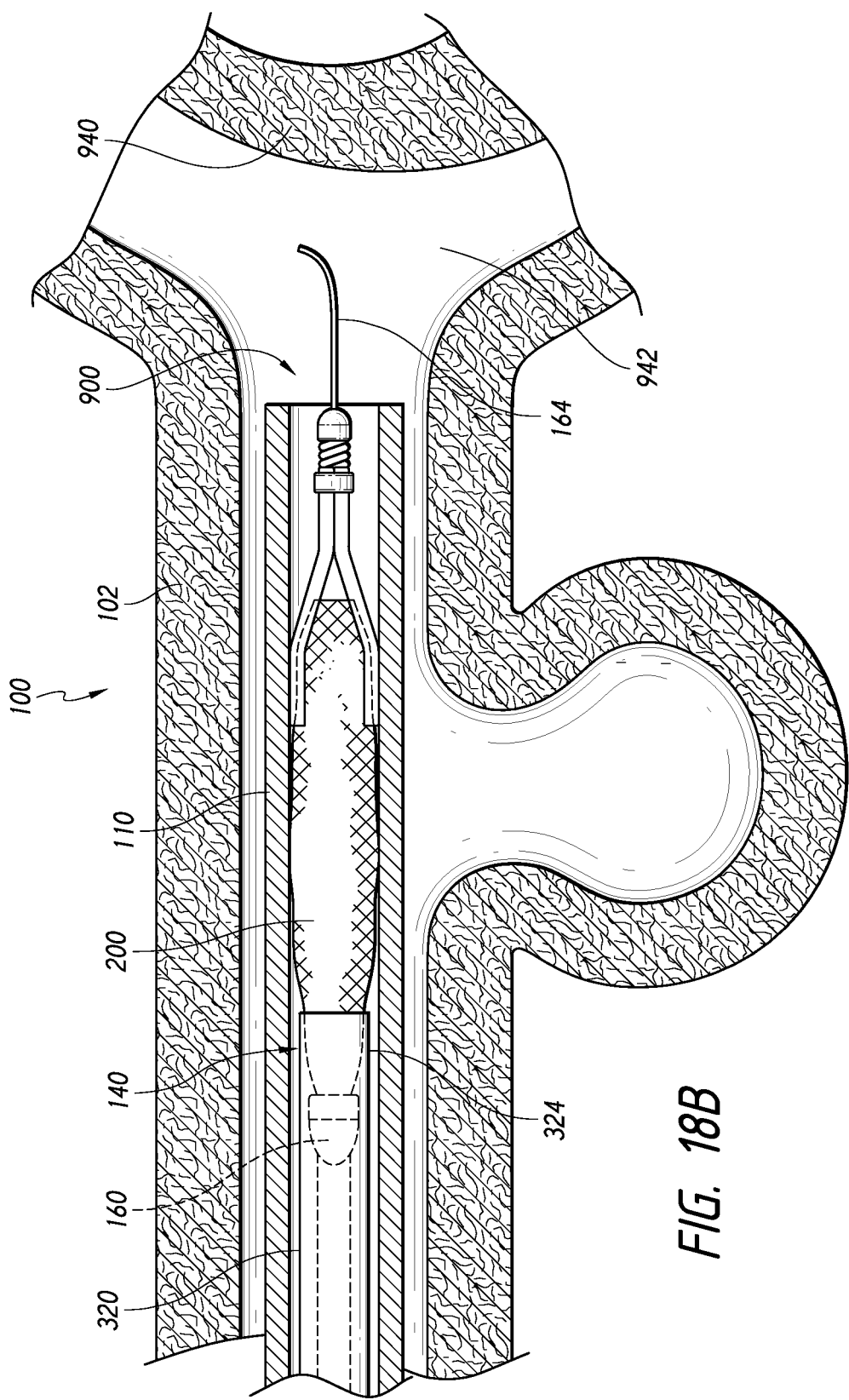
FIG. 18B is a schematic, partial cross-sectional view of the stent delivery system and the treatment site shown in FIG. 18A, in which a distal portion of a core member of the stent delivery system has been rotated to avoid abrading or perforation of a vessel wall, according to some embodiments.

The risk of abrasion or perforation can be substantially greater when the treatment location is adjacent to a bifurcation or sharp turn in the vessel. For example, FIGS. 18A-18B illustrate a scenario in which an apex 940 of a bifurcation 942 lies in the anticipated path of the distal end 164 of the core member 160. As such, if the distal end 164 is advanced distally towards the apex 940 in the position, configuration, or orientation shown in FIG. 18A (and especially if the core member and distal tip are straight and not curved), there is a likelihood that the apex of the bifurcation will be abraded or perforated by the distal tip of the core member.

However, as shown in FIG. 18B, in order to avoid the abrasion or perforation, the distal end 164 of the core member 160 can be rotated to reorient the curved portion of the distal end 164 toward a lower-risk pathway such as a desired branch vessel. The distal end 164 can be formed from a radiopaque material to make the distal end 164 visible under electromagnetic radiation or other imaging, and therefore facilitate recognition by the clinician of the orientation of the distal end 164 with respect to the surrounding vasculature. Having observed the orientation of the distal end 164, the clinician can determine how to "aim" the distal end 164 of the core member 160 to avoid abrasion or perforation of the vessel wall. For example, in accordance with some embodiments, after determining the appropriate direction after viewing the position of the distal end 164, the clinician can rotate and reorient the distal end 164 to point the core member 160 in a desired or lower-risk direction by rotating a proximal end of the core member 160. Further, as noted herein, rotation of the core member relative to the stent can allow the clinician to avoid dislodging the stent from the vessel wall after initial expansion of the stent and also avoid abrasion or perforation of the blood vessel. In this manner, the stent delivery system can advantageously allow a clinician to steer and control the articulation of the stent delivery system to ensure that the vessels adjacent to the treatment site are not damaged as the stent is deployed and the core assembly 140 is advanced.

Information regarding additional embodiments of the stent delivery system 100, and additional details and components that can optionally be used or implemented in the embodiments of the stent delivery system described herein, can be found in the above-incorporated U.S. Patent Application Publications Nos. US 2011/0152998A1 and US 2009/0318947A1. The stent delivery system 100 disclosed herein can optionally be similar to any of the delivery systems disclosed in these publications, except as further described herein.

The apparatus and methods discussed herein are not limited to the expansion and use of an stent or occluding device within any particular vessels, but may include any number of different types of vessels. For example, in some aspects, vessels may include arteries or veins. The vessels may have bifurcations and/or sharp turns. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyro cervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, the delivery system can include an expandable occluding device (e.g., stent) configured to be placed across an aneurysm. The occluding device can be delivered through the distal portion of the catheter, out a distal tip assembly, and into the vasculature adjacent an aneurysm in, for example, the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

The apparatus and methods discussed herein are not limited to the deployment and use of an occluding device or stent within the vascular system but may include any number of further treatment applications. Other treatment sites may include areas or regions of the body such as organ bodies.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

What is claimed is:

1. A stent delivery system, comprising:
   a core member having a distal segment; and
   first and second restraints coupled to the core member distal segment and axially spaced apart from each other to provide an axial gap, the first and second restraints each having an outer profile that tapers radially inwardly;
   a stent engagement component rotatably coupled to the core member between the first and second restraints.

2. The system of claim 1, further comprising a stent extending over at least one of the first or second restraints.

3. The system of claim 2, wherein the system is configured to permit the core member to bend in a curved path without causing the first and second restraints to compress the stent against an inner wall of the catheter.

4. The system of claim 2, wherein the system is configured to permit the core member to bend in a curved path without causing the first and second restraints to contact an inner surface of the stent.

5. The system of claim 1, wherein the first and second restraints each have an outer profile that tapers radially inwardly in directions away from each other.

6. The system of claim 1, wherein the first restraint is positioned distally of the second restraint.

7. The stent delivery system of claim 1, wherein the stent engagement component comprises an engagement member configured to cooperate with an inner wall of the catheter to grip the stent to move the stent within the catheter.

8. The system of claim 1, wherein the delivery system comprises a first radiopaque marker and the catheter comprises a second radiopaque marker longitudinally movable relative to the first radiopaque marker, and wherein the system is configured such that longitudinally aligning the first and second radiopaque markers achieves a pre-release position beyond which additional distal advancement of the core member permits release of the stent from the delivery system.

9. The system of claim 8, wherein the first restraint comprises the first radiopaque marker and a distal portion of the catheter comprises the second radiopaque marker.

10. The stent delivery system of claim 8, wherein the second radiopaque marker is positioned at the catheter distal end, and the advancing comprises longitudinally aligning the first restraint with the catheter distal end.

11. A stent delivery system, comprising:
    a catheter having a lumen;
    a core member having a distal segment and configured to be received within the catheter lumen;
    first and second restraints coupled to the core member distal segment and axially spaced apart from each other to provide an axial gap, the first and second restraints each having an outer profile that tapers radially inwardly; and
    a stent engagement member rotatably coupled to the core member distal segment in the axial gap.

12. The system of claim 11, wherein the first and second restraints have maximum outer cross-sectional profiles that are less than a maximum diameter of the stent engagement member.

13. The system of claim 11, wherein the first and second restraints have different maximum outer cross-sectional profiles.

14. The system of claim 11, further comprising (i) a third restraint spaced apart from the first and second restraints and providing a second axial gap and (ii) a second stent engagement member rotatably coupled to the core member distal segment in the second axial gap.

15. The system of claim 11, wherein the delivery system comprises a first radiopaque marker, the catheter comprises a second radiopaque marker, the first and second radiopaque markers being longitudinally movable relative to each other and longitudinally alignable with each other such that the system achieves a pre-release position beyond which additional distal advancement of the core member permits release of a stent from the delivery system.

16. The system of claim 15, wherein the first restraint comprises the first radiopaque marker, and a distal portion of the catheter comprises the second radiopaque marker.

17. The system of claim 16, wherein the second radiopaque marker is positioned at the catheter distal end.

* * * * *